US011478578B2

(12) United States Patent
Farrell et al.

(10) Patent No.: US 11,478,578 B2
(45) Date of Patent: Oct. 25, 2022

(54) MEDICAL FLUID CASSETTES AND RELATED SYSTEMS AND METHODS

(71) Applicant: Fresenius Medical Care Holdings, Inc., Waltham, MA (US)

(72) Inventors: Sean Farrell, Fresno, CA (US); Joseph Michael Fallon, Dixon, CA (US); Kulwinder S. Plahey, Martinez, CA (US); Michael James Beiriger, Pittsburgh, PA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 349 days.

(21) Appl. No.: 16/579,062

(22) Filed: Sep. 23, 2019

(65) Prior Publication Data

US 2020/0016313 A1    Jan. 16, 2020

Related U.S. Application Data

(62) Division of application No. 15/475,342, filed on Mar. 31, 2017, now Pat. No. 10,463,777, which is a
(Continued)

(51) Int. Cl.
*A61M 1/28*      (2006.01)
*F04B 9/02*      (2006.01)
*F04B 43/02*     (2006.01)
*F04B 53/10*     (2006.01)
*F04B 53/16*     (2006.01)

(52) U.S. Cl.
CPC ............. *A61M 1/28* (2013.01); *F04B 9/02* (2013.01); *F04B 43/025* (2013.01); *F04B 53/10* (2013.01); *F04B 53/16* (2013.01); *A61M 2205/12* (2013.01); *A61M 2205/121* (2013.01); *A61M 2205/36* (2013.01); *A61M 2209/084* (2013.01)

(58) Field of Classification Search
CPC ....... A61M 1/28; A61M 2205/12; F04B 9/02; F04B 43/025; F04B 53/10; F04B 53/16
USPC ......................................................... 604/28
See application file for complete search history.

(56) References Cited

U.S. PATENT DOCUMENTS 329,773  A    11/1885  Perry
862,867  A    8/1907   Eggleston
(Continued)

FOREIGN PATENT DOCUMENTS

CA    2101232 A1    1/1995
CN    1099103 A     2/1995
(Continued)

OTHER PUBLICATIONS

Bolegoh, Gordon, "Pumps: Reference Guide", p. 24, 3rd edition, 2001.
(Continued)

*Primary Examiner* — Phillip A Gray
(74) *Attorney, Agent, or Firm* — Fish & Richardson P.C.

(57) ABSTRACT

This disclosure relates to medical fluid cassettes and related systems and methods. In certain aspects, a medical fluid cassette includes a base having a first region and a second region, a first membrane overlying the first region of the base, and a second membrane overlying the second region of the base. The second membrane is configured to rebound away from the base when a force used to press the second membrane toward the base is released.

9 Claims, 21 Drawing Sheets

Related U.S. Application Data division of application No. 13/492,370, filed on Jun. 8, 2012, now Pat. No. 9,610,392.

(56) References Cited

U.S. PATENT DOCUMENTS

| | | |
|---|---|---|
| 1,029,232 A | 6/1912 | Schaefer et al. |
| 1,946,343 A | 2/1934 | Wicha |
| 2,308,974 A | 1/1943 | Harper |
| 2,311,229 A | 2/1943 | Herbert |
| 2,356,738 A | 8/1944 | Brugger |
| 2,383,193 A | 8/1945 | Herbert |
| 2,453,590 A | 11/1948 | Poux |
| 2,529,028 A | 11/1950 | Landon |
| 2,658,526 A | 11/1953 | Porter |
| 2,711,134 A | 6/1955 | Hughes |
| 2,726,019 A | 12/1955 | Moran |
| 2,732,807 A | 1/1956 | Parsegian |
| 2,755,745 A | 1/1956 | Lewis |
| 2,740,259 A | 4/1956 | Westlund |
| 2,755,134 A | 7/1956 | Eck et al. |
| 2,821,930 A | 2/1958 | Ashbrooke |
| 2,836,121 A | 5/1958 | Browne |
| 2,843,050 A | 7/1958 | Harper |
| 2,855,144 A | 10/1958 | Andreasen |
| 2,861,596 A | 11/1958 | Ipsen |
| 2,871,795 A | 2/1959 | Smith |
| 2,886,281 A | 5/1959 | Canalizo |
| 2,895,653 A | 7/1959 | Giepen |
| 2,920,573 A | 1/1960 | Schaurte |
| 2,980,032 A | 4/1961 | Schneider |
| 3,013,575 A | 12/1961 | Persson |
| 3,036,526 A | 5/1962 | Hise |
| 3,039,399 A | 6/1962 | Everett |
| 3,045,601 A | 7/1962 | Rippingille |
| 3,083,943 A | 4/1963 | Stewart et al. |
| 3,106,844 A | 10/1963 | Sonnberg |
| 3,148,624 A | 9/1964 | Baldwin |
| 3,151,783 A | 10/1964 | Shaw et al. |
| 3,208,721 A | 9/1965 | Mchugh |
| 3,216,415 A | 11/1965 | Littleton |
| 3,240,152 A | 3/1966 | Bower, Jr. |
| 3,252,623 A | 5/1966 | Corbin et al. |
| 3,256,825 A | 6/1966 | Limpert et al. |
| 3,285,182 A | 11/1966 | Pinkerton |
| 3,286,577 A | 11/1966 | Weidner, Jr. |
| 3,307,481 A | 3/1967 | De Castelet |
| 3,310,281 A | 3/1967 | Boteler |
| 3,314,371 A | 4/1967 | Hopkinson |
| 3,318,324 A | 5/1967 | Ruth |
| 3,323,786 A | 6/1967 | Boschi |
| 3,379,216 A | 4/1968 | Mercier |
| 3,386,388 A | 6/1968 | Rosenberg |
| 3,387,566 A | 6/1968 | Temple |
| 3,397,216 A | 8/1968 | Welch et al. |
| 3,461,808 A | 8/1969 | Nelson et al. |
| 3,491,675 A | 1/1970 | Gold |
| 3,508,848 A | 4/1970 | Schmidlin |
| 3,514,227 A | 5/1970 | Rupp |
| 3,533,387 A | 10/1970 | Tomoichi |
| 3,556,465 A | 1/1971 | Little |
| 3,645,992 A | 2/1972 | Elston |
| 3,652,187 A | 3/1972 | Loeffler et al. |
| 3,654,953 A | 4/1972 | Hagdorn |
| 3,655,603 A | 4/1972 | Morton et al. |
| 3,656,873 A | 4/1972 | Schiff |
| 3,661,060 A | 5/1972 | Bowen |
| 3,666,379 A | 5/1972 | Mitchell et al. |
| 3,668,978 A | 6/1972 | Bowen |
| 3,671,814 A | 6/1972 | Dick |
| 3,685,789 A | 8/1972 | Puster et al. |
| 3,689,025 A | 9/1972 | Kiser |
| 3,693,611 A | 9/1972 | Ploss |
| 3,697,197 A | 10/1972 | Berglund et al. |
| 3,718,552 A | 2/1973 | Mortell |
| 3,727,623 A | 4/1973 | Robbins |
| 3,741,687 A | 6/1973 | Nystroern |
| 3,743,245 A | 7/1973 | Demler |
| 3,776,107 A | 12/1973 | Molus |
| 3,777,625 A | 12/1973 | Andres |
| 3,781,141 A | 12/1973 | Schall |
| 3,785,378 A | 1/1974 | Stewart |
| 3,800,794 A | 4/1974 | Georgi |
| 3,807,406 A | 4/1974 | Rafferty et al. |
| 3,807,906 A | 4/1974 | Breit |
| 3,814,548 A | 6/1974 | Rupp |
| 3,816,034 A | 6/1974 | Rosenquest |
| 3,838,946 A | 10/1974 | Schall |
| 3,902,490 A | 9/1975 | Jacobsen et al. |
| 3,880,053 A | 12/1975 | Trechsel et al. |
| 3,927,955 A | 12/1975 | Spinosa et al. |
| 3,955,901 A | 5/1976 | Hamilton |
| 3,966,358 A | 6/1976 | Heimes et al. |
| 3,985,133 A | 10/1976 | Jenkins et al. |
| 3,985,135 A | 10/1976 | Carpenter et al. |
| 3,995,774 A | 12/1976 | Cooprider et al. |
| 4,008,710 A | 2/1977 | Chmiel |
| 4,021,149 A | 5/1977 | Rutenberg et al. |
| 4,021,164 A | 5/1977 | Tell |
| 4,026,669 A | 5/1977 | Leonard et al. |
| 4,042,311 A | 8/1977 | Yonezawa |
| 4,046,610 A | 9/1977 | Lilja |
| 4,047,844 A | 9/1977 | Robinson |
| 4,050,859 A | 9/1977 | Vork |
| 4,089,342 A | 5/1978 | Stradella et al. |
| 4,091,812 A | 5/1978 | Helixon et al. |
| 4,093,406 A | 6/1978 | Miller |
| 4,104,008 A | 8/1978 | Hoffmann et al. |
| 4,121,236 A | 10/1978 | Welp et al. |
| 4,121,584 A | 10/1978 | Turner et al. |
| 4,123,204 A | 10/1978 | Scholle |
| 4,127,160 A | 11/1978 | Joffe |
| 4,135,496 A | 1/1979 | Chazov et al. |
| 4,142,523 A | 3/1979 | Stegeman |
| 4,142,524 A | 3/1979 | Jassawalla et al. |
| 4,150,922 A | 4/1979 | Cuenoud et al. |
| 4,151,184 A | 4/1979 | Smith |
| 4,152,098 A | 5/1979 | Moody et al. |
| 4,158,530 A | 6/1979 | Bernstein |
| 4,162,876 A | 7/1979 | Kolfertz |
| 4,178,940 A | 12/1979 | Au |
| 4,181,245 A | 1/1980 | Garrett et al. |
| 4,185,759 A | 1/1980 | Zissimopoulos |
| 4,199,307 A | 4/1980 | Jassawalla |
| 4,204,538 A | 5/1980 | Cannon |
| 4,205,238 A | 5/1980 | Knigge et al. |
| 4,214,237 A | 7/1980 | Zissimopoulos |
| 4,222,127 A | 9/1980 | Donachy et al. |
| 4,222,813 A | 9/1980 | Jodrey |
| 4,230,844 A | 10/1980 | Chang et al. |
| 4,236,880 A | 12/1980 | Archibald |
| 4,261,356 A | 4/1981 | Turner et al. |
| 4,262,668 A | 4/1981 | Schmidt |
| 4,262,824 A | 4/1981 | Hrynewycz |
| 4,263,808 A | 4/1981 | Bellotti |
| 4,264,020 A | 4/1981 | Loiseau |
| 4,265,506 A | 5/1981 | Hollyday |
| 4,265,600 A | 5/1981 | Mandroian |
| 4,265,601 A | 5/1981 | Mandroian |
| 4,266,657 A | 5/1981 | Frost et al. |
| 4,273,121 A | 6/1981 | Jassawalla |
| 4,276,004 A | 6/1981 | Hahn |
| 4,277,226 A | 7/1981 | Archibald |
| 4,303,376 A | 12/1981 | Siekmann |
| 4,304,260 A | 12/1981 | Turner et al. |
| 4,308,978 A | 1/1982 | Bayly et al. |
| 4,312,344 A | 1/1982 | Nilson |
| 4,321,939 A | 3/1982 | Fenwick |
| 4,322,201 A | 3/1982 | Archibald |
| 4,332,254 A | 6/1982 | Lundquist |
| 4,333,452 A | 6/1982 | Au |
| 4,364,386 A | 12/1982 | Jenkins et al. |
| 4,370,983 A | 2/1983 | Lichtenstein |
| 4,381,180 A | 4/1983 | Sell |
| 4,382,753 A | 5/1983 | Archibald |

(56) References Cited

U.S. PATENT DOCUMENTS

| | | |
|---|---|---|
| 4,410,322 A | 10/1983 | Archibald |
| 4,411,603 A | 10/1983 | Kell |
| 4,411,651 A | 10/1983 | Schulman |
| 4,412,553 A | 11/1983 | Kopp et al. |
| 4,421,506 A | 12/1983 | Danby et al. |
| 4,430,048 A | 2/1984 | Fritsch |
| 4,431,019 A | 2/1984 | Kopp et al. |
| 4,436,620 A | 3/1984 | Bellotti et al. |
| 4,453,931 A | 6/1984 | Pastrone |
| 4,453,932 A | 6/1984 | Pastrone |
| 4,468,177 A | 8/1984 | Strimling |
| 4,479,760 A | 10/1984 | Bilstad et al. |
| 4,479,761 A | 10/1984 | Bilstad et al. |
| 4,479,762 A | 10/1984 | Bilstad et al. |
| 4,483,665 A | 11/1984 | Hauser |
| 4,490,621 A | 12/1984 | Watabe et al. |
| 4,493,709 A | 1/1985 | Smith |
| 4,496,294 A | 1/1985 | Frikker |
| 4,497,760 A | 2/1985 | Sorlien |
| 4,501,300 A | 2/1985 | Murphy |
| 4,511,616 A | 4/1985 | Pitts et al. |
| 4,514,295 A | 4/1985 | Mathieu et al. |
| 4,515,017 A | 5/1985 | McConaghy |
| 4,515,792 A | 5/1985 | Watthey |
| 4,519,792 A | 5/1985 | Dawe |
| 4,523,598 A | 6/1985 | Weiss et al. |
| 4,527,411 A | 7/1985 | Shinosaki et al. |
| 4,536,201 A | 8/1985 | Brorsson et al. |
| 4,538,638 A | 9/1985 | Stack |
| 4,542,735 A | 9/1985 | Smith et al. |
| 4,543,044 A | 9/1985 | Simmons |
| 4,550,066 A | 10/1985 | Alexander et al. |
| 4,550,134 A | 10/1985 | Isogai et al. |
| 4,552,552 A | 11/1985 | Polaschegg et al. |
| 4,553,910 A | 11/1985 | Gosschalk |
| 4,558,715 A | 12/1985 | Walton et al. |
| 4,559,044 A | 12/1985 | Robinson et al. |
| 4,569,378 A | 2/1986 | Bergandy |
| 4,573,883 A | 3/1986 | Noon et al. |
| 4,583,920 A | 4/1986 | Lindner |
| 4,586,738 A | 5/1986 | Butler et al. |
| 4,597,412 A | 7/1986 | Stark |
| 4,605,396 A | 8/1986 | Tseo et al. |
| 4,606,374 A | 8/1986 | Kolenc et al. |
| 4,610,605 A | 9/1986 | Hartley |
| 4,611,578 A | 9/1986 | Heimes |
| 4,623,328 A | 11/1986 | Hartranft |
| 4,624,625 A | 11/1986 | Schrenker |
| 4,627,419 A | 12/1986 | Hills |
| 4,627,837 A | 12/1986 | Gonzalo |
| 4,628,499 A | 12/1986 | Hammett |
| 4,634,430 A | 1/1987 | Polaschegg |
| 4,636,149 A | 1/1987 | Brown |
| 4,639,245 A | 1/1987 | Pastrone et al. |
| 4,643,713 A | 2/1987 | Viitala |
| 4,644,897 A | 2/1987 | Fender |
| 4,646,781 A | 3/1987 | McIntyre et al. |
| 4,657,490 A | 4/1987 | Abbott |
| 4,662,598 A | 5/1987 | Weingarten |
| 4,662,906 A | 5/1987 | Matkovich et al. |
| 4,676,467 A | 6/1987 | Palsulich |
| 4,684,106 A | 8/1987 | Kolenc et al. |
| 4,690,621 A | 9/1987 | Swain |
| 4,698,207 A | 10/1987 | Bringham et al. |
| 4,703,913 A | 11/1987 | Hunkapiller |
| 4,705,259 A | 11/1987 | Dolhen et al. |
| 4,710,166 A | 12/1987 | Thompson et al. |
| 4,735,558 A | 4/1988 | Kienholz et al. |
| 4,741,678 A | 5/1988 | Nehring |
| 4,746,436 A | 5/1988 | Kopp et al. |
| 4,755,111 A | 7/1988 | Cocchi et al. |
| 4,755,228 A | 7/1988 | Sakurai et al. |
| 4,758,238 A | 7/1988 | Sundblom et al. |
| 4,759,264 A | 7/1988 | Danby et al. |
| 4,763,051 A | 8/1988 | Ruppert |
| 4,768,547 A | 9/1988 | Danby et al. |
| 4,773,218 A | 9/1988 | Wakita et al. |
| 4,778,451 A | 10/1988 | Kamen |
| 4,781,715 A | 11/1988 | Wurzel |
| 4,786,240 A | 11/1988 | Koroly et al. |
| 4,787,825 A | 11/1988 | Mantell |
| 4,808,161 A | 2/1989 | Kamen |
| 4,817,503 A | 4/1989 | Yamada |
| 4,818,186 A | 4/1989 | Pastrone et al. |
| 4,818,190 A | 4/1989 | Pelmulder et al. |
| 4,821,761 A | 4/1989 | Aid et al. |
| 4,826,482 A | 5/1989 | Kamen |
| 4,830,586 A | 5/1989 | Herter et al. |
| 4,840,542 A | 6/1989 | Abbott |
| 4,842,584 A | 6/1989 | Pastrone |
| 4,846,636 A | 7/1989 | Danby et al. |
| 4,850,817 A | 7/1989 | Nason et al. |
| 4,850,980 A | 7/1989 | Lentz et al. |
| 4,854,832 A | 8/1989 | Gardner et al. |
| 4,856,335 A | 8/1989 | Tornberg |
| 4,856,340 A | 8/1989 | Garrison |
| 4,857,048 A | 8/1989 | Simons et al. |
| 4,858,883 A | 8/1989 | Webster |
| 4,869,282 A | 9/1989 | Sittler et al. |
| 4,872,813 A | 10/1989 | Gorton et al. |
| 4,874,297 A | 10/1989 | Collins et al. |
| 4,882,346 A | 11/1989 | Driscoll et al. |
| 4,888,011 A | 12/1989 | Kung et al. |
| 4,894,164 A | 1/1990 | Polaschegg |
| 4,896,215 A | 1/1990 | Morcom |
| 4,900,305 A | 2/1990 | Smith et al. |
| 4,902,282 A | 2/1990 | Bellotti et al. |
| 4,906,260 A | 3/1990 | Emheiser et al. |
| 4,915,017 A | 4/1990 | Perlov |
| 4,917,348 A | 4/1990 | Phallen et al. |
| 4,927,411 A | 5/1990 | Pastrone et al. |
| 4,928,605 A | 5/1990 | Suwa et al. |
| 4,935,125 A | 6/1990 | Era et al. |
| 4,938,742 A | 7/1990 | Smits |
| 4,944,487 A | 7/1990 | Holtermann |
| 4,950,134 A | 8/1990 | Bailey et al. |
| 4,969,866 A | 11/1990 | Inagaki |
| 4,974,754 A | 12/1990 | Wirz |
| 4,974,774 A | 12/1990 | Nakagawa et al. |
| 4,976,162 A | 12/1990 | Kamen |
| 4,981,418 A | 1/1991 | Kingsford et al. |
| 4,995,864 A | 2/1991 | Bartholomew et al. |
| 4,997,464 A | 3/1991 | Kopf |
| 5,002,471 A | 3/1991 | Perlov |
| 5,006,050 A | 4/1991 | Cooke et al. |
| 5,011,368 A | 4/1991 | Frindel et al. |
| 5,011,380 A | 4/1991 | Kovacs |
| 5,024,644 A | 6/1991 | Bunch, III |
| 5,036,886 A | 8/1991 | Olsen et al. |
| 5,038,640 A | 8/1991 | Sullivan et al. |
| 5,044,901 A | 9/1991 | Fumero et al. |
| 5,061,236 A | 10/1991 | Sutherland et al. |
| 5,062,770 A | 11/1991 | Story et al. |
| 5,062,774 A | 11/1991 | Kramer et al. |
| 5,088,515 A | 2/1992 | Kamen |
| 5,092,377 A | 3/1992 | Krumberger |
| 5,092,414 A | 3/1992 | Blezard |
| 5,095,141 A | 3/1992 | Schammel et al. |
| 5,098,262 A | 3/1992 | Wecker et al. |
| 5,098,377 A | 3/1992 | Borsanyi et al. |
| 5,100,380 A | 3/1992 | Epstein |
| 5,100,699 A | 3/1992 | Roeser |
| 5,108,367 A | 4/1992 | Epstein et al. |
| 5,116,021 A | 5/1992 | Faust et al. |
| 5,116,136 A | 5/1992 | Newman et al. |
| 5,116,316 A | 5/1992 | Sertic et al. |
| 5,145,331 A | 9/1992 | Goes et al. |
| 5,146,713 A | 9/1992 | Grafius |
| 5,151,019 A | 9/1992 | Danby et al. |
| 5,158,210 A | 10/1992 | Du |
| 5,158,529 A | 10/1992 | Kanai |
| 5,167,387 A | 12/1992 | Hartwick |
| 5,167,837 A | 12/1992 | Snodgrass et al. |
| 5,171,029 A | 12/1992 | Maxwell et al. |

(56) References Cited

U.S. PATENT DOCUMENTS

| | | |
|---|---|---|
| 5,178,182 A | 1/1993 | Kamen |
| 5,193,977 A | 3/1993 | Dame |
| 5,193,990 A | 3/1993 | Kamen et al. |
| 5,201,636 A | 4/1993 | Mikulski |
| 5,205,722 A | 4/1993 | Hammond |
| 5,211,201 A | 5/1993 | Kamen et al. |
| 5,213,485 A | 5/1993 | Wilden |
| 5,232,434 A | 8/1993 | Inagaki et al. |
| 5,238,003 A | 8/1993 | Baidwan et al. |
| 5,241,985 A | 9/1993 | Faust et al. |
| 5,242,384 A | 9/1993 | Robinson et al. |
| 5,247,434 A | 9/1993 | Peterson et al. |
| 5,249,932 A | 10/1993 | Van Bork |
| 5,252,041 A | 10/1993 | Schumack |
| 5,252,044 A | 10/1993 | Raines et al. |
| 5,259,352 A | 11/1993 | Gerhardy et al. |
| 5,261,798 A | 11/1993 | Budde |
| 5,262,068 A | 11/1993 | Bowers et al. |
| 5,267,956 A | 12/1993 | Beuchat |
| 5,269,811 A | 12/1993 | Hayes et al. |
| 5,279,504 A | 1/1994 | Williams |
| 5,279,556 A | 1/1994 | Goi et al. |
| 5,292,384 A | 3/1994 | Klueh et al. |
| 5,302,093 A | 4/1994 | Owens et al. |
| 5,304,126 A | 4/1994 | Epstein et al. |
| 5,324,422 A | 6/1994 | Colleran et al. |
| 5,330,425 A | 7/1994 | Utterberg |
| 5,332,372 A | 7/1994 | Reynolds |
| 5,342,182 A | 8/1994 | Montoya et al. |
| 5,344,292 A | 9/1994 | Rabenau et al. |
| 5,350,357 A | 9/1994 | Kamen et al. |
| D351,470 S | 10/1994 | Scherer et al. |
| 5,353,837 A | 10/1994 | Faust |
| 5,368,452 A | 11/1994 | Johnson et al. |
| 5,378,126 A | 1/1995 | Abrahamson et al. |
| 5,391,060 A | 2/1995 | Kozumplik et al. |
| 5,395,351 A | 3/1995 | Munsch |
| 5,401,963 A | 3/1995 | Sittler |
| 5,413,626 A | 5/1995 | Bartsch |
| 5,415,528 A | 5/1995 | Ogden et al. |
| 5,421,208 A | 6/1995 | Packard et al. |
| 5,421,823 A | 6/1995 | Kamen et al. |
| 5,423,738 A | 6/1995 | Robinson et al. |
| 5,427,509 A | 6/1995 | Chapman et al. |
| 5,429,485 A | 7/1995 | Dodge |
| 5,431,626 A | 7/1995 | Bryant et al. |
| 5,431,627 A | 7/1995 | Pastrone et al. |
| 5,431,634 A | 7/1995 | Brown |
| 5,437,542 A | 8/1995 | Ewing |
| 5,438,510 A | 8/1995 | Bryant et al. |
| 5,441,392 A | 8/1995 | Lundback |
| 5,441,636 A | 8/1995 | Chevallet et al. |
| 5,445,506 A | 8/1995 | Afterbaugh et al. |
| 5,447,286 A | 9/1995 | Kamen et al. |
| 5,462,416 A | 10/1995 | Dennehey et al. |
| 5,462,417 A | 10/1995 | Chapman |
| 5,464,352 A | 11/1995 | Van Emmerick |
| 5,474,683 A | 12/1995 | Bryant et al. |
| 5,476,368 A | 12/1995 | Rabenau et al. |
| 5,476,378 A | 12/1995 | Zagoroff et al. |
| 5,478,211 A | 12/1995 | Dominiak et al. |
| 5,480,292 A | 1/1996 | Chevallier |
| 5,480,294 A | 1/1996 | Di Perna et al. |
| 5,482,438 A | 1/1996 | Anderson et al. |
| 5,482,440 A | 1/1996 | Dennehey et al. |
| 5,482,446 A | 1/1996 | Williamson et al. |
| 5,484,239 A | 1/1996 | Chapman et al. |
| 5,486,286 A | 1/1996 | Peterson et al. |
| 5,490,765 A | 2/1996 | Bailey et al. |
| 5,499,906 A | 3/1996 | O'Leary |
| 5,499,909 A | 3/1996 | Yamada et al. |
| 5,502,096 A | 3/1996 | Kimura et al. |
| 5,503,538 A | 4/1996 | Wiernicki et al. |
| 5,514,069 A | 5/1996 | Brown et al. |
| 5,520,523 A | 5/1996 | Yorita et al. |
| 5,522,998 A | 6/1996 | Polaschegg |
| 5,524,865 A | 6/1996 | Uchisawa et al. |
| 5,527,161 A | 6/1996 | Bailey et al. |
| 5,538,405 A | 7/1996 | Patno et al. |
| 5,540,568 A | 7/1996 | Rosen et al. |
| 5,547,453 A | 8/1996 | Di Perna |
| 5,551,850 A | 9/1996 | Williamson et al. |
| 5,551,941 A | 9/1996 | Howell |
| 5,551,942 A | 9/1996 | Brown et al. |
| 5,554,011 A | 9/1996 | Bales et al. |
| 5,554,013 A | 9/1996 | Owens et al. |
| 5,554,108 A | 9/1996 | Browning et al. |
| 5,558,506 A | 9/1996 | Simmons et al. |
| 5,567,118 A | 10/1996 | Grgurich et al. |
| 5,570,716 A | 11/1996 | Kamen et al. |
| 5,573,385 A | 11/1996 | Chevallier |
| 5,578,070 A | 11/1996 | Utterberg |
| 5,586,868 A | 12/1996 | Lawless |
| 5,588,816 A | 12/1996 | Abbott et al. |
| 5,593,290 A | 1/1997 | Greisch et al. |
| 5,599,174 A | 2/1997 | Cook |
| 5,601,420 A | 2/1997 | Warner et al. |
| 5,609,572 A | 3/1997 | Lang |
| 5,614,677 A | 3/1997 | Wamsiedler et al. |
| 5,624,409 A | 4/1997 | Seale |
| 5,628,908 A | 5/1997 | Kamen et al. |
| 5,630,710 A | 5/1997 | Tune et al. |
| 5,634,896 A | 5/1997 | Bryant et al. |
| 5,634,391 A | 6/1997 | Eady |
| 5,640,995 A | 6/1997 | Packard et al. |
| 5,641,405 A | 6/1997 | Keshaviah et al. |
| 5,641,892 A | 6/1997 | Larkins et al. |
| 5,643,205 A | 7/1997 | Utterberg |
| 5,645,531 A | 7/1997 | Thompson et al. |
| 5,647,733 A | 7/1997 | Augustyn et al. |
| 5,653,251 A | 8/1997 | Handler |
| 5,656,032 A | 8/1997 | Kriesel et al. |
| 5,658,133 A | 8/1997 | Anderson et al. |
| 5,660,722 A | 8/1997 | Nederlof |
| 5,667,368 A | 9/1997 | Augustyn et al. |
| 5,669,724 A | 9/1997 | Kato |
| 5,669,764 A | 9/1997 | Behringer et al. |
| 5,687,633 A | 11/1997 | Eady |
| 5,690,602 A | 11/1997 | Brown et al. |
| 5,698,262 A | 12/1997 | Soubeyrand et al. |
| 5,709,534 A | 1/1998 | O'Leary |
| D390,654 S | 2/1998 | Alsberg et al. |
| 5,713,865 A | 2/1998 | Manning et al. |
| 5,713,888 A | 2/1998 | Neuenfeldt et al. |
| 5,718,565 A | 2/1998 | Kuhn et al. |
| 5,718,567 A | 2/1998 | Rapp et al. |
| 5,725,363 A | 3/1998 | Buestgens et al. |
| 5,741,121 A | 4/1998 | O'Leary |
| 5,741,125 A | 4/1998 | Neftel et al. |
| 5,743,169 A | 4/1998 | Yamada |
| 5,743,170 A | 4/1998 | Pascual et al. |
| 5,746,708 A | 5/1998 | Giesler et al. |
| 5,755,683 A | 5/1998 | Houle et al. |
| 5,764,034 A | 6/1998 | Bowman et al. |
| 5,769,387 A | 6/1998 | Perez |
| 5,771,914 A | 6/1998 | Ling et al. |
| 5,772,635 A | 6/1998 | Dastur et al. |
| 5,772,637 A | 6/1998 | Heinzmann et al. |
| 5,775,371 A | 7/1998 | Pan et al. |
| 5,782,575 A | 7/1998 | Vincent et al. |
| 5,782,805 A | 7/1998 | Meinzer et al. |
| 5,788,215 A | 8/1998 | Ryan |
| 5,799,207 A | 8/1998 | Wang et al. |
| 5,816,775 A | 10/1998 | Imai et al. |
| 5,816,779 A | 10/1998 | Lawless et al. |
| 5,836,750 A | 11/1998 | Cabuz |
| 5,840,151 A | 11/1998 | Munsch |
| 5,842,841 A | 12/1998 | Danby et al. |
| 5,843,035 A | 12/1998 | Bowman et al. |
| 5,848,881 A | 12/1998 | Frezza |
| 5,863,184 A | 1/1999 | Jueterbock et al. |
| 5,863,421 A | 1/1999 | Peter et al. |
| 5,868,696 A | 2/1999 | Giesler et al. |
| 5,873,853 A | 2/1999 | Keilman et al. |

(56) References Cited

U.S. PATENT DOCUMENTS

| | | |
|---|---|---|
| 5,902,096 A | 5/1999 | Behringer et al. |
| 5,906,598 A | 5/1999 | Giesler et al. |
| 5,921,951 A | 7/1999 | Morris |
| 5,924,448 A | 7/1999 | West |
| 5,925,011 A | 7/1999 | Faict et al. |
| 5,932,987 A | 8/1999 | McLoughlin |
| 5,934,885 A | 8/1999 | Farrell et al. |
| 5,935,099 A | 8/1999 | Peterson et al. |
| 5,938,634 A | 8/1999 | Packard |
| 5,984,897 A | 11/1999 | Petersen et al. |
| 5,989,423 A | 11/1999 | Kamen |
| 5,993,174 A | 11/1999 | Konishi |
| 5,996,634 A | 12/1999 | Dennehey et al. |
| 6,003,835 A | 12/1999 | Moeller |
| 6,013,057 A | 1/2000 | Danby et al. |
| 6,013,060 A | 1/2000 | Woodard |
| 6,036,668 A | 3/2000 | Mathis |
| 6,036,680 A | 3/2000 | Home et al. |
| 6,041,801 A | 3/2000 | Gray et al. |
| 6,042,784 A | 3/2000 | Wamsiedler et al. |
| 6,053,191 A | 4/2000 | Hussey |
| 6,065,389 A | 5/2000 | Riedlinger |
| 6,065,941 A | 5/2000 | Gray et al. |
| 6,068,612 A | 5/2000 | Bowman et al. |
| 6,071,090 A | 6/2000 | Miki et al. |
| 6,074,359 A | 6/2000 | Keshaviah et al. |
| 6,079,959 A | 6/2000 | Kingsford et al. |
| 6,099,492 A | 8/2000 | Le Boeuf |
| 6,105,829 A | 8/2000 | Snodgrass et al. |
| 6,106,246 A | 8/2000 | Steck et al. |
| 6,109,881 A | 8/2000 | Snodgrass et al. |
| 6,110,410 A | 8/2000 | Owens et al. |
| 6,118,207 A | 9/2000 | Ormerod et al. |
| 6,126,403 A | 10/2000 | Yamada |
| 6,129,517 A | 10/2000 | Danby et al. |
| 6,129,970 A | 10/2000 | Kenney et al. |
| 6,132,187 A | 10/2000 | Ericson |
| 6,136,565 A | 10/2000 | Best et al. |
| 6,152,705 A | 11/2000 | Kennedy et al. |
| 6,154,605 A | 11/2000 | Aonuma |
| 6,158,966 A | 12/2000 | Guespin et al. |
| 6,158,972 A | 12/2000 | Ruth |
| 6,164,621 A | 12/2000 | Bouchard et al. |
| 6,165,154 A | 12/2000 | Gray et al. |
| 6,168,394 B1 | 1/2001 | Forman et al. |
| 6,173,959 B1 | 1/2001 | Oikawa et al. |
| 6,178,996 B1 | 1/2001 | Suzuki |
| 6,179,801 B1 | 1/2001 | Holmes et al. |
| 6,184,356 B1 | 2/2001 | Anderson et al. |
| 6,189,857 B1 | 2/2001 | Zeger et al. |
| 6,190,136 B1 | 2/2001 | Meloche et al. |
| 6,192,745 B1 | 2/2001 | Tang et al. |
| 6,196,987 B1 | 3/2001 | Holmes et al. |
| 6,200,287 B1 | 3/2001 | Keller et al. |
| 6,206,644 B1 | 3/2001 | Pereira et al. |
| 6,208,107 B1 | 3/2001 | Maske et al. |
| 6,208,497 B1 | 3/2001 | Seale et al. |
| 6,210,361 B1 | 4/2001 | Kamen et al. |
| 6,220,295 B1 | 4/2001 | Bouchard et al. |
| 6,223,130 B1 | 4/2001 | Gray et al. |
| 6,227,807 B1 | 5/2001 | Chase |
| 6,227,824 B1 | 5/2001 | Stehr |
| 6,228,047 B1 | 5/2001 | Dadson |
| 6,229,753 B1 | 5/2001 | Kono et al. |
| 6,231,537 B1 | 5/2001 | Holmes et al. |
| 6,234,773 B1 | 5/2001 | Hill et al. |
| 6,234,919 B1 | 5/2001 | Mizeracki et al. |
| 6,234,989 B1 | 5/2001 | Brierton et al. |
| 6,238,576 B1 | 5/2001 | Yajima |
| 6,250,502 B1 | 6/2001 | Cote et al. |
| 6,258,078 B1 | 7/2001 | Thilly |
| 6,261,065 B1 | 7/2001 | Nayak et al. |
| 6,267,242 B1 | 7/2001 | Nagata et al. |
| 6,270,673 B1 | 8/2001 | Belt et al. |
| 6,280,406 B1 | 8/2001 | Dolecek et al. |
| 6,281,145 B1 | 8/2001 | Deguchi et al. |
| 6,284,142 B1 | 9/2001 | Muller |
| 6,285,155 B1 | 9/2001 | Maske et al. |
| 6,286,566 B1 | 9/2001 | Cline et al. |
| 6,293,926 B1 | 9/2001 | Sorensen et al. |
| 6,294,094 B1 | 9/2001 | Muller et al. |
| 6,296,450 B1 | 10/2001 | Westberg et al. |
| 6,297,322 B1 | 10/2001 | Ding et al. |
| 6,299,029 B1 | 10/2001 | Bonningue |
| 6,305,793 B1 | 10/2001 | Haines |
| 6,312,412 B1 | 11/2001 | Saled |
| 6,315,707 B1 | 11/2001 | Smith et al. |
| 6,315,754 B1 | 11/2001 | Daoud et al. |
| 6,316,864 B1 | 11/2001 | Ormerod |
| 6,322,488 B1 | 11/2001 | Westberg et al. |
| 6,325,775 B1 | 12/2001 | Thom et al. |
| 6,337,049 B1 | 1/2002 | Tamari |
| RE37,553 E | 2/2002 | Ciavarini et al. |
| 6,343,539 B1 | 2/2002 | Du |
| 6,343,614 B1 | 2/2002 | Gray et al. |
| 6,345,962 B1 | 2/2002 | Sutter |
| 6,348,156 B1 | 2/2002 | Vishnoi et al. |
| 6,350,110 B1 | 2/2002 | Martin |
| 6,361,518 B1 | 3/2002 | Brierton et al. |
| 6,364,857 B1 | 4/2002 | Gray et al. |
| 6,367,669 B1 | 4/2002 | Au et al. |
| 6,382,923 B1 | 5/2002 | Gray |
| 6,382,934 B2 | 5/2002 | Budde |
| 6,383,158 B1 | 5/2002 | Utterberg |
| 6,402,486 B1 | 6/2002 | Steck et al. |
| 6,406,276 B1 | 6/2002 | Normand et al. |
| 6,409,696 B1 | 6/2002 | Toavs et al. |
| 6,416,293 B1 | 7/2002 | Bouchard et al. |
| 6,416,295 B1 | 7/2002 | Nagai et al. |
| 6,419,822 B2 | 7/2002 | Muller et al. |
| 6,446,611 B2 | 9/2002 | Ishikawa |
| 6,455,676 B1 | 9/2002 | Weickert et al. |
| 6,464,474 B2 | 10/2002 | Schluecker |
| 6,471,855 B1 | 10/2002 | Odak et al. |
| 6,481,980 B1 | 11/2002 | Vandlik et al. |
| 6,484,383 B1 | 11/2002 | Herklotz |
| 6,489,896 B1 | 12/2002 | Platt et al. |
| 6,491,656 B1 | 12/2002 | Morris |
| 6,494,694 B2 | 12/2002 | Lawless et al. |
| 6,497,674 B1 | 12/2002 | Steele et al. |
| 6,497,676 B1 | 12/2002 | Childers et al. |
| 6,503,062 B1 | 1/2003 | Gray et al. |
| 6,514,225 B1 | 2/2003 | Utterberg et al. |
| 6,519,569 B1 | 2/2003 | White et al. |
| 6,520,747 B2 | 2/2003 | Gray et al. |
| 6,524,231 B1 | 2/2003 | Westberg et al. |
| 6,529,573 B2 | 3/2003 | Olsher et al. |
| 6,537,445 B2 | 3/2003 | Muller |
| 6,542,761 B1 | 4/2003 | Jahn et al. |
| 6,554,587 B2 | 4/2003 | Paolini et al. |
| 6,558,343 B1 | 5/2003 | Neftel |
| 6,572,604 B1 | 6/2003 | Platt et al. |
| 6,575,599 B1 | 6/2003 | Imamura et al. |
| 6,579,253 B1 | 6/2003 | Burbank et al. |
| 6,582,399 B1 | 6/2003 | Smith |
| 6,589,028 B1 | 7/2003 | Eckerbom et al. |
| 6,592,542 B2 | 7/2003 | Childers et al. |
| 6,595,948 B2 | 7/2003 | Suzuki et al. |
| 6,603,229 B1 | 8/2003 | Toye, IV |
| 6,604,908 B1 | 8/2003 | Bryant et al. |
| 6,644,930 B1 | 11/2003 | Kuismanen |
| 6,645,166 B2 | 11/2003 | Scheunert et al. |
| 6,645,177 B1 | 11/2003 | Shearn |
| 6,648,861 B2 | 11/2003 | Platt et al. |
| 6,663,355 B2 | 12/2003 | Kubo et al. |
| 6,663,359 B2 | 12/2003 | Gray |
| 6,670,323 B1 | 12/2003 | Looker et al. |
| 6,672,841 B1 | 1/2004 | Herklotz et al. |
| 6,695,593 B1 | 2/2004 | Steck et al. |
| 6,695,803 B1 | 2/2004 | Robinson et al. |
| 6,699,966 B1 | 3/2004 | Singh et al. |
| 6,709,417 B1 | 3/2004 | Houle et al. |
| 6,716,004 B2 | 4/2004 | Vandlik et al. |
| 6,723,062 B1 | 4/2004 | Westberg et al. |

(56) References Cited

U.S. PATENT DOCUMENTS

| | | |
|---|---|---|
| 6,725,726 B1 | 4/2004 | Adolfs et al. |
| 6,726,656 B2 | 4/2004 | Kamen et al. |
| 6,730,055 B2 | 5/2004 | Bainbridge et al. |
| 6,743,201 B1 | 6/2004 | Donig et al. |
| 6,746,514 B2 | 6/2004 | Bedingfield et al. |
| 6,746,637 B1 | 6/2004 | Huss et al. |
| 6,749,403 B2 | 6/2004 | Bryant et al. |
| 6,752,172 B2 | 6/2004 | Lauer |
| 6,752,599 B2 | 6/2004 | Park |
| 6,755,801 B2 | 6/2004 | Utterberg et al. |
| 6,758,975 B2 | 7/2004 | Peabody et al. |
| 6,759,007 B1 | 7/2004 | Westberg et al. |
| 6,759,014 B2 | 7/2004 | Dales et al. |
| 6,764,460 B2 | 7/2004 | Dolecek et al. |
| 6,764,761 B2 | 7/2004 | Eu et al. |
| 6,768,425 B2 | 7/2004 | Flaherty et al. |
| 6,773,412 B2 | 8/2004 | O'Mahony et al. |
| 6,774,517 B2 | 8/2004 | Kowalski et al. |
| 6,790,014 B2 | 9/2004 | Bowen |
| 6,790,195 B2 | 9/2004 | Steele et al. |
| 6,790,198 B1 | 9/2004 | White et al. |
| 6,796,215 B1 | 9/2004 | Hauser et al. |
| 6,800,054 B2 | 10/2004 | Westberg et al. |
| 6,808,369 B2 | 10/2004 | Gray et al. |
| 6,814,547 B2 | 11/2004 | Childers et al. |
| 6,821,432 B2 | 11/2004 | Metzner |
| 6,824,354 B2 | 11/2004 | Laing |
| 6,828,125 B1 | 12/2004 | Hoffman et al. |
| 6,830,553 B1 | 12/2004 | Burbank et al. |
| 6,845,161 B2 | 1/2005 | Boss |
| 6,846,161 B2 | 1/2005 | Kline et al. |
| 6,852,090 B2 | 2/2005 | Burbank et al. |
| 6,865,981 B2 | 3/2005 | Wiechers et al. |
| 6,869,538 B2 | 3/2005 | Yu et al. |
| 6,872,315 B2 | 3/2005 | Effenhauser et al. |
| 6,877,713 B1 | 4/2005 | Gray et al. |
| 6,889,765 B1 | 5/2005 | Traylor |
| 6,905,479 B1 | 6/2005 | Bouchard et al. |
| 6,923,782 B2 | 8/2005 | O'Mahony et al. |
| 6,929,751 B2 | 8/2005 | Bowman, Jr. et al. |
| 6,935,617 B2 | 8/2005 | Mead et al. |
| 6,939,111 B2 | 9/2005 | Huitt et al. |
| 6,948,918 B2 | 9/2005 | Hansen |
| 6,949,079 B1 | 9/2005 | Westberg et al. |
| 6,953,323 B2 | 10/2005 | Childers et al. |
| 6,957,952 B1 | 10/2005 | Steck et al. |
| 6,971,859 B2 | 12/2005 | Yamamoto et al. |
| 6,973,922 B2 | 12/2005 | Yamada et al. |
| 6,978,798 B2 | 12/2005 | Baarda |
| 6,984,218 B2 | 1/2006 | Nayak et al. |
| 6,998,993 B2 | 2/2006 | Wang et al. |
| 7,008,153 B2 | 3/2006 | Rehn et al. |
| 7,014,605 B2 | 3/2006 | Weatherbee |
| 7,021,148 B2 | 4/2006 | Kuhn et al. |
| 7,029,245 B2 | 4/2006 | Maianti et al. |
| 7,033,539 B2 | 4/2006 | Krensky et al. |
| 7,041,076 B1 | 5/2006 | Westberg et al. |
| 7,044,432 B2 | 5/2006 | Beden et al. |
| 7,049,406 B2 | 5/2006 | Weickert et al. |
| 7,083,719 B2 | 8/2006 | Bowman, Jr. et al. |
| 7,087,036 B2 | 8/2006 | Busby et al. |
| 7,107,837 B2 | 9/2006 | Lauman et al. |
| 7,114,531 B2 | 10/2006 | Silva |
| 7,115,107 B2 | 10/2006 | Delnevo et al. |
| 7,115,228 B2 | 10/2006 | Lundtveit et al. |
| 7,134,849 B1 | 11/2006 | Steck et al. |
| 7,147,613 B2 | 12/2006 | Burbank et al. |
| 7,153,286 B2 | 12/2006 | Busby et al. |
| 7,160,087 B2 | 1/2007 | Fathallah et al. |
| 7,166,231 B2 | 1/2007 | Westberg et al. |
| 7,175,606 B2 | 2/2007 | Bowman, Jr. et al. |
| 7,195,607 B2 | 3/2007 | Westberg et al. |
| 7,198,072 B2 | 4/2007 | Silva |
| 7,211,560 B2 | 5/2007 | Looker et al. |
| 7,232,435 B2 | 6/2007 | Hildebrand et al. |
| 7,236,936 B2 | 6/2007 | White et al. |
| 7,238,164 B2 | 7/2007 | Childers et al. |
| 7,255,680 B1 | 8/2007 | Gharib |
| 7,258,534 B2 | 8/2007 | Fathallah et al. |
| 7,261,559 B2 | 8/2007 | Smith et al. |
| 7,267,661 B2 | 9/2007 | Susi |
| 7,273,465 B2 | 9/2007 | Ash |
| 7,284,966 B2 | 10/2007 | Xu et al. |
| 7,306,578 B2 | 12/2007 | Gray et al. |
| 7,318,819 B2 | 1/2008 | Lee et al. |
| 7,331,935 B2 | 2/2008 | Barere |
| 7,338,469 B2 | 3/2008 | Barker et al. |
| 7,338,472 B2 | 3/2008 | Shearn |
| 7,345,025 B2 | 3/2008 | Symonds et al. |
| 7,347,836 B2 | 3/2008 | Peterson et al. |
| 7,390,311 B2 | 6/2008 | Hildebrand et al. |
| 7,398,183 B2 | 7/2008 | Holland et al. |
| 7,399,637 B2 | 7/2008 | Wright et al. |
| 7,404,809 B2 | 7/2008 | Susi |
| 7,410,475 B2 | 8/2008 | Krensky et al. |
| 7,422,905 B2 | 9/2008 | Clague et al. |
| 7,454,314 B2 | 11/2008 | Holland et al. |
| 7,461,968 B2 | 12/2008 | Demers et al. |
| 7,479,522 B2 | 1/2009 | Zhu |
| 7,481,628 B2 | 1/2009 | Yamamoto et al. |
| 7,490,021 B2 | 2/2009 | Holland et al. |
| 7,500,962 B2 | 3/2009 | Childers et al. |
| 7,503,915 B2 | 3/2009 | Beden et al. |
| 7,517,199 B2 | 4/2009 | Reed et al. |
| 7,517,387 B2 | 4/2009 | Chevallet et al. |
| 7,527,483 B1 | 5/2009 | Glauber |
| 7,553,295 B2 | 6/2009 | Susi |
| 7,554,179 B2 | 6/2009 | Shim et al. |
| 7,556,616 B2 | 7/2009 | Fathallah et al. |
| 7,575,564 B2 | 8/2009 | Childers |
| 7,594,801 B2 | 9/2009 | Udagawa |
| 7,618,948 B2 | 11/2009 | Kaemmerer |
| 7,632,080 B2 | 12/2009 | Tracey et al. |
| 7,645,258 B2 | 1/2010 | White et al. |
| 7,648,627 B2 | 1/2010 | Beden et al. |
| 7,654,976 B2 | 2/2010 | Peterson et al. |
| 7,658,598 B2 | 2/2010 | Reed et al. |
| 7,658,958 B2 | 2/2010 | Hansen |
| 7,662,286 B2 | 2/2010 | Childers et al. |
| 7,699,966 B2 | 4/2010 | Qin et al. |
| 7,705,880 B2 | 4/2010 | Dvir et al. |
| 7,717,682 B2 | 5/2010 | Orr |
| 7,766,055 B2 | 8/2010 | Unger et al. |
| 7,776,006 B2 | 8/2010 | Childers et al. |
| 7,789,849 B2 | 9/2010 | Busby et al. |
| 7,794,141 B2 | 9/2010 | Perry et al. |
| 7,801,097 B2 | 9/2010 | Bahr et al. |
| 7,811,067 B2 | 10/2010 | Dietzsch et al. |
| 7,815,595 B2 | 10/2010 | Busby et al. |
| 7,662,133 B2 | 12/2010 | Scarborough et al. |
| 7,901,376 B2 | 3/2011 | Steck et al. |
| 7,909,795 B2 | 3/2011 | Childers et al. |
| 7,935,074 B2 | 5/2011 | Plahey et al. |
| 7,981,280 B2 | 7/2011 | Carr et al. |
| 7,998,101 B2 | 8/2011 | Ash |
| 8,038,640 B2 | 10/2011 | Orr |
| 8,047,815 B2 | 11/2011 | Savard et al. |
| 8,066,671 B2 | 11/2011 | Busby et al. |
| 8,075,526 B2 | 12/2011 | Busby et al. |
| 8,142,397 B2 | 3/2012 | Patzer |
| 8,142,653 B2 | 3/2012 | Beden et al. |
| 8,192,401 B2 | 6/2012 | Morris et al. |
| 8,197,231 B2 | 6/2012 | Orr |
| 8,197,439 B2 | 6/2012 | Wang et al. |
| 8,206,338 B2 | 6/2012 | Childers et al. |
| 8,292,594 B2 | 10/2012 | Tracey et al. |
| 8,292,600 B2 | 10/2012 | Reed et al. |
| 8,317,492 B2 | 11/2012 | Demers et al. |
| 8,360,750 B2 | 1/2013 | Ferk et al. |
| 8,366,921 B2 | 2/2013 | Beden et al. |
| 8,377,293 B2 | 2/2013 | Beden et al. |
| 8,409,441 B2 | 4/2013 | Wilt |
| 8,435,408 B2 | 5/2013 | Beden et al. |
| 8,454,324 B2 | 6/2013 | Grapes |

(56) References Cited

U.S. PATENT DOCUMENTS

| | | |
|---|---|---|
| 8,512,553 B2 | 8/2013 | Cicchello et al. |
| 8,556,225 B2 | 10/2013 | Gray |
| 8,562,834 B2 | 10/2013 | Kamen et al. |
| 8,721,879 B2 | 5/2014 | van der Merwe et al. |
| 8,721,883 B2 | 5/2014 | Lauer |
| 8,926,835 B2 | 1/2015 | Beden et al. |
| 8,932,032 B2 | 1/2015 | Orr |
| 8,986,254 B2 | 3/2015 | Morris et al. |
| 9,011,114 B2 | 4/2015 | Farrell et al. |
| 9,101,709 B2 | 8/2015 | Beden et al. |
| 9,180,240 B2 | 11/2015 | Farrell et al. |
| 9,421,314 B2 | 8/2016 | Plahey et al. |
| 9,500,188 B2 | 11/2016 | Ly et al. |
| 9,610,392 B2 | 4/2017 | Farrell et al. |
| 9,624,915 B2 | 4/2017 | Medina |
| 9,827,359 B2 | 11/2017 | Beden et al. |
| 10,143,791 B2 | 12/2018 | Farrell et al. |
| 10,463,777 B2 | 11/2019 | Farrell et al. |
| 10,471,194 B2 | 11/2019 | Beden et al. |
| 10,507,276 B2 | 12/2019 | Plahey et al. |
| 10,578,098 B2 | 3/2020 | Orr |
| 10,590,924 B2 | 3/2020 | Orr |
| 10,670,005 B2 | 6/2020 | Orr |
| 2001/0034502 A1 | 10/2001 | Moberg |
| 2001/0037763 A1 | 11/2001 | Deguchi et al. |
| 2001/0038796 A1 | 11/2001 | Schluecker |
| 2001/0043450 A1 | 11/2001 | Seale et al. |
| 2002/0045851 A1 | 4/2002 | Suzuki et al. |
| 2002/0048581 A1 | 4/2002 | King |
| 2002/0062109 A1 | 5/2002 | Lauer |
| 2002/0072718 A1 | 6/2002 | Brugger et al. |
| 2002/0098097 A1 | 7/2002 | Singh |
| 2002/0107474 A1 | 8/2002 | Noack |
| 2002/0147423 A1 | 10/2002 | Burbank et al. |
| 2003/0000876 A1 | 1/2003 | Kawaguchi |
| 2003/0018395 A1 | 1/2003 | Crnkovich et al. |
| 2003/0028144 A1 | 2/2003 | Duchon et al. |
| 2003/0029451 A1 | 2/2003 | Blair et al. |
| 2003/0042181 A1 | 3/2003 | Metzner |
| 2003/0045772 A1 | 3/2003 | Reich et al. |
| 2003/0100882 A1 | 5/2003 | Beden et al. |
| 2003/0136189 A1 | 7/2003 | Lauman et al. |
| 2003/0138349 A1 | 7/2003 | Robinson et al. |
| 2003/0194332 A1 | 10/2003 | Jahn et al. |
| 2003/0200812 A1 | 10/2003 | Kuhn et al. |
| 2003/0204162 A1 | 10/2003 | Childers et al. |
| 2003/0217957 A1 | 11/2003 | Bowman et al. |
| 2003/0217961 A1 | 11/2003 | Hopping |
| 2003/0217962 A1 | 11/2003 | Childers et al. |
| 2003/0217975 A1 | 11/2003 | Yu et al. |
| 2003/0218623 A1 | 11/2003 | Krensky et al. |
| 2003/0220599 A1 | 11/2003 | Lundtveit et al. |
| 2003/0220605 A1 | 11/2003 | Bowman et al. |
| 2003/0220607 A1 | 11/2003 | Busby et al. |
| 2003/0220608 A1 | 11/2003 | Huitt et al. |
| 2003/0220609 A1 | 11/2003 | Childers et al. |
| 2003/0220627 A1 | 11/2003 | Distler et al. |
| 2004/0001766 A1 | 1/2004 | Maianti et al. |
| 2004/0010223 A1 | 1/2004 | Busby et al. |
| 2004/0019313 A1 | 1/2004 | Childers et al. |
| 2004/0019320 A1 | 1/2004 | Childers et al. |
| 2004/0031756 A1 | 2/2004 | Suzuki et al. |
| 2004/0064080 A1 | 4/2004 | Cruz et al. |
| 2004/0067161 A1 | 4/2004 | Axelsson |
| 2004/0067171 A1 | 4/2004 | Icke et al. |
| 2004/0082903 A1 | 4/2004 | Micheli |
| 2004/0084647 A1 | 5/2004 | Beden et al. |
| 2004/0086397 A1 | 5/2004 | Bowen |
| 2004/0109769 A1 | 6/2004 | Jahn et al. |
| 2004/0115068 A1 | 6/2004 | Hansen et al. |
| 2004/0135078 A1 | 7/2004 | Mandro et al. |
| 2004/0136843 A1 | 7/2004 | Jahn et al. |
| 2004/0156745 A1 | 8/2004 | Vandlik et al. |
| 2004/0195190 A1 | 10/2004 | Min et al. |
| 2004/0238416 A1 | 12/2004 | Burbank et al. |
| 2005/0054968 A1 | 3/2005 | Giannella |
| 2005/0074340 A1 | 4/2005 | Xu et al. |
| 2005/0100450 A1 | 5/2005 | Bryant et al. |
| 2005/0118041 A1 | 6/2005 | Yamamoto et al. |
| 2005/0126998 A1 | 6/2005 | Childers |
| 2005/0139002 A1 | 6/2005 | Onishi |
| 2005/0197612 A1 | 9/2005 | Levin et al. |
| 2005/0230292 A1 | 10/2005 | Beden et al. |
| 2005/0234384 A1 | 10/2005 | Westberg et al. |
| 2006/0002823 A1 | 1/2006 | Feldstein |
| 2006/0045766 A1 | 3/2006 | Harttig et al. |
| 2006/0079766 A1 | 4/2006 | Neer et al. |
| 2006/0079826 A1 | 4/2006 | Beden et al. |
| 2006/0161092 A1 | 7/2006 | Westberg et al. |
| 2006/0195064 A1 | 8/2006 | Plahey et al. |
| 2006/0261526 A1 | 11/2006 | Bantle et al. |
| 2007/0040454 A1 | 2/2007 | Freudenberger et al. |
| 2007/0077156 A1 | 4/2007 | Orr |
| 2007/0100873 A1 | 5/2007 | Yako et al. |
| 2007/0112297 A1 | 5/2007 | Plahey et al. |
| 2007/0122291 A1 | 5/2007 | Okumura et al. |
| 2007/0140873 A1 | 6/2007 | Grapes |
| 2007/0149913 A1 | 6/2007 | Busby et al. |
| 2007/0193940 A1 | 8/2007 | Duchamp et al. |
| 2007/0201993 A1 | 8/2007 | Terentiev et al. |
| 2007/0213651 A1 | 9/2007 | Busby et al. |
| 2007/0213653 A1 | 9/2007 | Childers et al. |
| 2007/0269340 A1 | 11/2007 | Dannenmaier et al. |
| 2007/0278155 A1 | 12/2007 | Lo et al. |
| 2008/0015493 A1 | 1/2008 | Childers et al. |
| 2008/0033346 A1 | 2/2008 | Childers et al. |
| 2008/0063543 A1 | 3/2008 | Xu et al. |
| 2008/0077068 A1 | 3/2008 | Orr |
| 2008/0103429 A1 | 5/2008 | Shang et al. |
| 2008/0125693 A1 | 5/2008 | Gavin et al. |
| 2008/0138223 A1 | 6/2008 | Lanigan et al. |
| 2008/0208103 A1 | 8/2008 | Demers et al. |
| 2008/0216898 A1 | 9/2008 | Grant et al. |
| 2008/0240929 A1 | 10/2008 | Kamen et al. |
| 2008/0253912 A1 | 10/2008 | Demers et al. |
| 2009/0004033 A1 | 1/2009 | Demers et al. |
| 2009/0095679 A1 | 4/2009 | Demers et al. |
| 2009/0099498 A1 | 4/2009 | Demers et al. |
| 2009/0137940 A1 | 5/2009 | Orr |
| 2009/0169402 A1 | 7/2009 | Stenberg |
| 2009/0198170 A1 | 8/2009 | Childers |
| 2009/0212248 A1 | 8/2009 | Kozak |
| 2010/0021313 A1 | 1/2010 | Devan et al. |
| 2010/0104458 A1 | 4/2010 | Grapes |
| 2010/0133153 A1 | 6/2010 | Beden et al. |
| 2010/0211044 A1 | 8/2010 | Dacquay et al. |
| 2010/0241062 A1* | 9/2010 | Morris ............... A61M 1/14 604/29 |
| 2010/0286614 A1 | 11/2010 | Ring |
| 2011/0015610 A1 | 1/2011 | Plahey et al. |
| 2011/0020156 A1 | 1/2011 | Van Brunt et al. |
| 2011/0041935 A1 | 2/2011 | Zhou et al. |
| 2011/0092895 A1 | 4/2011 | Yardimci et al. |
| 2011/0125085 A1 | 5/2011 | McGill et al. |
| 2011/0137237 A1 | 6/2011 | Prisco et al. |
| 2011/0152785 A1 | 6/2011 | Chattaraj et al. |
| 2011/0274566 A1 | 11/2011 | Amirouche et al. |
| 2011/0293450 A1 | 12/2011 | Grimes et al. |
| 2011/0303598 A1 | 12/2011 | Lo et al. |
| 2012/0022354 A1 | 1/2012 | Beyer et al. |
| 2012/0061310 A1 | 3/2012 | Beden et al. |
| 2012/0065581 A1 | 3/2012 | Childers et al. |
| 2012/0073432 A1 | 3/2012 | Ingersoll et al. |
| 2012/0123322 A1 | 5/2012 | Scarpaci et al. |
| 2012/0156097 A1 | 6/2012 | Beden et al. |
| 2012/0181225 A1 | 7/2012 | Weis |
| 2012/0181226 A1 | 7/2012 | Lauer |
| 2012/0181231 A1 | 7/2012 | Beden et al. |
| 2012/0209169 A1 | 8/2012 | Morris et al. |
| 2012/0224984 A1 | 9/2012 | Orr |
| 2012/0230844 A1 | 9/2012 | Farrell et al. |
| 2012/0232469 A1 | 9/2012 | Medina |
| 2012/0271226 A1* | 10/2012 | Farrell ............... A61M 1/28 604/29 |

(56) References Cited

U.S. PATENT DOCUMENTS

| | | |
|---|---|---|
| 2012/0308412 A1 | 12/2012 | Rochat |
| 2013/0118961 A1 | 5/2013 | Beden et al. |
| 2013/0118970 A1 | 5/2013 | Beden et al. |
| 2013/0155105 A1 | 6/2013 | Boldyrev et al. |
| 2013/0183170 A1 | 7/2013 | Laermer |
| 2013/0184638 A1 | 7/2013 | Scarpaci et al. |
| 2013/0330208 A1 | 12/2013 | Ly et al. |
| 2013/0331774 A1 | 12/2013 | Farrell et al. |
| 2015/0098846 A1 | 4/2015 | Orr |
| 2015/0165105 A1 | 8/2015 | Beden et al. |
| 2016/0015882 A1 | 1/2016 | Farrell et al. |
| 2016/0331883 A1 | 11/2016 | Plahey et al. |
| 2017/0203023 A1 | 7/2017 | Farrell et al. |
| 2018/0117229 A1 | 5/2018 | Beden et al. |
| 2019/0209768 A1 | 7/2019 | Orr |
| 2019/0209769 A1 | 7/2019 | Orr |
| 2019/0209770 A1 | 7/2019 | Orr |

FOREIGN PATENT DOCUMENTS

| | | |
|---|---|---|
| CN | 200943571 Y | 9/2007 |
| CN | 101678159 A | 3/2010 |
| DE | 2628238 | 1/1978 |
| DE | 2827648 | 1/1979 |
| DE | 3441054 A1 | 5/1985 |
| DE | 4006785 | 9/1990 |
| DE | 4336336 | 5/1994 |
| DE | 19837667 | 3/2000 |
| DE | 19919572 A1 | 11/2000 |
| DE | 10042324 | 2/2002 |
| DE | 10046651 | 4/2002 |
| DE | 19919572 C2 | 4/2002 |
| DE | 10053441 | 5/2002 |
| DE | 10157924 | 5/2002 |
| DE | 69618766 | 8/2002 |
| DE | 10143137 | 4/2003 |
| DE | 102007059239 | 6/2009 |
| EP | 0086731 A2 | 8/1983 |
| EP | 0165751 A2 | 12/1985 |
| EP | 257279 | 3/1988 |
| EP | 0129554 B1 | 12/1988 |
| EP | 0432146 A2 | 6/1991 |
| EP | 314379 | 8/1991 |
| EP | 0484575 A1 | 5/1992 |
| EP | 410125 | 8/1993 |
| EP | 728509 | 8/1996 |
| EP | 848193 | 6/1998 |
| EP | 856321 | 8/1998 |
| EP | 947814 | 10/1999 |
| EP | 956876 | 11/1999 |
| EP | 1055853 A2 | 11/2000 |
| EP | 1072868 A1 | 1/2001 |
| EP | 1126895 A1 | 8/2001 |
| EP | 1353069 A2 | 10/2003 |
| EP | 1529545 | 5/2005 |
| EP | 1259204 B1 | 4/2007 |
| GB | 1483702 | 8/1977 |
| GB | 2036168 A | 6/1980 |
| GB | 1601855 A | 11/1981 |
| GB | 2101232 | 1/1983 |
| GB | 2331796 | 6/1999 |
| JP | 53-139399 A | 12/1978 |
| JP | 55-051977 A | 4/1980 |
| JP | 60-500159 A | 2/1985 |
| JP | 61-008057 A | 1/1986 |
| JP | 63-095063 A | 4/1988 |
| JP | 03-060504 A | 3/1991 |
| JP | 03-088978 A | 4/1991 |
| JP | 396850 | 4/1991 |
| JP | 4191755 | 7/1992 |
| JP | 05-003118 A | 1/1993 |
| JP | 05-037073 A | 2/1993 |
| JP | 6154314 | 6/1994 |
| JP | 6002650 | 11/1994 |
| JP | 8028722 | 2/1996 |
| JP | 09-201412 A | 8/1997 |
| JP | 1068383 | 3/1998 |
| JP | 11-324923 A | 11/1999 |
| JP | 11347115 | 12/1999 |
| JP | 2000070358 | 3/2000 |
| JP | 2000346214 | 12/2000 |
| JP | 2001-504374 A | 4/2001 |
| JP | 2002-506693 A | 3/2002 |
| JP | 2002-113096 A | 4/2002 |
| JP | 2002-119585 A | 4/2002 |
| JP | 2002-527212 A | 8/2002 |
| JP | 2003-524507 A | 8/2003 |
| JP | 2005-526575 A | 9/2005 |
| JP | 2007-120446 A | 5/2007 |
| RU | 2105194 C1 | 2/1998 |
| WO | WO 84/02473 | 7/1984 |
| WO | WO 1986/001115 | 2/1986 |
| WO | 87/03065 A1 | 5/1987 |
| WO | 92/19868 A1 | 11/1992 |
| WO | WO 1994/015660 | 7/1994 |
| WO | WO 9420155 | 9/1994 |
| WO | WO 1996/025064 | 9/1996 |
| WO | WO 1997/016214 | 5/1997 |
| WO | WO 97/37703 | 10/1997 |
| WO | 98/02167 A1 | 1/1998 |
| WO | WO 98/22165 | 5/1998 |
| WO | WO 1998/022167 | 5/1998 |
| WO | 99/10028 A1 | 3/1999 |
| WO | WO 00/23140 | 4/2000 |
| WO | WO 00/33898 | 6/2000 |
| WO | 01/00334 A1 | 1/2001 |
| WO | 01/04584 A1 | 1/2001 |
| WO | 01/17607 A1 | 3/2001 |
| WO | WO 01/17605 | 3/2001 |
| WO | 2001/042758 A2 | 6/2001 |
| WO | 2001/064146 A1 | 9/2001 |
| WO | 01/90334 A2 | 11/2001 |
| WO | 2002/007793 A2 | 1/2002 |
| WO | WO 02/25146 | 3/2002 |
| WO | WO 02/25225 | 3/2002 |
| WO | 2007/013049 A1 | 2/2007 |
| WO | WO 2007/006030 | 6/2007 |
| WO | WO 2009/071069 | 6/2009 |
| WO | WO 2010/128914 | 11/2010 |
| WO | WO 2011/045167 | 4/2011 |

OTHER PUBLICATIONS

Gambro®, "DEHP-free cartridge blood sets," © Nov. 2004, Gambro, Inc., Lakewood, CO, 4 pp.
Gambro®, "Prisma® HF 1000, For Increased Filtration Capacity", © Aug. 2001, Gambro Renal Products, Inc., Lakewood, CO, 2 pp.
Gambro®, "Prisma® M60 and M 100 Pre-Pump Infusion Sets—Introducing: The unique solution that enables Physicians to choose a predilution method that meets the needs of their patients", © 2004, Gambro Inc., Lakewood, CO, 4 pp.
Gambro®, "Prismaflex™ anticipating critical care needs and taking our innovative response . . . to new heights," © 2004, Gambro, Inc., Lakewood, CO, 8 pages.
Glenn Avolio, "Principles of Rotary Optical Encoders," Sensors Journal of Machine Perception, vol. 10, No. 4, pp. 10-18, 1993.
Google definition for Hall Effect Sensor, accessed Jul. 30, 2015.
Hall Sensor Effect—NPL Wayback Mar. 11, 2011. www.movingmagnet.com, Technologies, Magnetic and Hall effect Position Sensors.
Innovative Technologies in Peritoneal Dialysis, Sleep Safe Concept, Oct. 13, 1999 (4 attachments).
International Search Report and Written Opinion for PCT Application No. PCT/US2012/032672, dated Jun. 13, 2012, 13 pages.
International Search Report and Written Opinion, PCT/US2010/041976, dated Dec. 2, 2010.
Liberty Cycler Operator's Manual, 2003-2004.
Manns, Markus et al., "The acu-men: A new device for continuous renal replacement therapy in acute renal failure," Kidney International, vol. 54, pp. 268-274, 1998.
Newton IQ Cycler Operator Manual, Part No. 470203 Rev. F, 2000-2006.

(56) References Cited

OTHER PUBLICATIONS

Notification Concerning Transmittal of International Preliminary Report on Patentability for corresponding PCT Application No. PCT/US2012/032672, dated Oct. 31, 2013, 9 pages.
Operator's Instructions, Fresenius 90/2 Peritoneal Therapy Cycler, Part No. 470016 Rev. B, 1991.
Operator's Manual, Serena, Program Version 3.xx—English, 2002.
Ronco et al., "Evolution of Machines for Automated Peritoneal Dialysis", in Automated Peritoneal Dialysis, Contributions to Nephrology, vol. 129, pp. 142-161, 1999.
Sleep Safe Communicating Therapy, Mar. 1998.
Sleep Safe Kommunizierte Therapie, May 1998.
Sleep Safe Operating Instructions, Jan. 2002.
Sleep Safe Operating Instructions, Software Version 0.5, Apr. 1999.
Sleep Safe Operating Instructions, Software Version 0.9, Part No. 677 805 1; Aug. 2000.
Sleep Safe Operating Instructions, Software Version 1.0, Oct. 2000.
Sleep Safe Technical Manual, Dec. 2001.
Sleep Safe Technical Manual, Part No. 677 807 1, Aug. 2000.
TL™ Pump Brochure, TL Systems Corporation, Apr. 1975.
[No Author Listed], "Air Operated Double Diaphragm Pumps 1/2" Model: Operations and Maintenance Instructions," Graymills, Sep. 2005, 1-20.
[No Author Listed], "Double Diaphragm Pumps: Concept and Theory," Graco, Inc., Form No. 321-048 1/96, 1996, 31 pages.
[No Author Listed], "Operator's Manual: Serena—Program Version 3.xx (English)," Gambro Renal Products, 2001, 162 pages.
apumpstore.com [online], "Operator's Manual 66610X-X-C—1" Diaphragm Pump: 1.1 Ratio (Metallic)," Aug. 24, 1989, revised Oct. 15, 2010, retrieved at URL <https://www.apumpstore.com/documents/literature/aro66610x-xxx-c-en.pdf>, 8 pages.
Cervino et al., "Novel Left Ventricular Assist Systems I and II for Cardiac Recovery: The Driver," Cardiovascular Devices, Texas Heart Institute Journal, Novel LVAS I and II: The Driver, 2005, 32(4):535-540.
European Search Report in European Appln. No. 10011805.8, dated May 11, 2011, 19 pages (with machine translation).
European Search Report in European Appln. No. 10011806.6, dated May 10, 2011, 12 pages (with machine translation).
European Search Report in European Appln. No. 15196981.3, dated Mar. 8, 2016, 5 pages.
Hoerstrup et al., "Functional Living Trileaflet Heart Valves Grown In Vitro," Circulation, Nov. 2000, 102(Suppl. 3):Iii-44-Iii-49, 12 pages.
International Preliminary Report on Patentability in International Appln. No. PCT/EP2003/005377, dated Jan. 30, 2004, 4 pages (with English translation).
International Preliminary Report on Patentability in International Appln. No. PCT/US2010/041976, dated Jan. 26, 2012, 9 pages.
International Search Report in International Appln. No. PCT/EP2003/005377, dated Aug. 21, 2003, 7 pages (with English translation).
Laser et al., "Topical Review A Review of Micropumps," J. Micromech. Microeng., 2004, 14:R35-R64, 31 pages.
Olsson et al., "A valve-less planar fluid pump with two pumps chambers," Sensors and Actuators A: Physical, Mar.-Apr. 1995, 47(1-3):549-556.
Taylor et al., "Simulation of microfluidic pumping in a genomic DNA blood-processing cassette," Journal of Micromechanics and Microengineering, Jan. 2003, 13:201-208, 9 pages.

* cited by examiner

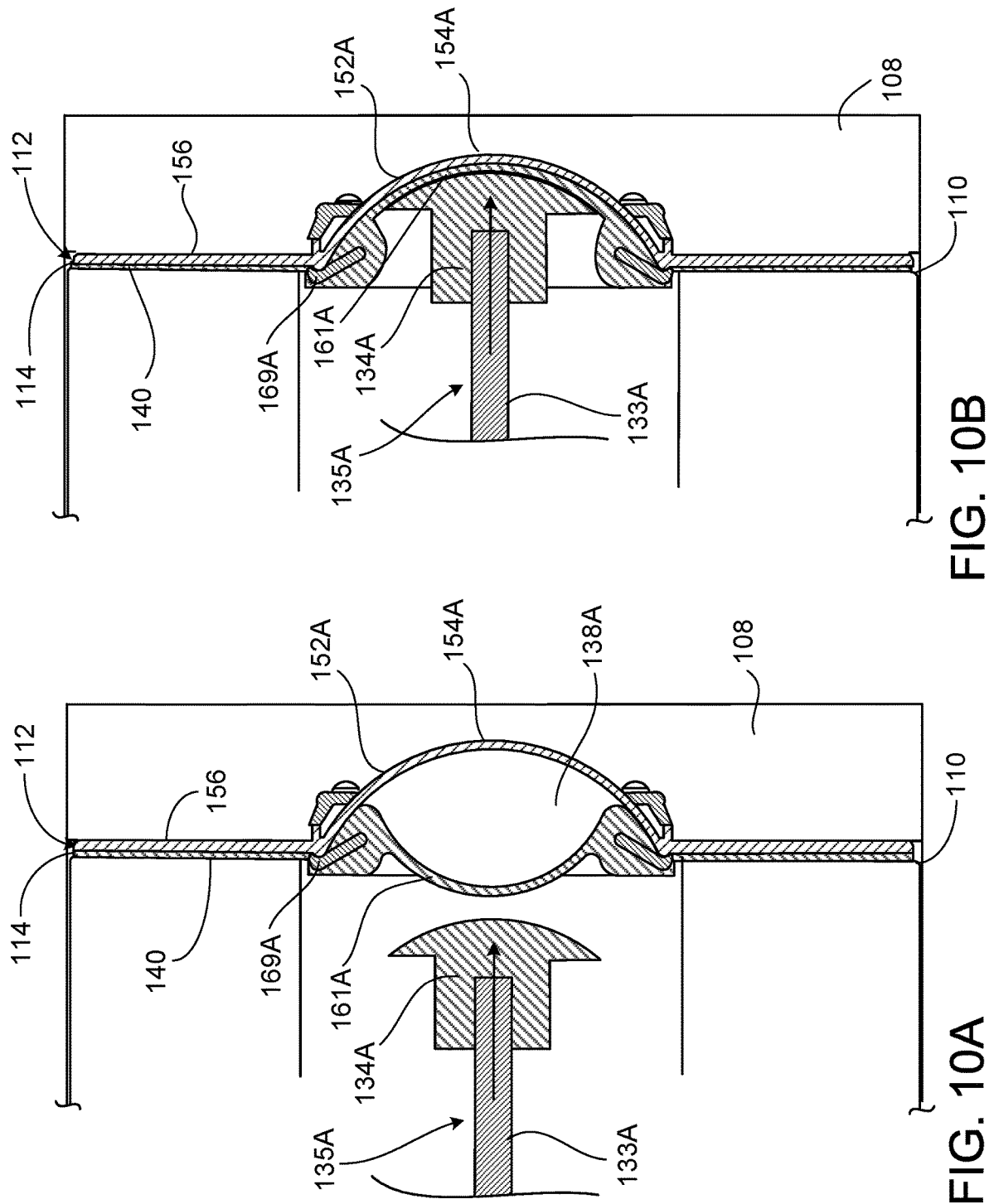

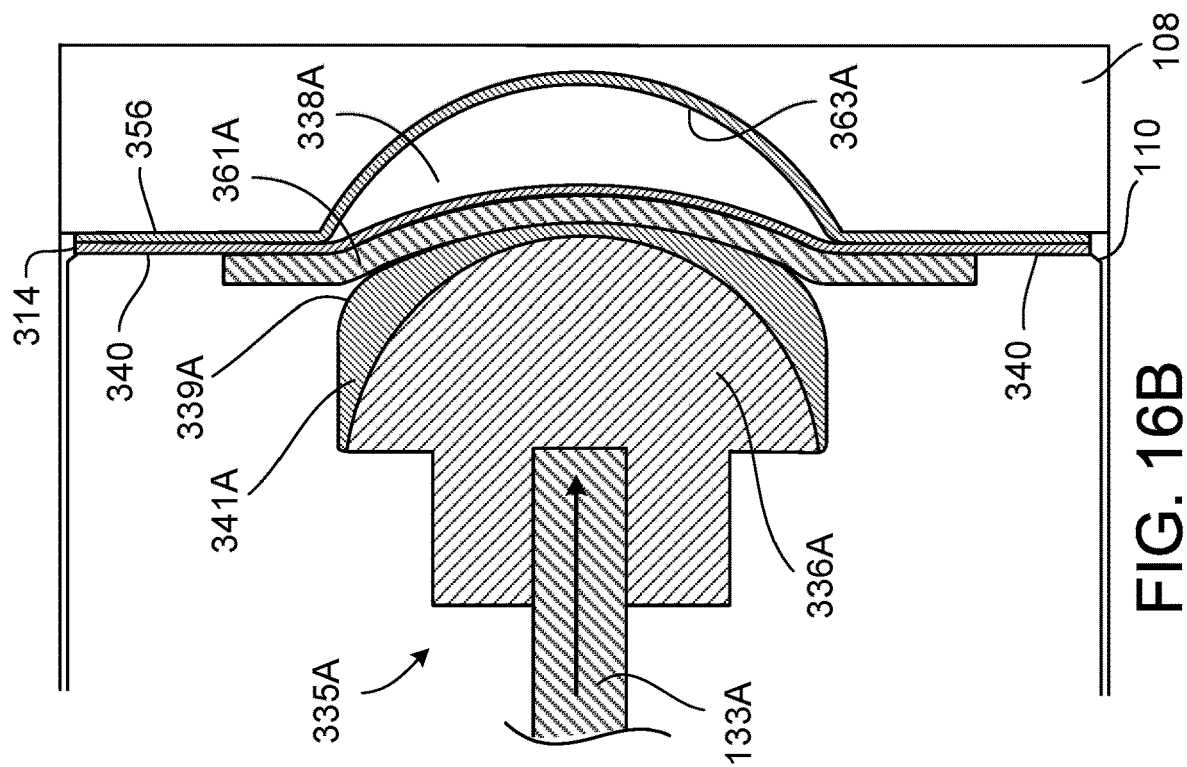
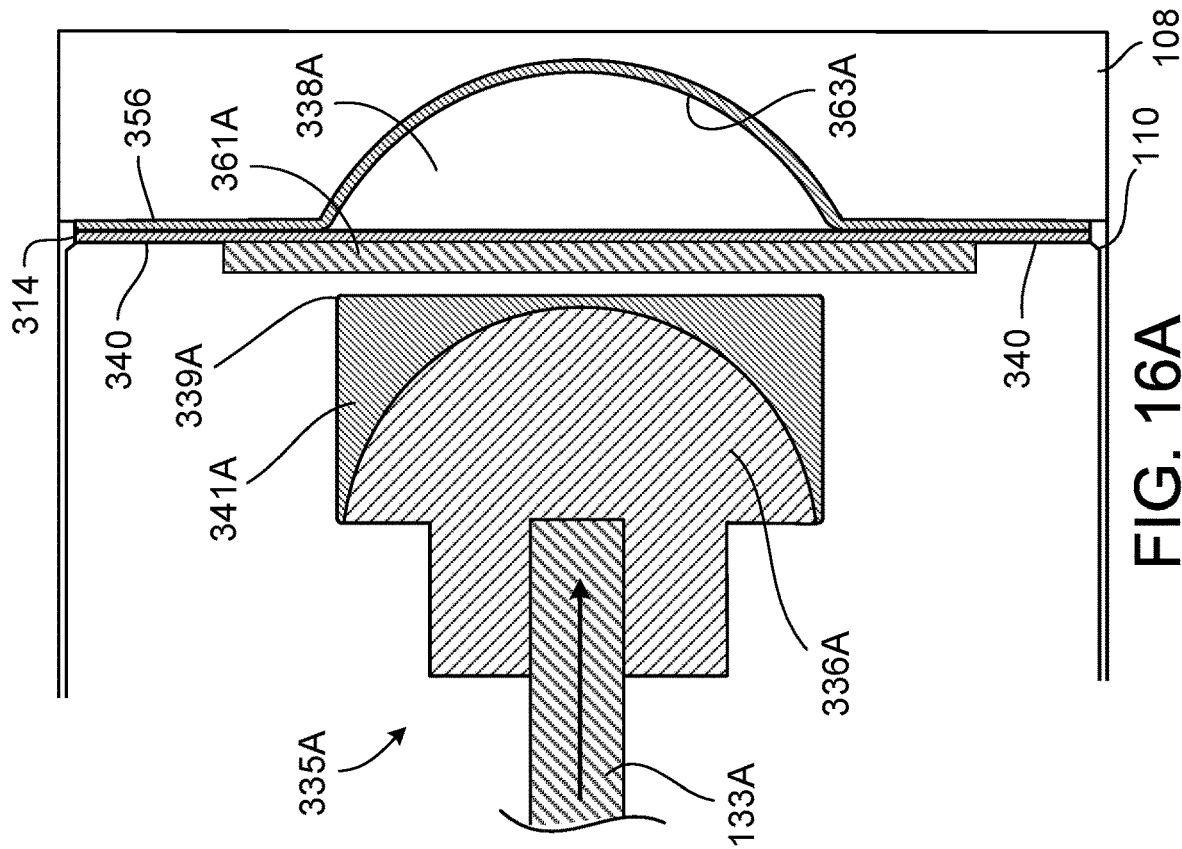
FIG. 16A
FIG. 16B

MEDICAL FLUID CASSETTES AND RELATED SYSTEMS AND METHODS

CROSS REFERENCE TO RELATED APPLICATION

This application is a divisional of and claims priority under 35 U.S.C. § 121 to U.S. application Ser. No. 15/475,342, filed Mar. 31, 2017; which is a divisional of U.S. Ser. No. 13/492,370, filed Jun. 8, 2012, now U.S. Pat. No. 9,610,392. The entire contents of each application is hereby incorporated by reference in its entirety.

TECHNICAL FIELD

This disclosure relates to medical fluid cassettes and related systems and methods.

BACKGROUND

Dialysis is a treatment used to support a patient with insufficient renal function. The two principal dialysis methods are hemodialysis and peritoneal dialysis.

During hemodialysis ("HD"), the patient's blood is passed through a dialyzer of a dialysis machine while also passing a dialysis solution or dialysate through the dialyzer. A semi-permeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

During peritoneal dialysis ("PD"), a patient's peritoneal cavity is periodically infused with dialysis solution or dialysate. The membranous lining of the patient's peritoneum acts as a natural semi-permeable membrane that allows diffusion and osmosis exchanges to take place between the solution and the blood stream. These exchanges across the patient's peritoneum, like the continuous exchange across the dialyzer in HD, result in the removal waste products, including solutes like urea and creatinine, from the blood, and regulate the levels of other substances, such as sodium and water, in the blood.

Many PD machines are designed to automatically infuse, dwell, and drain dialysate to and from the patient's peritoneal cavity. The treatment typically lasts for several hours, often beginning with an initial drain cycle to empty the peritoneal cavity of used or spent dialysate. The sequence then proceeds through the succession of fill, dwell, and drain phases that follow one after the other. Each phase is called a cycle.

SUMMARY

In one aspect of the invention, a medical fluid pumping system includes a medical fluid pumping machine defining a cassette enclosure and including a movable piston. The system further includes a medical fluid cassette configured to be disposed within the cassette enclosure of the medical fluid pumping machine. The medical fluid cassette includes a base having a first region and a second region, a first membrane overlying the first region of the base, and a second membrane overlying the second region of the base. The first membrane cooperates with the first region of the base to form at least one fluid pathway and the second membrane cooperates with the second region of the base to define a fluid pump chamber. The second membrane is more resilient than the first membrane. The cassette is positionable within the cassette enclosure of the medical fluid pumping machine so that the second membrane can be moved toward the base by the piston to decrease a volume of the fluid pump chamber and, upon retraction of the piston, the second membrane can rebound to increase the volume of the pump chamber.

In another aspect of the invention, a medical fluid cassette includes a base having a first region and a second region, a first membrane overlying the first region of the base, and a second membrane overlying the second region of the base. The first membrane cooperates with the first region of the base to form at least one fluid pathway and the second membrane cooperates with the second region of the base to define a fluid pump chamber. The second membrane is more resilient than the first membrane and is configured to rebound away from the base when a force used to press the second membrane toward the base is released.

In an additional aspect of the invention, a medical fluid delivery method includes expelling a medical fluid from a fluid pump chamber defined between a membrane and a recessed region of a base of a medical fluid cassette by using a piston to press the membrane into the recessed region, and then drawing medical fluid into the fluid pump chamber by retracting the piston and allowing the membrane to rebound toward the retracting piston, wherein the membrane is allowed to rebound toward the retracting piston head due to resiliency of the membrane.

In a further aspect of the invention, a medical fluid pumping machine includes a housing that at least partially defines a cassette enclosure configured to receive a medical fluid cassette and a piston that is translatable relative to the housing. The cassette includes a fluid pump chamber defined between a membrane and a base, and the piston includes a piston head having a circumferential region that is configured to move radially inward as the piston head is pressed against the membrane of the cassette to move the membrane toward a base of the cassette.

Implementations can include one or more of the following features.

In some implementations, the second region of the base is a recessed region of the base.

In certain implementations, the first region of the base is a substantially planar region of the base from which a plurality of raised ridges extend.

In some implementations, the second membrane has a greater thickness than the first membrane.

In certain implementations, the first membrane has a thickness of about 0.004 inch to about 0.006 inch, and the second membrane has a thickness of about 0.05 inch to about 0.12 inch.

In some implementations, the first and second membranes are formed of different materials.

In certain implementations, the second membrane is formed of an elastomer.

In some implementations, the second region of the base is a recessed region of the base, and the second membrane is sized to overlie a portion of the base that surrounds the recessed region.

In certain implementations, a fluid-tight seal is formed between a peripheral region of the second membrane and the base.

In some implementations, the second membrane includes a dome-shaped portion.

In certain implementations, the medical fluid cassette further includes a first ring that is secured to the second membrane and compresses the second membrane against the base.

In some implementations, the first ring is fastened to the base.

In certain implementations, the medical fluid pumping system further includes a second ring disposed on a side of the base opposite the second membrane, and the second ring is secured to the first ring in a manner to cause the first ring to compress the second membrane against the base.

In some implementations, the first and second rings are secured to the base by mechanical fasteners.

In certain implementations, the second membrane is attached to the portion of the base that surrounds the recessed region.

In some implementations, the second membrane is welded to the portion of the base that surrounds the recessed region.

In certain implementations, the first membrane defines an aperture that is aligned with the second region of the base, and the second membrane is at least partially disposed within the aperture of the first membrane.

In some implementations, the first membrane covers substantially the entire surface of the base.

In certain implementations, the first membrane is attached to the base in a perimeter region of the base.

In some implementations, the second membrane is attached (e.g., adhesively attached) to a portion of the first membrane that overlies the second region of the base.

In certain implementations, the second membrane overlies substantially the entire surface of the base.

In some implementations, the second membrane includes a plurality of cutouts that are aligned with valve regions of the cassette.

In certain implementations, the second membrane is configured to create a vacuum pressure of about 150 mbar to about 200 mbar within the fluid pump chamber when the second membrane is allowed to rebound after being pressed toward the base (e.g., by the piston).

In some implementations, the piston includes a piston head having a circumferential region that is configured to move radially inward as the piston head is pressed against the second membrane to move the second membrane toward the base.

In certain implementations, the circumferential region of the piston head is formed of an elastomeric material that compresses as the piston head is pressed against the second membrane to move the second membrane toward the base.

In some implementations, the piston head includes a plurality of interleaved segments that move relative to one another to allow the circumferential region of the piston head to collapse as the piston head is pressed against the second membrane to move the second membrane toward the base.

In certain implementations, the interleaved segments are in the form of leaves.

In some implementations, the interleaved segments are spring-loaded to bias the piston head to an expanded position.

In certain implementations, the piston head includes a plurality of telescoping segments that move relative to one another to allow the circumferential region of the piston head to collapse as the piston head is pressed against the second membrane to move the second membrane toward the base.

In some implementations, the telescoping segments are rings.

In certain implementations, the telescoping segments are secured to a spring that biases the piston head to a flat configuration.

In some implementations, at any given time throughout an outward stroke of the piston, an area of a portion of the piston head in contact with the second membrane is substantially equal to an area of the pump chamber in a plane in which the second membrane lies.

In certain implementations, the medical fluid pumping system is a dialysis system (e.g., a peritoneal dialysis system).

In some implementations, the medical fluid cassette is a dialysis fluid cassette (e.g., a peritoneal dialysis fluid cassette).

In certain implementations, the membrane creates a vacuum pressure of about 150 mbar to about 200 mbar within the fluid pump chamber when the membrane is allowed to rebound after being pressed into the recessed region by the piston.

In some implementations, the piston includes a piston head having a circumferential region that is configured to move radially inward as the piston head is pressed against the membrane to press the membrane into the recessed region.

In certain implementations, at any given time throughout the retraction of the piston, an area of a portion of the piston in contact with the membrane is substantially equal to an area of the pump chamber in a plane in which the membrane lies.

In some implementations, the medical fluid is dialysate.

In certain implementations, the circumferential region of the piston head is formed of an elastomeric material that compresses as the piston head is pressed against the membrane to move the membrane toward the base.

In some implementations, the piston head includes a plurality of interleaved segments that move relative to one another to allow the circumferential region of the piston head to collapse as the piston head is pressed against the membrane to move the membrane toward the base.

In certain implementations, the interleaved segments are in the form of leaves.

In some implementations, the interleaved segments are spring-loaded to bias the piston head to an expanded position.

In certain implementations, the piston head includes a plurality of telescoping segments that move relative to one another to allow the circumferential region of the piston head to collapse as the piston head is pressed against the membrane to move the membrane toward the base.

In some implementations, the telescoping segments are rings.

In certain implementations, the telescoping segments are secured to a spring that biases the piston head to a flat configuration.

In some implementations, at any given time throughout an outward stroke of the piston, an area of a portion of the piston head in contact with the membrane is substantially equal to an area of the pump chamber in a plane in which the membrane lies.

In certain implementations, the medical fluid pumping machine further includes a door secured to the housing, and the door and the housing cooperate to define the cassette enclosure when the door is closed.

Implementations can include one or more of the following advantages.

In some implementations, the membrane, after being pressed toward the region of the base that partially defines the pump chamber, rebounds as a result of its own internal forces (or self-expands) with sufficient force to create suction within the pump chamber that draws fluid into the pump chamber. Thus, fluid can be drawn into the pump chamber without requiring the membrane to be coupled (e.g., via vacuum pressure, adhesive, or mechanical fasteners) to the piston of the medical fluid pumping machine.

In certain implementations, the design of the membrane allows the medical fluid pumping system to be operated without permanently deforming (e.g., stretching) the membrane. For example, the membrane can be thicker than many conventional cassette membranes and/or can have a dome-shaped region that allows the membrane to be fully deflected into the recessed region of the base and then to rebound without permanent deformation. As a result, the pumping volume accuracy of the system can be improved as compared to conventional systems that utilize cassettes having thinner, flat membranes that permanently deform or stretch during use.

In some implementations, the portions of the membrane overlying the pump chamber are substantially prevented from bulging outward (i.e., away from the base of the cassette) during the fluid pumping process. In some implementations, for example, the membrane is thicker than many conventional cassette membranes. This construction enables the portions of the membrane that overlie the pump chamber but are not in contact with the piston as the piston is advanced toward the base of the cassette to withstand the increased fluid pressure within the pump chamber without bulging outward.

In certain implementations, a piston head of the piston is designed so that the area of the piston head that is in contact with the membrane overlying the pump chamber throughout an outward stroke of the piston (i.e., as the piston is advanced towards the cassette base) is substantially equal to the area of the pump chamber in the plane in which the membrane lies. For example, the piston head can have a circumferential region that is compressible or collapsible such that the pressure applied to the piston head by the membrane as the piston head is advanced (and as the area of the pump chamber gradually decreases) causes the circumferential region to compress or collapse. This piston head design can prevent or significantly reduce outward bulging of the cassette membrane as a result of increased fluid pressure in the pump chamber because the piston head contacts and resists outward bulging in those areas of the membrane that tend to bulge outwardly in many convention medical fluid cassettes.

Other aspects, features, and advantages will be apparent from the description and drawings, and from the claims.

DESCRIPTION OF DRAWINGS

FIGS. 10A-10C are diagrammatic cross-sectional views of the PD system of FIG. 1 with the PD cassette in the cassette compartment of the PD cycler, during different phases of operation.

FIGS. 16A-16D are diagrammatic cross-sectional views of the PD cassette of FIG. 14 in the cassette compartment of a PD cycler equipped with the piston of FIG. 15, during different phases of operation.

DETAILED DESCRIPTION

In certain aspects of the invention, a medical fluid cassette (e.g., a dialysis fluid cassette) includes a relatively thick membrane that overlies a recessed region of a base to form a fluid pump chamber. During use, a piston of a medical fluid pumping machine (e.g., a dialysis machine) presses against the membrane to move the membrane toward the base and expel fluid from the fluid pump chamber. In some cases, the piston has a piston head with a circumferential region that compresses or collapses as the piston moves the membrane into the recessed region of the base. Such a configuration can help to ensure that uniform pressure is applied to the membrane by the piston head throughout the outward stroke of the piston. The piston is subsequently retracted and the membrane rebounds under its own force (or self-expands) causing fluid to be drawn into the fluid pump chamber. Examples of medical fluid cassettes and medical fluid pumping machines are described below.

Figure 1:
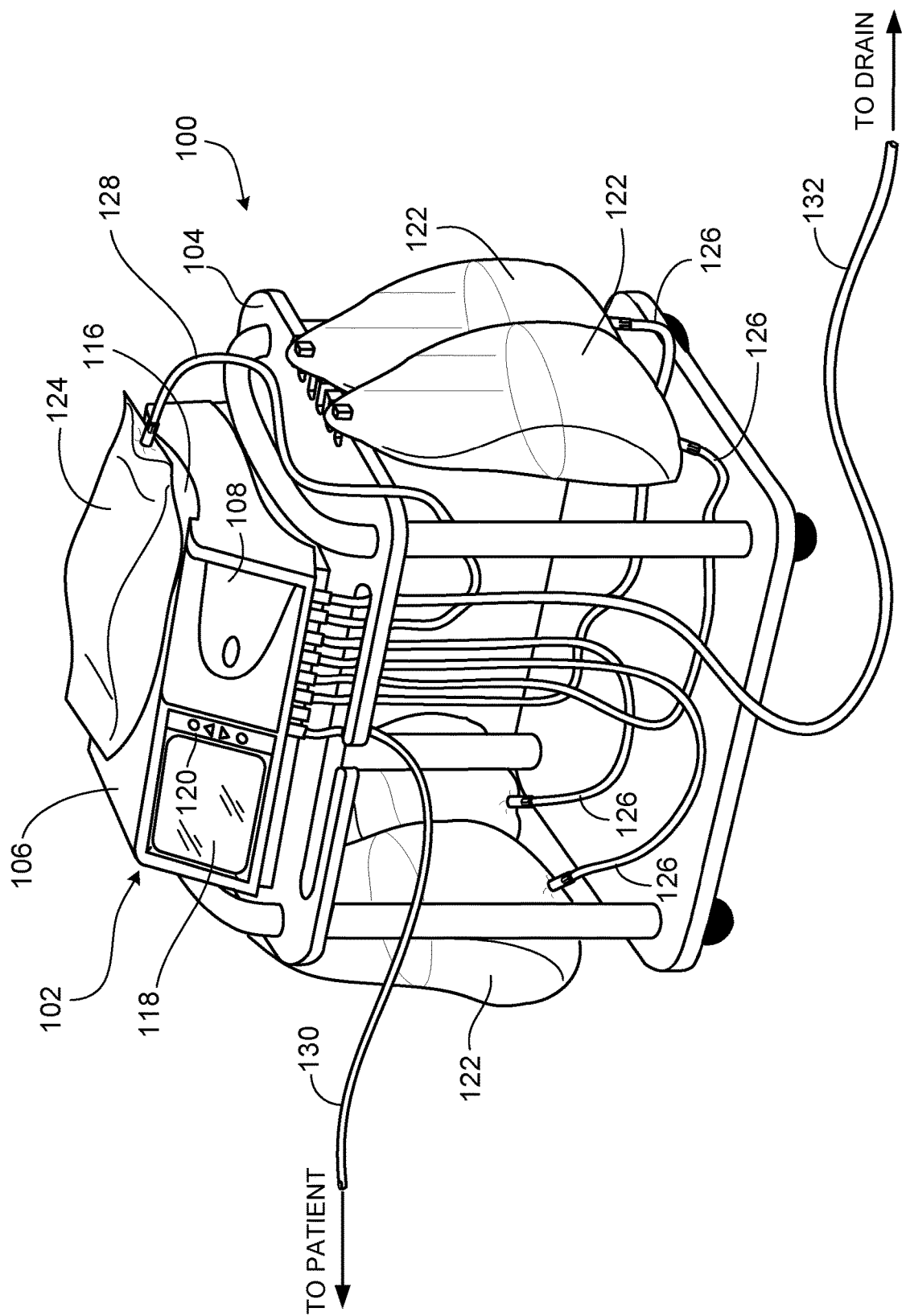
FIG. 1 is a perspective view of a peritoneal dialysis ("PD") system that includes a PD cycler positioned atop a portable cart.
Figure 2:
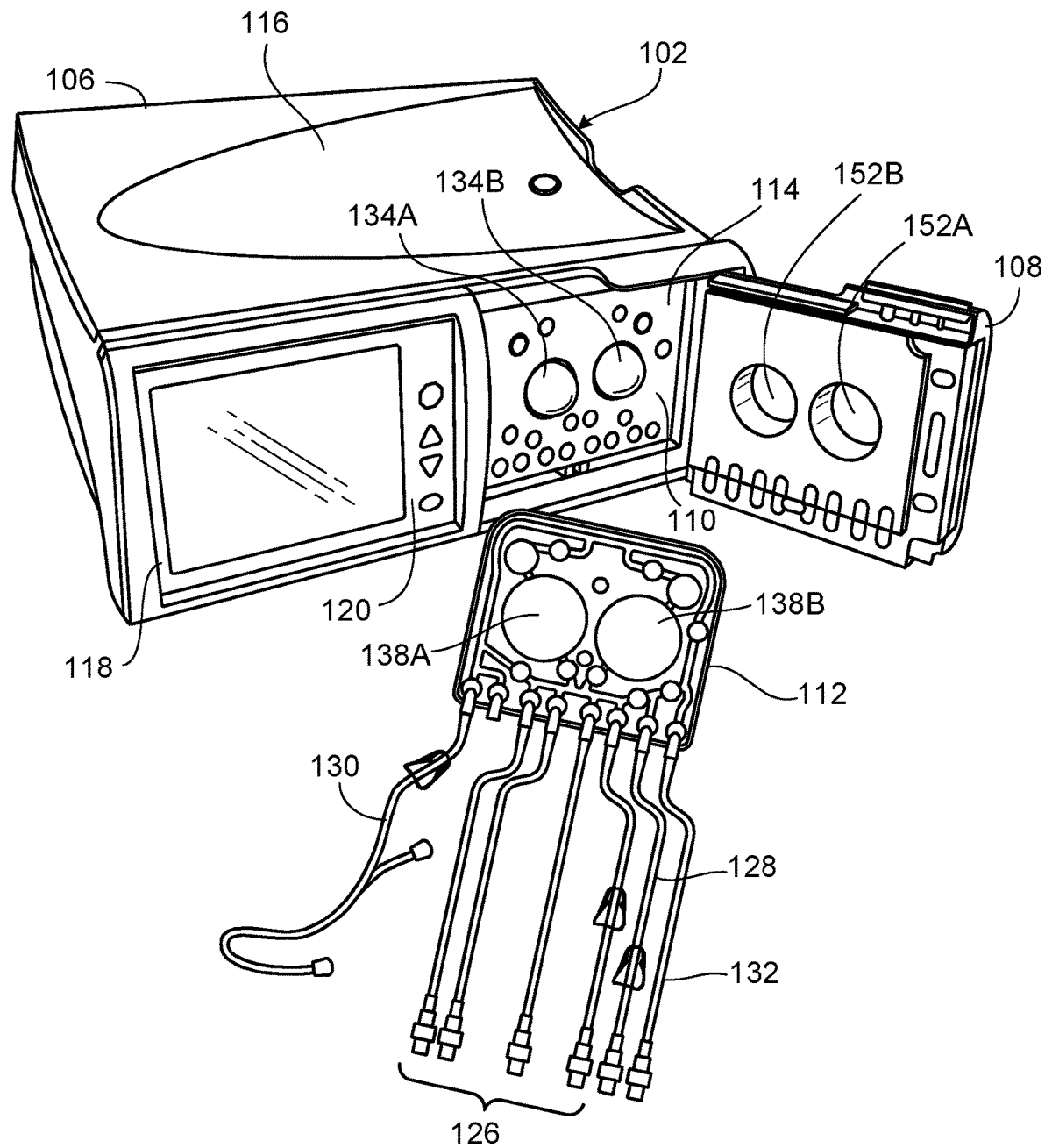
FIG. 2 is a perspective view of the PD cycler and PD cassette of the PD system of FIG. 1. A door of the PD cycler is in the open position to show the inner surfaces of the PD cycler that interface with the PD cassette during use.

Referring to FIG. 1, a peritoneal dialysis ("PD") system 100 includes a PD cycler (also referred to as a PD machine) 102 seated on a cart 104. Referring also to FIG. 2, the PD cycler 102 includes a housing 106, a door 108, and a cassette interface 110 that mates with a disposable PD cassette 112 when the cassette 112 is disposed within a cassette compartment 114 formed between the cassette interface 110 and the closed door 108. A heater tray 116 is positioned on top of the housing 106. The heater tray 116 is sized and shaped to accommodate a bag of dialysis solution (e.g., a 5 liter bag of dialysis solution). The PD cycler 102 also includes a touch screen 118 and additional control buttons 120 that can be operated by a user (e.g., a patient) to allow, for example, set-up, initiation, and/or termination of a PD treatment.

Dialysis solution bags 122 are suspended from fingers on the sides of the cart 104, and a heater bag 124 is positioned on the heater tray 116. The dialysis solution bags 122 and the heater bag 124 are connected to the cassette 112 via dialysis solution bag lines 126 and a heater bag line 128, respectively. The dialysis solution bag lines 126 can be used to pass dialysis solution from dialysis solution bags 122 to the cassette 112 during use, and the heater bag line 128 can be used to pass dialysis solution back and forth between the cassette 112 and the heater bag 124 during use. In addition, a patient line 130 and a drain line 132 are connected to the cassette 112. The patient line 130 can be connected to a patient's abdomen via a catheter and can be used to pass dialysis solution back and forth between the cassette 112 and the patient during use. The drain line 132 can be connected to a drain or drain receptacle and can be used to pass dialysis solution from the cassette 112 to the drain or drain receptacle during use.

Figure 3:
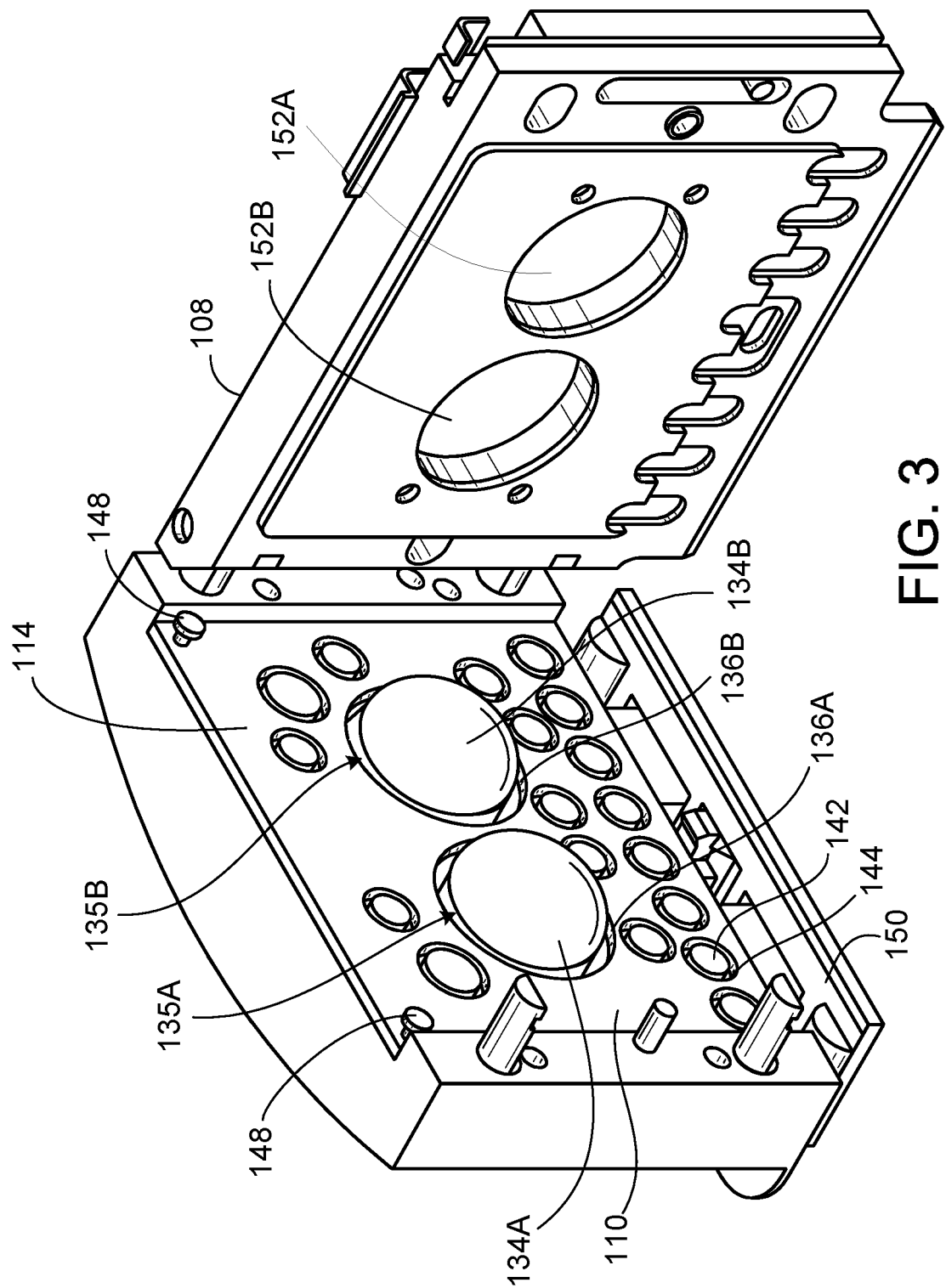
FIG. 3 is a perspective view of an open cassette compartment of the PD cycler of FIGS. 1 and 2.

FIG. 3 shows a more detailed view of the cassette interface 110 and the door 108 of the PD cycler 102. As shown, the PD cycler 102 includes pistons 135A, 135B with substantially hemispherical piston heads 134A, 134B that can be axially moved within piston access ports 136A, 136B formed in the cassette interface 110. The piston heads 134A, 134B can be formed of any of various different polymers, metals, and/or alloys. In some implementations, the piston heads 134A, 134B are made of polyoxymethylene (marketed under the trade name Delrin available from Dupont of Wilmington, Del.). The hemispherical shape of the piston heads 134A, 134B can be achieved using any of various different techniques, including machining techniques molding techniques, and/or casting techniques.

The pistons 135A, 135B include piston shafts 133A, 133B (shown in FIGS. 10A-10C) that are coupled to motors that can be operated to move the piston heads 134A, 134B axially inward and outward within the piston access ports 136A, 136B. As discussed below, when the cassette 112 (shown in FIGS. 2 and 4-8) is positioned within the cassette compartment 114 with the door 108 closed, the piston heads 134A, 134B of the PD cycler 102 align with pump chambers 138A, 138B of the cassette 112. As a result, the piston heads 134A, 134B can be moved in the direction of the cassette 112 to force pumping membranes 161A, 161B towards a rigid base 156 of the cassette 112, causing the volume defined by the pump chambers 138A, 138B to decrease and forcing dialysis solution out of the pump chambers 138A, 138B. The piston heads 134A, 134B can also be retracted away from the cassette 112 and out of the volume defined by the pump chambers 138A, 138B. As discussed in greater detail below, the pumping membranes 161A, 161B are resilient members that automatically rebound (or self-expand) toward the piston heads 134A, 134B as the piston heads 134A, 134B are retracted. As a result, the volume defined by the pump chambers 138A, 138B increases and dialysis solution is drawn into the pump chambers 138A, 138B as the piston heads 134A, 134B retract and the pumping membranes 161A, 161B are allowed to rebound.

Referring again to FIG. 3, the PD cycler 102 also includes multiple inflatable members 142 positioned within inflatable member access ports 144 in the cassette interface 110. The inflatable members 142 align with depressible dome regions 146 of the cassette 112 when the cassette 112 is positioned within the cassette compartment 114. While only one of the inflatable members 142 is labeled in FIG. 3, it should be understood that the PD cycler 102 includes an inflatable member associated with each of the depressible dome regions 146 of the cassette 112 (shown in FIG. 5). The inflatable members 142 act as valves to direct dialysis solution through the cassette 112 in a desired manner during use. In particular, the inflatable members 142 bulge outward beyond the surface of the cassette interface 110 and into contact with the depressible dome regions 146 of the cassette 112 when inflated, and retract into the inflatable member access ports 144 and out of contact with the cassette 112 when deflated. By inflating some of the inflatable members 142 and deflating other inflatable members 142, certain fluid flow paths within the cassette 112 will be blocked off while other fluid flow paths within the cassette 112 will remain open. Thus, dialysis solution can be pumped through the cassette 112 by actuating the piston heads 134A, 134B, and can be guided along desired flow paths within the cassette 112 by selectively inflating and deflating the inflatable members 142.

Still referring to FIG. 3, locating pins 148 extend from the cassette interface 110. When the door 108 is in the open position, the cassette 112 can be loaded onto the cassette interface 110 by positioning the top portion of the cassette 112 under the locating pins 148 and pushing the bottom portion of the cassette 112 toward the cassette interface 110. The cassette 112 is dimensioned to remain securely positioned between the locating pins 148 and a lower ledge 150 extending from the cassette interface 110 to allow the door 108 to be closed over the cassette 112. The locating pins 148 help to ensure that the pump chambers 138A, 138B of the cassette 112 are aligned with the piston heads 134A, 134B when the cassette 112 is positioned in the cassette compartment 114 between the closed door 108 and the cassette interface 110.

The door 108, as shown in FIG. 3, defines recesses 152A, 152B that substantially align with the piston heads 134A, 134B when the door 108 is in the closed position. When the cassette 112 is positioned within the cassette compartment 114, hollow projections 154A, 154B of the cassette 112 (shown in FIGS. 6-8), inner surfaces of which cooperate with the membrane 140 to form the pump chambers 138A, 138B, fit within the recesses 152A, 152B. The door 108 further includes a pad that can be inflated during use to compress the cassette 112 between the door 108 and the cassette interface 110. With the pad inflated, the portions of the door 108 forming the recesses 152A, 152B support the projections 154A, 154B and the planar surface of the door 108 supports the other regions of the cassette 112. The door 108 can counteract the forces applied by the piston heads 134A, 134B and the inflatable members 142 and thus allows the piston heads 134A, 134B to depress the portions of the membrane 140 overlying the pump chambers 138A, 138B and similarly allows the inflatable members 142 to actuate the depressible dome regions 146 on the cassette 112.

The PD cycler 102 includes various other features not described in detail herein. Further details regarding the PD cycler 102 and its various components can be found in U.S. Patent Application Publication No. 2007/0112297, which is incorporated by reference herein.

Figure 4:
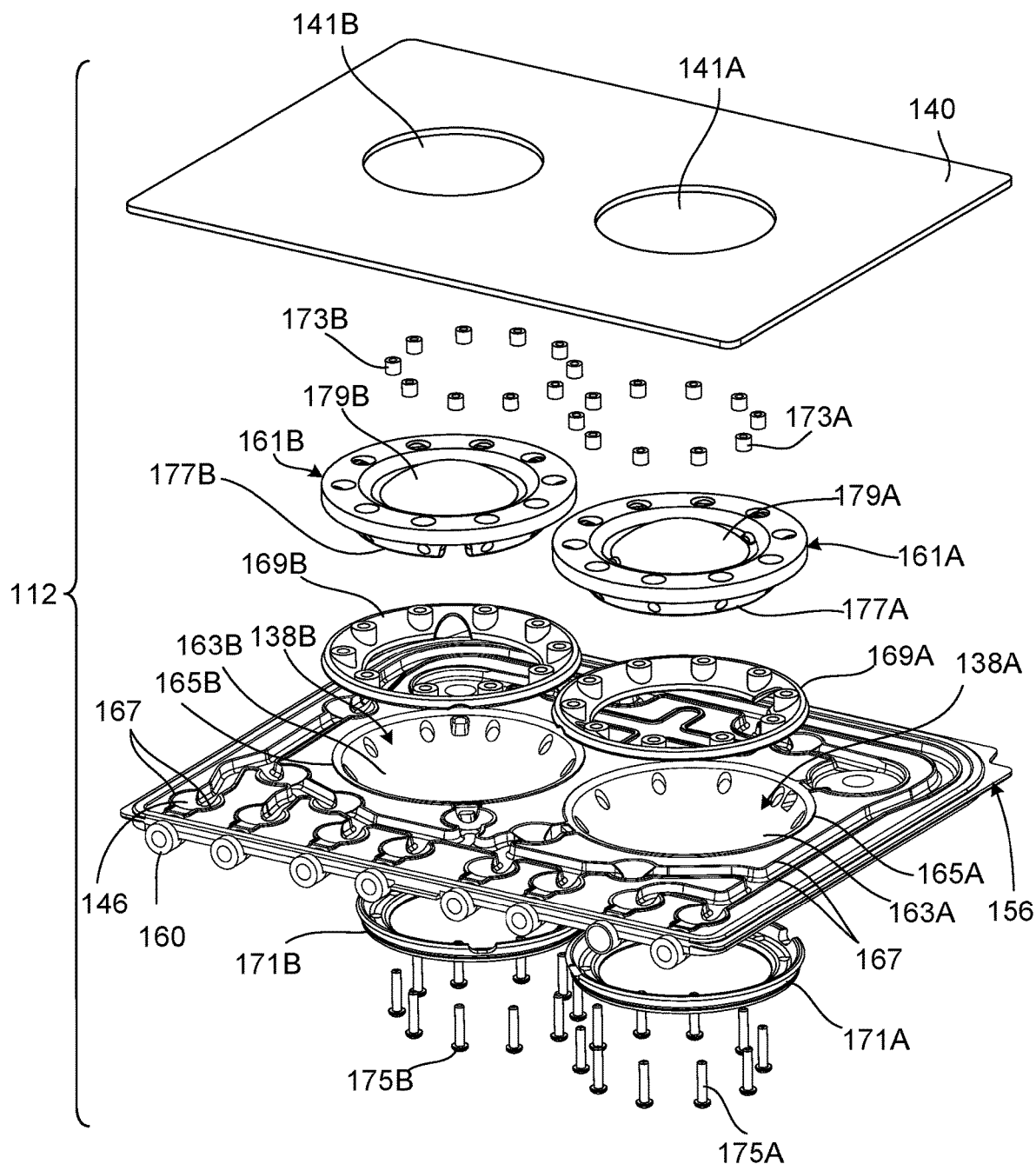
FIG. 4 is an exploded, perspective view of the PD cassette of the PD system of FIG. 1.
Figure 5:
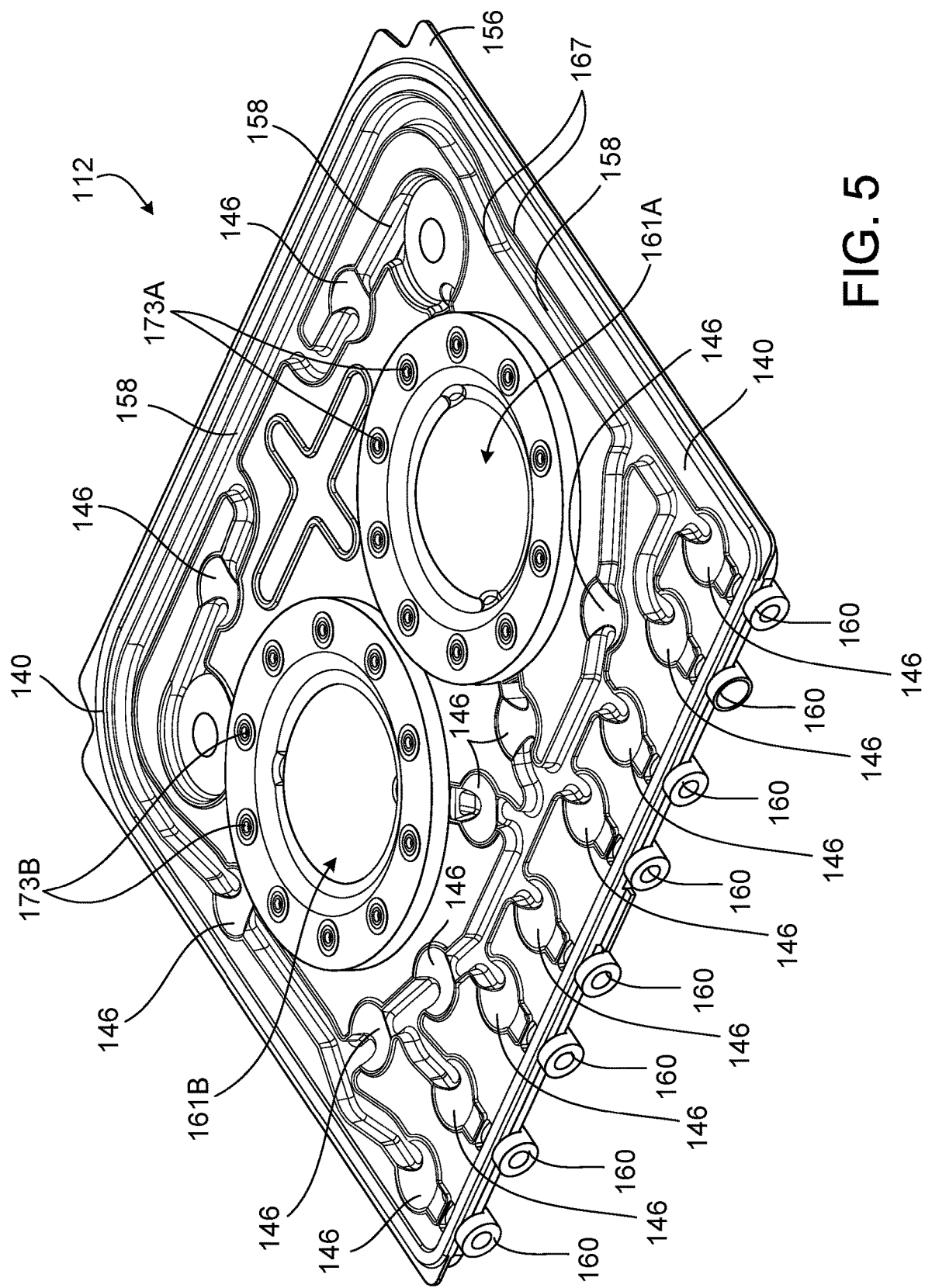
FIG. 5 is a perspective view of the PD cassette, from a membrane side of the PD cassette.
Figure 6:
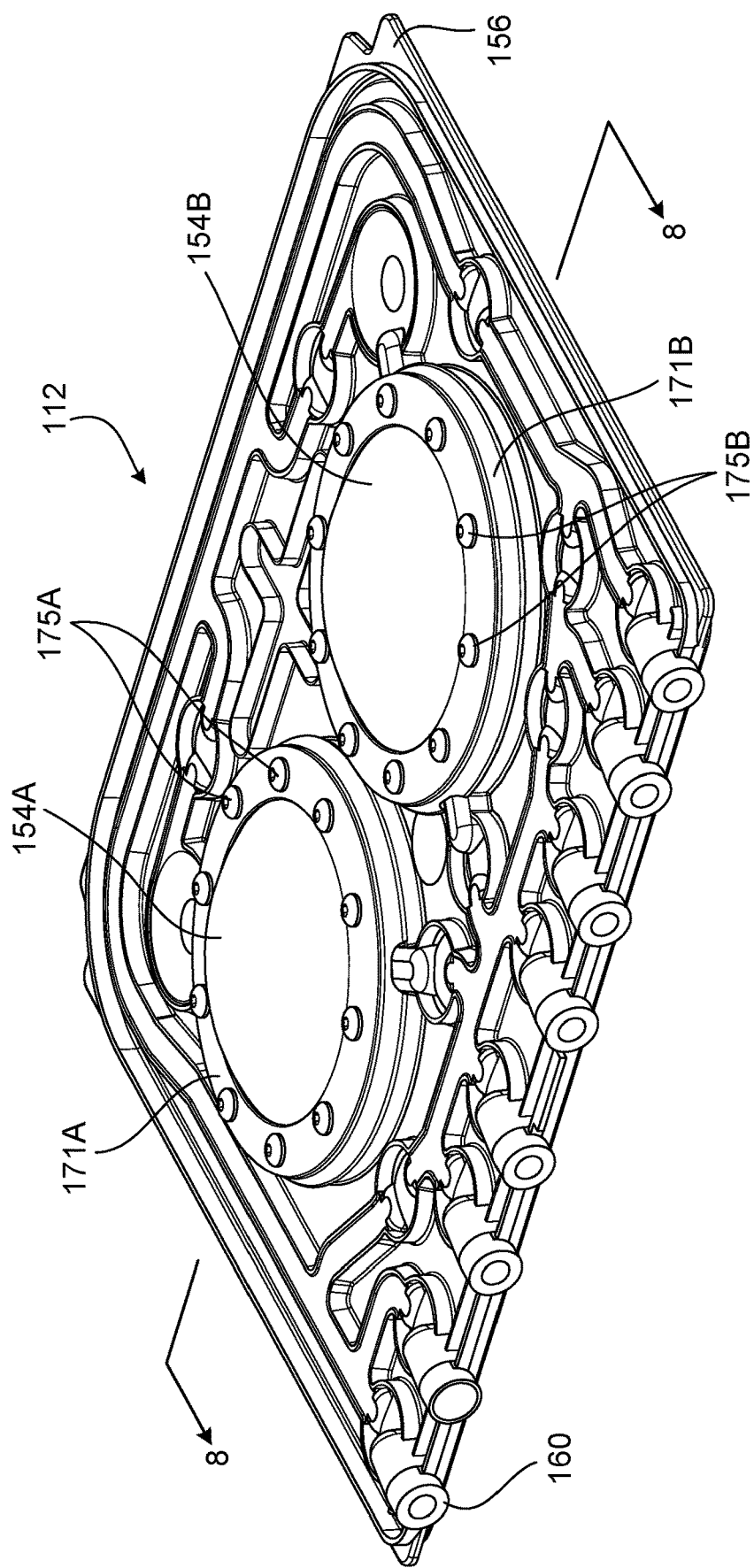
FIG. 6 is a perspective view of the PD cassette, from a rigid base side of the PD cassette.
Figure 7:
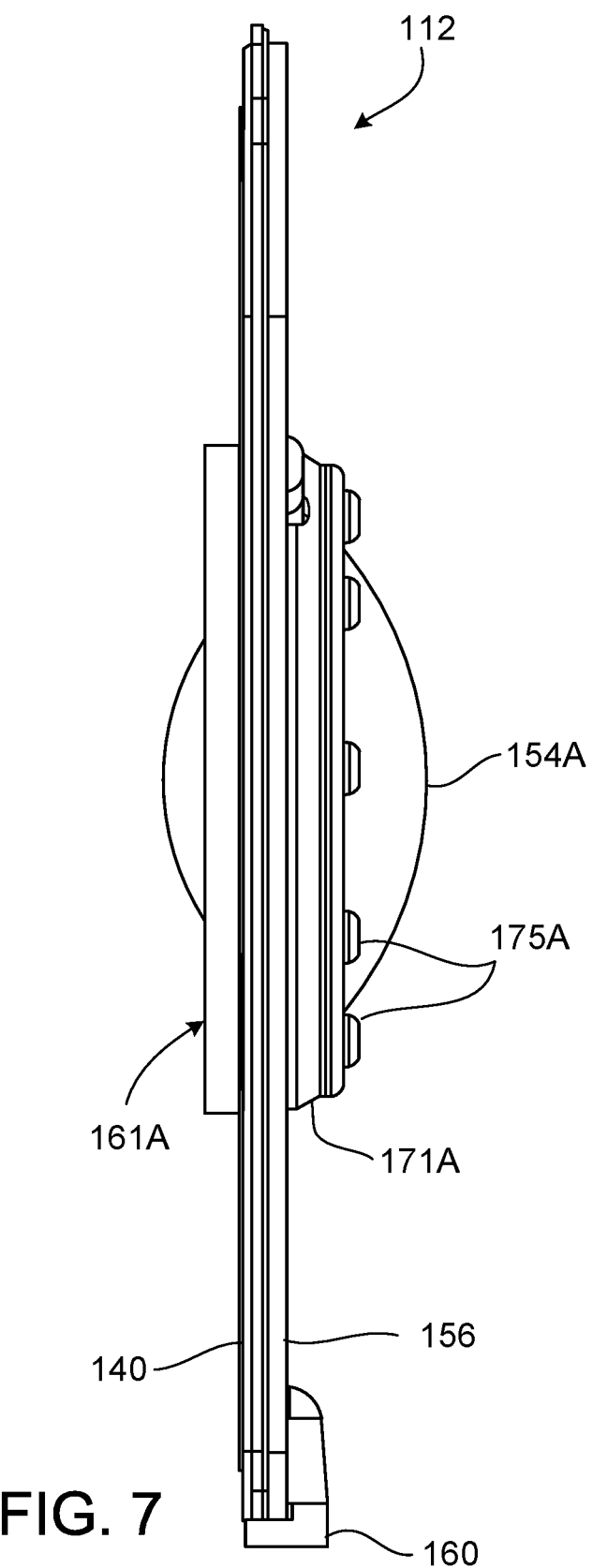
FIG. 7 is a side view of the PD cassette.

FIG. 4 is an exploded, perspective view of the cassette 112. FIGS. 5 and 6 are perspective views of the assembled cassette 112 from the membrane side and rigid base side, respectively, and FIG. 7 is a side view of the assembled cassette 112. Referring to FIGS. 4-6, the pumping membranes 161A, 161B, which partially encapsulate support rings 169A, 169B, overlie recessed regions 163A, 163B formed by the hollow dome-shaped protrusions 154A, 154B (shown in FIGS. 6-8) of the base 156. Peripheral regions 177A, 177B of the pumping membranes 161A, 161B extend into the recessed regions 163A, 163B of the base 156 and engage the inner walls of the hollow dome-shaped protrusions 154A, 154B. Retainer rings 171A, 171B are positioned on the rigid base side of the cassette 112 opposite the pumping membranes 161A, 161B and surround the hollow dome-shaped protrusions 154A, 154B of the base 156. Nuts 173A, 173B and bolts 175A, 175B are used to apply a compressive force to peripheral regions of the pumping membranes 161A, 161B when the cassette is fully assembled, as will be described in greater detail below. As a result, the peripheral regions of the pumping membranes 161A, 161B are pressed against the base 156 to form a liquid-tight seal around the recessed regions 163A, 163B when the cassette 112 is fully assembled.

In addition to the pumping membranes 161A, 161B, the cassette 112 includes a thinner, flexible membrane 140 that is attached to the periphery of the base 156 and to planar portions of the base 156 that surround recessed regions 163A, 163B. The flexible membrane 140 includes openings 141A, 141B that are sized and shaped to generally correspond to the recessed regions 163A, 163B and to receive the pumping membranes 161A, 161B. A series of raised ridges 167 extend from a planar surface of the base 156 towards and into contact with the inner surface of the flexible membrane 140 to form fluid pathways that lead to and from the pump chambers 138A, 138B when the cassette 112 is compressed between the door 108 and the cassette interface 110 of the PD cycler 102.

Figure 8:
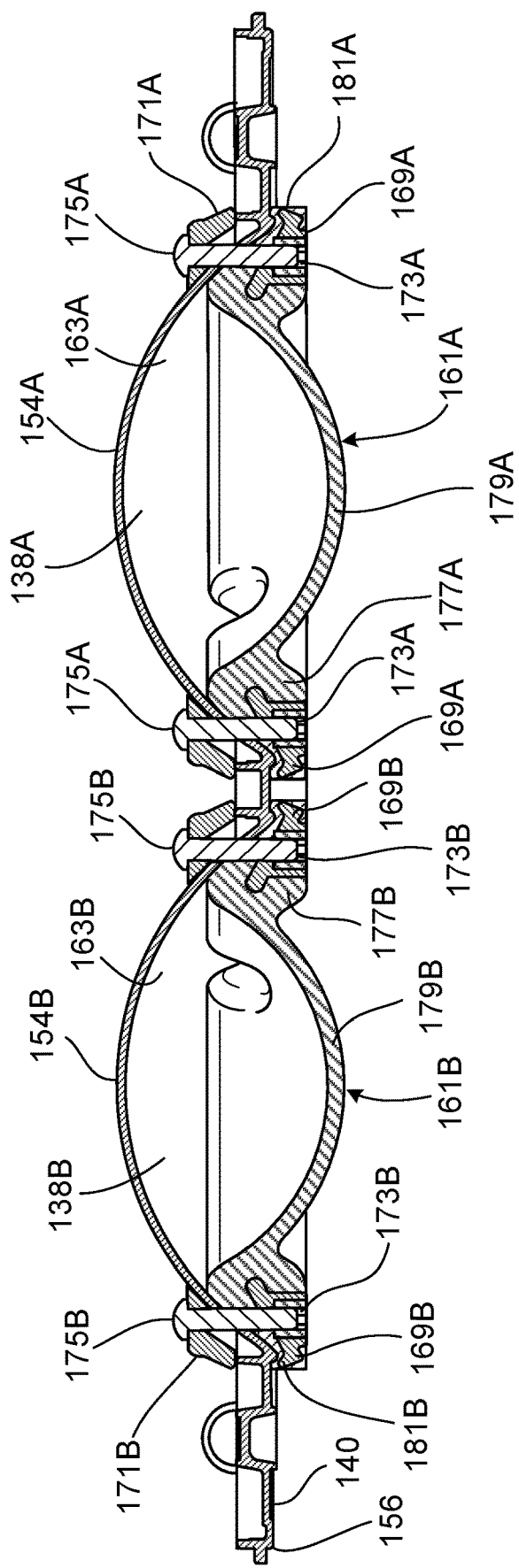
FIG. 8 is a cross-sectional view of the PD cassette, taken along line 8-8 in FIG. 6.

Referring now to FIGS. 4 and 8, the pumping membranes 161A, 161B extend partially into the recessed regions 163A, 163B of the base 156 and cooperate with the recessed regions 163A, 163B of the base 156 to form the fluid pump chambers 138A, 138B. The relatively thick peripheral regions 177A, 177B of the pumping membranes 161A, 161B, which partially encapsulate the support rings 169A, 169B, engage the circumferences of the recessed regions 163A, 163B of the base 156 to form liquid-tight seals around the circumferences of the pump chambers 138A, 138B. The peripheral regions 177A, 177B of the pumping membranes 161A, 161B define bores that align with bores extending through the support rings 169A, 169B. The bores of the pumping membranes 161A, 161B and support rings 169A, 169B align with bores formed in the hollow protrusions 154A, 154B of the cassette base 156 to form through-holes through which the bolts 175A, 175B can extend.

Dome-shaped central portions 179A, 179B of the pumping membranes 161A, 161B overlie the associated central portions of the recessed regions 163A, 163B of the base 156 to form the pump chambers 138A, 138B. The distance between the apexes of the dome-shaped portions 179A, 179B and the apexes of the associated hollow protrusions 154A, 154B typically ranges from about 0.100 inch to about 0.5 inch. The dome-shaped portions 179A, 179B of the pumping membranes 161A, 161B provide increased pump chamber volume, as compared to cassettes that have flat or planar pumping membranes. In addition, the dome-shaped portions 179A, 179B of the pumping membranes 161A, 161B facilitate rebounding of the pumping membranes 161A, 161B away from the base 156 as the pistons are retracted during use. It is this rebounding action of the pumping membranes 161A, 161B that generates vacuum pressure within the fluid pump chambers 138A, 138B, allow dialysis solution to be pulled into the fluid pump chambers 138A, 138B.

The dome-shaped central portions 179A, 179B of the pumping membranes 161A, 161B are thinner (e.g., about 0.05 inch to about 0.20 inch thinner) than the peripheral regions 177A, 177B of the pumping membranes 161A, 161B. For example, each of the dome-shaped portions 179A, 179B can have a thickness, measured at the top or apex of the dome-shaped portion 179A, 179B, of about 0.05 inch to about 0.10 inch, and each of the peripheral regions 177A, 177B can have a thickness of about 0.120 inch to about 0.250 inch in their edge regions. In some implementations, the dome-shaped portions have a thickness of about 0.075 inch and the peripheral regions 177A, 177B have a thickness of about 0.120 inch. The increased thickness of the pumping membranes 161A, 161B in the peripheral regions 177A, 177B can provide increased resilience to the dome-shaped portions 179A, 179B and thus increase the ability of the dome-shaped portions 179A, 179B to self-expand after being compressed inwardly toward the base 156.

The material and shape of the pumping membranes 161A, 161B can be selected to provide the pumping membranes 161A, 161B with a desired resiliency. In certain implementations, the pumping membranes 161A, 161B are configured to cause the pumping membranes 161A, 161B to self-expand or rebound with an outward force of about 20N to about 250N (e.g., about 20N to about 100N, about 55N) after being pressed into the recessed regions 163A, 163B of the base 156 and then released (e.g., by extending and then retracting the pistons of the PD cycler). By expanding with such a force, the pumping membranes 161A, 161B can create a vacuum pressure of about 150 mbar to about 200 mbar (e.g., about 150 mbar) within the pump chambers 138A, 138B and within fluid lines that are fluidly connected to the pump chamber. However, the pumping membranes 161A, 161B can be formed in a way to expand with higher or lower forces, depending on the intended use or application of the cassette 112.

Typically, the pumping membranes 161A, 161B are formed of silicone rubber. However, as an alternative to or in addition to silicone rubber, the pumping membrane material can include various other resilient elastomeric materials, such as neoprene, nitrile rubber (e.g., Buna-n), fluoroelastomer (e.g., Viton), etc.

Still referring to FIGS. 4 and 8, the support rings 169A, 169B are partially encapsulated within the material of the pumping membranes 161A, 161B such that only the bottom surfaces of the support rings 169A, 169B (based on the view shown in FIG. 8) are exposed. Cavities extend inwardly from these exposed surfaces of the support rings 169A, 169B for receiving the nuts 173A, 173B. These cavities and sized and shaped so that the outer surfaces of the nuts 173A, 173B are substantially flush with the exposed surfaces of the support rings 169A, 169B, which are substantially flush with the outers surfaces of the peripheral regions 177A, 177B of the pumping membranes 161A, 161B. The support rings 169A, 169B include annular projections 181A, 181B that together with the pumping membrane material surrounding those projections 181A, 181B engage raised annular flanges or lips 165A, 165B that extend from the base 156 and surround the recessed regions 163A, 163B. This arrangement can help to prevent the peripheral regions 177A, 177B of the pumping membranes 161A, 161B from sliding further into the recessed regions 163A, 163B when the pistons 135A, 135B are advanced during use to push the dome-shaped portions 179A, 179B of the pumping membranes 161A, 161B into the recessed regions 163A, 163B to expel dialysis solution from the fluid pump chambers 138A, 138B.

The support rings 169A, 169B are more rigid than the pumping membrane material and thus provide the peripheral regions 177A, 177B of the pumping membranes 161A, 161B with increased strength. The support rings 169A, 169B also distribute forces applied by the nuts 173A, 173B and bolts 175A, 175B across a larger area of the membrane than if the nuts 173A, 173B and bolts 175A, 175B were to extend through the pumping membrane material alone. As a result, the support rings 169A, 169B can help to prevent the peripheral regions 177A, 177B of the pumping membranes 161A, 161B from tearing or deforming and can therefore help to maintain a liquid-tight seal between the pumping membranes 161A, 161B and the cassette base 156.

The size of the support rings 169A, 169B is dependent upon the size of the cassette being used and the amount of additional support desired to be added to the pumping membrane material for a particular application. In some implementations, the support rings 169A, 169B have an inner diameter of about 1.0 inch to about 2.0, an outer diameter of about 2.0 inch to about 3.0 inch, and a thickness of about 0.050 inch to about 0.200 inch.

The support rings 169A, 169B are typically formed of polypropylene. However, as an alternative to or in addition to polypropylene, the support rings 169A, 169B can include certain other rigid plastics (e.g., polycarbonate, ABS, polyvinyl chloride, etc.) and/or certain metals (e.g., aluminum, steel, stainless steel, etc.).

The support rings 169A, 169B are typically encapsulated within the elastomeric material of the pumping membranes 161A, 161B using an overmolding technique. However, any of various other techniques that enable encapsulation or partial encapsulation of the support rings 169A, 169B by the membrane material can be used.

Still referring to FIGS. 4 and 8, the retainer rings 171A, 171B surround the hollow protrusions 154A, 154B extending from the opposite side of the rigid base 156. The retainer rings 171A, 171B include bores that align with the bores of the hollow protrusions 154A, 154B, the pumping membranes 161A, 161B, and the support rings 169A, 169B such that the bolts 175A, 175B can pass through those components and engage the nuts 173A, 173B disposed within the cavities of the support rings 169A, 169B. The nuts 173A, 173B and bolts 175A, 175B are tightened to press the pumping membranes 161A, 161B against the base 156 and form a liquid-tight seal around the pump chambers 138A, 138B. The retainer rings 171A, 171B distribute the forces of the bolts 175A, 175B across a larger surface area of the base 156 than if the bolts 175A, 175B were secured directly to the base 156. In addition, the retainer rings 171A, 171B provide flat surfaces for engaging the flat heads of the bolts 175A, 175B.

The size and material of each of the retainer rings 171A, 171B can be selected to provide sufficient support to withstand the compression forces applied by the nuts 173A, 173B and bolts 175A, 175B without damage. In some implementations, the retainer rings 171A, 171B have an inner diameter of about 1.0 inch to about 2.0, an outer diameter of about 2.0 inch to about 3.0 inch, and a thickness of about 0.050 inch to about 0.200 inch. Typically, the retainer rings 171A, 171B are formed of polypropylene. However, as an alternative to or in addition to polypropylene, the retainer rings 171A, 171B can include certain other rigid plastics (e.g., polycarbonate, ABS, polyvinyl chloride, etc.) and/or certain metals (e.g., aluminum, steel, stainless steel, etc.).

Referring now to FIGS. 4-6, the flexible membrane 140 is attached to the periphery of the base 156 and to planar portions of the base 156 surrounding the recessed regions 163A, 163B. All other portions of the membrane 140 that overlie the base 156 are typically not attached to the base 156. Rather, those portions of the membrane 140 sit loosely atop the raised ridges 167 extending from the planar surface of the base 156. Any of various attachment techniques, such as adhesive bonding and thermal bonding, can be used to attach the membrane 140 to the periphery of the base 156.

When compressed against the base 156, the flexible membrane 140 cooperates with the series of raised ridges 167 extending from the planar surface of the base 156 to form a series of fluid pathways 158 that lead to and from the pump chambers 138A, 138B and to form the multiple, depressible dome regions 146, which are widened portions (e.g., substantially circular widened portions) of the fluid pathways 158. During use, the dialysis solution flows to and from the pump chambers 138A, 138B via the fluid pathways 158 and dome regions 146. At each depressible dome region 146, the membrane 140 can be deflected to contact the planar surface of the base 156 from which the raised ridges 167 extend. Such contact can substantially impede (e.g., prevent) the flow of dialysis solution along the region of the pathway 158 associated with that dome region 146 during use. Thus, as described in further detail below, the flow of dialysis solution through the cassette 112 can be controlled through the selective depression of the depressible dome regions 146 by selectively inflating the inflatable members 142 of the PD cycler 102.

The thickness and material(s) of the membrane 140 are selected so that the membrane 140 has sufficient flexibility to flex toward the base 156 in response to the force applied to the membrane 140 by the inflatable members 142. In certain implementations, the membrane 140 is about 0.100 micron to about 0.150 micron in thickness. However, various other thicknesses may be sufficient depending on the type of material used to form the membrane 140.

Any of various different materials that permit the membrane 140 to deflect in response to inflation of the inflatable members 142 without tearing can be used to form the membrane 140. In some implementations, the membrane 140 includes a three-layer laminate. In certain implementations, for example, inner and outer layers of the laminate are formed of a compound that is made up of 60 percent Septon® 8004 thermoplastic rubber (i.e., hydrogenated styrenic block copolymer) and 40 percent ethylene, and a middle layer is formed of a compound that is made up of 25 percent Tuftec® H1062(SEBS: hydrogenated styrenic thermoplastic elastomer), 40 percent Engage® 8003 polyolefin elastomer (ethylene octene copolymer), and 35 percent Septon® 8004 thermoplastic rubber (i.e., hydrogenated styrenic block copolymer). The membrane can alternatively include more or fewer layers and/or can be formed of different materials.

The rigidity of the base 156 helps to hold the cassette 112 in place within the cassette compartment 114 of the PD cycler 102 and to prevent the base 156 from flexing and deforming in response to forces applied to the projections 154A, 154B by the piston heads 134A, 134B and in response to forces applied to the planar surface of the base 156 by the inflatable members 142. The base 156 can be formed of any of various relatively rigid materials. In some implementations, the base 156 is formed of one or more polymers, such as polypropylene, polyvinyl chloride, polycarbonate, polysulfone, and other medical grade plastic materials. In certain implementations, the base 156 is formed of one or more metals or alloys, such as stainless steel. The base 156 can alternatively be formed of various different combinations of the above-noted polymers and metals. The base 156 can be formed using any of various different techniques, including machining, molding, and casting techniques.

Referring again to FIGS. 5 and 6, fluid line connectors 160 are positioned along the bottom edge of the cassette 112. The fluid pathways 158 in the cassette 112 lead from the pumping chambers 138A, 138B to the various connectors 160. The connectors 160 are positioned asymmetrically along the width of the cassette 112. The asymmetrical positioning of the connectors 160 helps to ensure that the cassette 112 will be properly positioned in the cassette compartment 114 with the membrane 140 of the cassette 112 facing the cassette interface 110. The connectors 160 are configured to receive fittings on the ends of the dialysis solution bag lines 126, the heater bag line 128, the patient line 130, and the drain line 132. One end of the fitting can be inserted into and bonded to its respective line and the other end can be inserted into and bonded to its associated connector 160. By permitting the dialysis solution bag lines 126, the heater bag line 128, the patient line 130, and the drain line 132 to be connected to the cassette, as shown in FIGS. 1 and 2, the connectors 160 allow dialysis solution to flow into and out of the cassette 112 during use.

Figure 9:
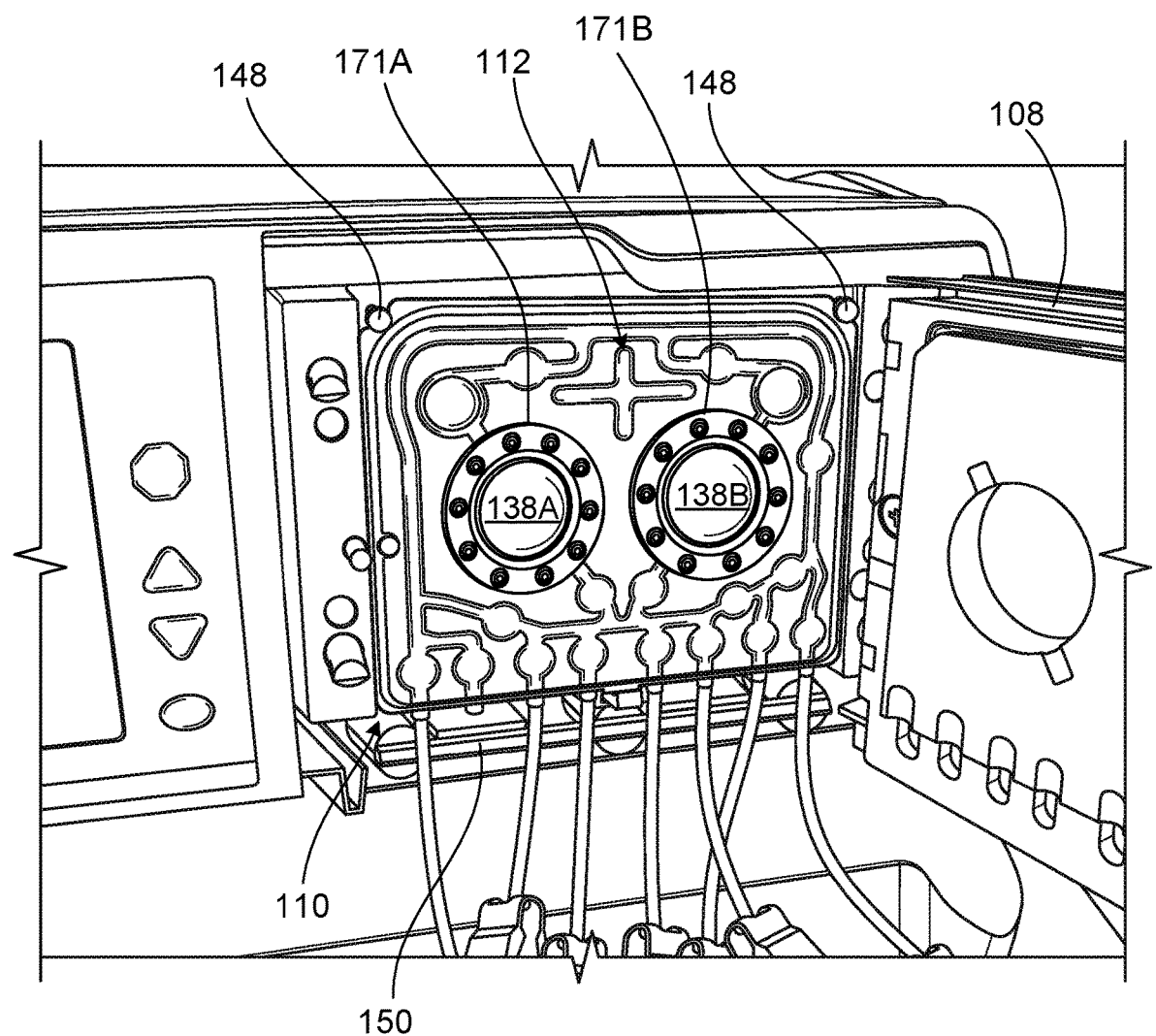
FIG. 9 is a partial perspective view of the PD system of FIG. 1 with the PD cassette in the cassette compartment of the PD cycler and the door of the PD cycler open.

As shown in FIG. 9, before treatment, the door 108 of the PD cycler 102 is opened to expose the cassette interface 110, and the cassette 112 is positioned with its membranes 140, 161A, 161B adjacent to the cassette interface 110. The cassette 112 is positioned such that the pump chambers 138A, 138B of the cassette 112 are aligned with the piston heads 134A, 134B of the pistons 135A, 135B. In order to ensure that the pump chambers 138A, 138B align with the piston heads 134A, 134B, the cassette 112 is positioned between the locating pins 148 and the lower ledge 150 extending from the cassette interface 110. The asymmetrical positioning of the connectors 160 of the cassette 112 act as a keying feature that reduces or eliminates the likelihood that the cassette 112 will be installed with the membranes 140, 161A, 161B facing in the wrong direction (e.g., facing outward toward the door 108). Additionally or alternatively, the locating pins 148 can be dimensioned to be less than the maximum protrusion of the projections 154A, 154B such that the cassette 112 cannot contact the locating pins 148 if the membranes 140, 161A, 161B are facing outward toward the door 108.

While loading the cassette 112 into the PD cycler 102, the piston heads 134A, 134B are typically retracted within the piston access ports 136A, 136B. This positioning of the piston heads 134A, 134B can reduce the likelihood of damage to the piston heads 134A, 134B during installation of the cassette 112.

FIGS. 10A-10B illustrate the pump chamber 138A and its associated piston head 134A throughout different phases of operation. It should be understood that the other piston head 134B would operate in a similar manner to pump dialysis solution to and from the other pump chamber 138B. During operation, the piston heads 134A, 134B are reciprocated to sequentially alter the volume of each of the pump chambers 138A, 138B. Typically, as the piston head 134A is extended (or stroked outwardly), the other piston head 134B is retracted (or stroked inwardly), and vice versa. As a result, dialysis solution is expelled from the pump chamber 138A at the same time that dialysis solution is drawn into the pump chamber 138B, and vice versa.

Referring to FIG. 10A, with the cassette 112 positioned adjacent to the cassette interface 110, the door 108 of the PD cycler 102 is closed over the cassette 112 such that the cassette 112 is contained within the cassette compartment 114 between the door 108 and the cassette interface 110. With the cassette 112 positioned in the cassette compartment 114, the inflatable pad within the door 108 is inflated to compress the cassette 112 between the door 108 and the cassette interface 110. This compression of the cassette 112 holds the projections 154A, 154B of the cassette 112 in the recesses 152A, 152B of the door 108 and presses the membrane 140 tightly against the raised ridges 167 extending from the planar surface of the rigid base 156 to form the enclosed fluid pathways 158 and dome regions 146 (shown in FIG. 5). Because the PD system 100 does not require a vacuum system to move the pumping membranes 161A, 161B overlying the pump chambers 138A, 138B, a substantially airtight seal between the door 108 and the cassette interface 110 is typically not required. Thus, as compared to systems including a vacuum system adapted to retract portions of the cassette membrane overlying pump chambers, the door sealing mechanism of the PD cycler 102 can be simpler and more cost effective.

As shown in FIG. 10B, with the cassette 112 secured within the cassette compartment 114, the piston 135A is advanced toward the base 156 of the cassette 112. As the piston 135A is advanced to its substantially fully extended position, the piston head 134A pushes the dome-shaped portion 179A of the pumping membrane 161A into the recessed region 163A of the base 156 such that the dome-shaped portion 179A of the pumping membrane 161A becomes inverted. In this position, the inner surface of the dome-shaped portion 179A of the pumping membrane 161A comes into contact or near contact with the inner surface of the hemispherical projections 154A, 154B of the rigid base 156 of the cassette 112. As a result, the volume of the pump chamber 138A is at its minimum such that all or nearly all liquid that was present in the pump chamber 138A prior to advancement of the piston 135A is expelled from the pump chamber 138A and into the fluid passageways 158 of the cassette 112 that lead away from the pump chamber 138A as the piston 135A is advanced into this fully extended position.

Figure 10C:
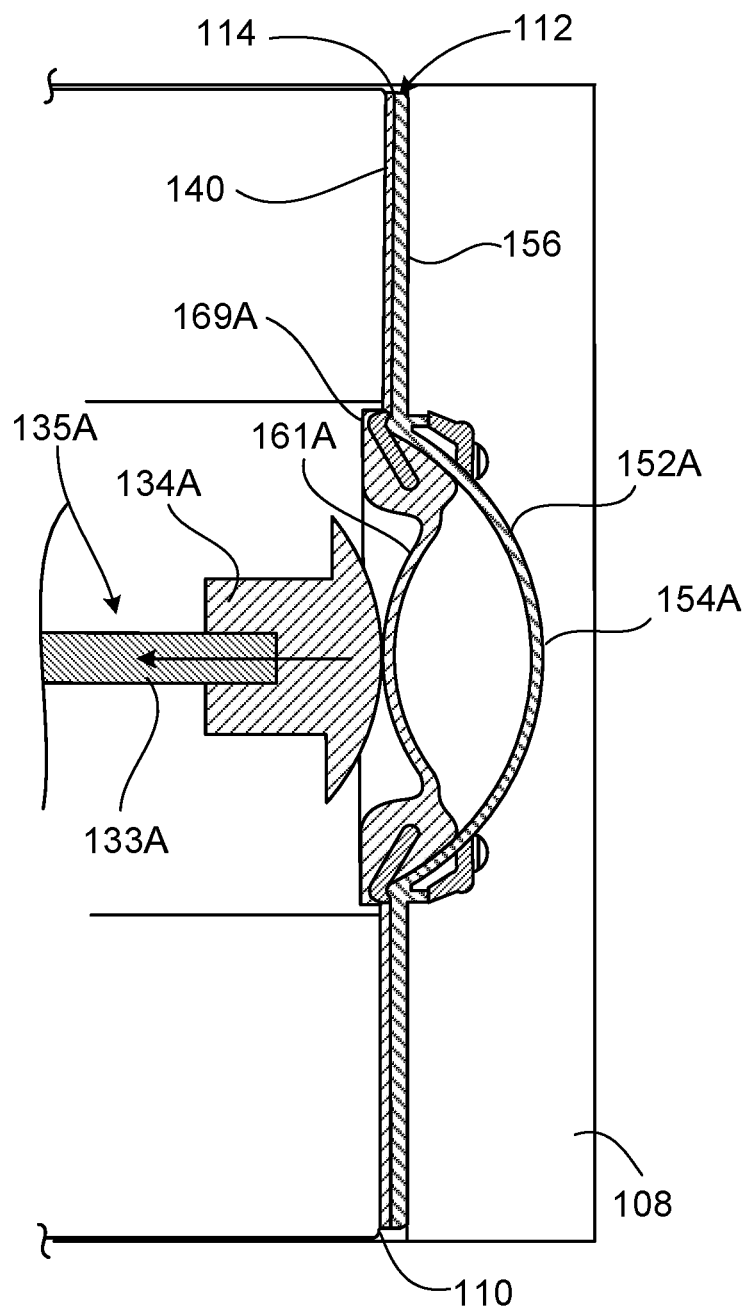

In order to draw PD solution into the pump chamber 138A, the piston 135A is then retracted to a retracted position, as shown in FIG. 10C. As the piston head 134A retracts, the resilient dome-shaped portion 179A of the pumping membrane 161A automatically rebounds (or self-expands) to increase the volume of the pump chamber 138A. While the retraction speed of the piston head 134A will limit the speed with which the dome-shaped portion of the pumping membrane 161A is allowed to rebound, the piston head 134A does not apply a pulling force to the pumping membrane 161A. Instead, the inherent resiliency of the dome-shaped portion 179A of the pumping membrane 161A is what causes the dome-shaped portion 179A to rebound outwardly away from the recessed region 163A of the base 156 of the cassette 112. The dome-shaped portion 179A of the pumping membrane 161A is not allowed to rebound faster than the piston head 134A is retracted because the piston head 134A would apply a resistance force to the dome-shaped portion 179A of the pumping membrane 161A in that situation. As a result, the retraction speed of the piston head 134A can be controlled in a manner to ensure that vacuum pressure generated within the pump chamber 138A is maintained within an acceptable range.

After retracting the piston head 134A a desired distance, the dialysis fluid in the pump chamber 138A can be forced out of the pump chamber 138A by again returning the piston head 134A to the fully extended position shown in FIG. 10B, causing the pumping membrane 161A to deflect inward toward the rigid base 156 and thus decreasing the volume of the pump chamber 138A.

As noted above, while forcing dialysis solution into and out of the pump chambers 138A, 138B, certain inflatable members 142 of the PD cycler 102 can be selectively inflated to direct the pumped dialysis solution along desired pathways in the cassette 112.

Figure 11A:
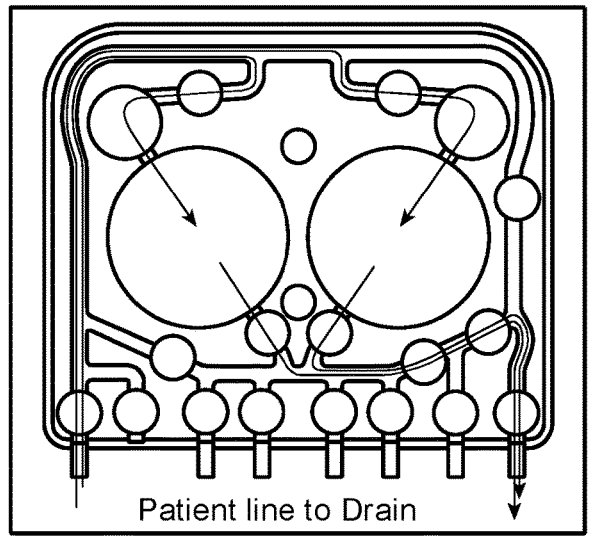
FIGS. 11A-11C illustrate various fluid flow paths through the PD cassette of the PD system of FIG. 1 during a PD treatment.

Referring back to FIGS. 1 and 2, during PD treatment, the patient line 130 is connected to a patient's abdomen via a catheter, and the drain line 132 is connected to a drain or drain receptacle. The PD treatment typically begins by emptying the patient of spent dialysis solution that remains in the patient's abdomen from the previous treatment. To do this, the motors of the PD cycler 102 are activated to cause the pistons 135A, 135B to reciprocate and selected inflatable members 142 are inflated to cause the spent dialysis solution to be drawn into the pump chambers 138A, 138B of the cassette 112 from the patient and then pumped from the pump chambers 138A, 138B to the drain via the drain line 132. This flow path of the spent dialysis solution through the fluid pathways 158 in the cassette 112 is shown in FIG. 11A.

Figure 11B:
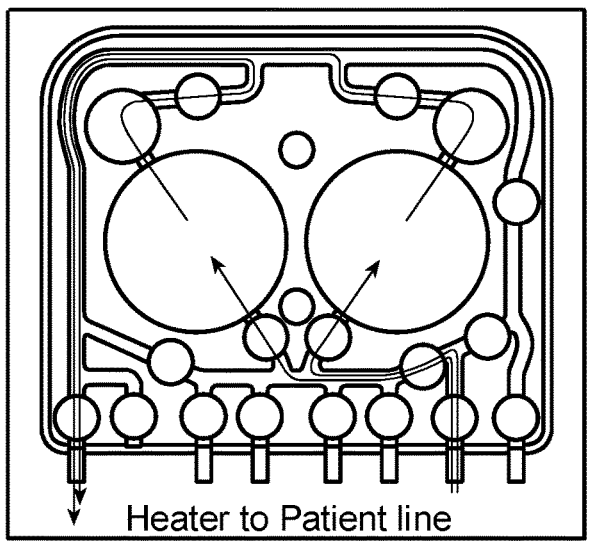

After draining the spent dialysis solution from the patient, heated dialysis solution is transferred from the heater bag 124 to the patient. To do this, the motors of the PD cycler 102 are activated to cause the pistons 135A, 135B to reciprocate and certain inflatable members 142 of the PD cycler 102 are inflated to cause the spent dialysis solution to be drawn into the pump chambers 138A, 138B of the cassette 112 from the heater bag 124 via the heater bag line 128 and then pumped from the pump chambers 138A, 138B to the patient via the patient line 130. This flow path of the dialysis solution through the fluid pathways 158 in the cassette 112 is shown in FIG. 11B.

Figure 11C:
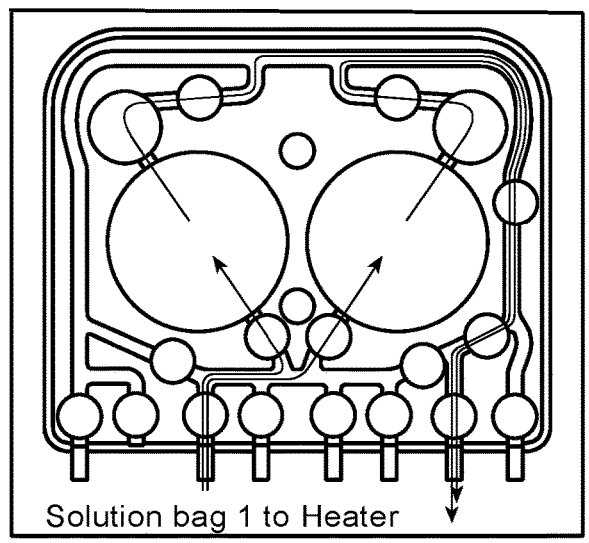

Once the dialysis solution has been pumped from the heater bag 124 to the patient, the dialysis solution is allowed to dwell within the patient for a period of time. During this dwell period, toxins cross the peritoneum into the dialysis solution from the patient's blood. As the dialysis solution dwells within the patient, the PD cycler 102 prepares fresh dialysate for delivery to the patient in a subsequent cycle. In particular, the PD cycler 102 pumps fresh dialysis solution from one of the four full dialysis solution bags 122 into the heater bag 124 for heating. To do this, the motors of the PD cycler 102 are activated to cause the pistons 135A, 135B to reciprocate and certain inflatable members 142 of the PD cycler 102 are inflated to cause the dialysis solution to be drawn into the pump chambers 138A, 138B of the cassette 112 from the selected dialysis solution bag 122 via its associated line 126 and then pumped from the pump chambers 138A, 138B to the heater bag 124 via the heater bag line 128. This flow path of the dialysis solution through the fluid pathways 158 in the cassette 112 is shown in FIG. 11C.

After the dialysis solution has dwelled within the patient for the desired period of time, the spent dialysis solution is pumped from the patient to the drain. The heated dialysis solution is then pumped from the heater bag 124 to the patient where it dwells for a desired period of time. These steps are repeated with the dialysis solution from two of the three remaining dialysis solution bags 122. The dialysis solution from the last dialysis solution bag 122 is typically delivered to the patient and left in the patient until the subsequent PD treatment.

While the dialysis solution has been described as being pumped into the heater bag 124 from a single dialysis solution bag 122, dialysis solution can alternatively be pumped into the heater bag 124 from multiple dialysis solution bags 122. Such a technique may be advantageous, for example, where the dialysis solutions in the bags 122 have different concentrations and a desired concentration for treatment is intermediate to the concentrations of the dialysis solution in two or more of the bags 122.

After completion of the PD treatment, the piston heads 134A, 134B are retracted away from the cassette 112 to a sufficient distance such that the piston heads 134A, 134B no longer contact the pumping membranes 161A, 161B. The door 108 of the PD cycler is then opened and the cassette 112 is removed from the cassette compartment and discarded.

While certain implementations have been described, other implementations are possible.

While the above-described cassette 112 includes the support rings 169A, 169B and the retainer rings 171A, 171B, which are positioned on opposite sides of the base 156 from one another and are drawn together using fasteners in order to compress the pumping membranes 161A, 161B against the base 156, other techniques for securing the rings to one another can be used. For example, the rings can be ultrasonically staked or welded to one another.

While the pumping membranes 169A, 169B have been described as including encapsulated support rings 169A, 169B, in some implementations, the pumping membranes are separate components from the support rings. In such implementations, for example, the peripheral regions of the pumping membranes can be placed against portions of the cassette base surrounding the recessed regions that form the pump chambers, and the support rings can be positioned against the outer surfaces of the peripheral regions of the pumping membranes. The retainer rings can be positioned on the opposite side of the base from the pumping membranes in much the same way as described above, and the associated support rings and retainer rings can be secured together using any of the techniques described above to compress the sandwiched peripheral region of the pumping membrane against the cassette base to provide a liquid-tight seal around the pump chamber.

While the above-described cassettes have been described as using support rings and retainer rings to compress the pumping membranes against the base of the cassette, in certain implementations, only support rings are used. In such implementations, for example, the support rings, which can be either encapsulated within the pumping membranes or positioned against the outer surfaces of the pumping membranes, are secured to the base of the cassette rather than being secured to retainer rings on the opposite side of the base of the cassette. The support rings can be secured to the base using fastener elements, ultrasonic staking or welding, or any of various other suitable techniques described herein.

Figure 12:
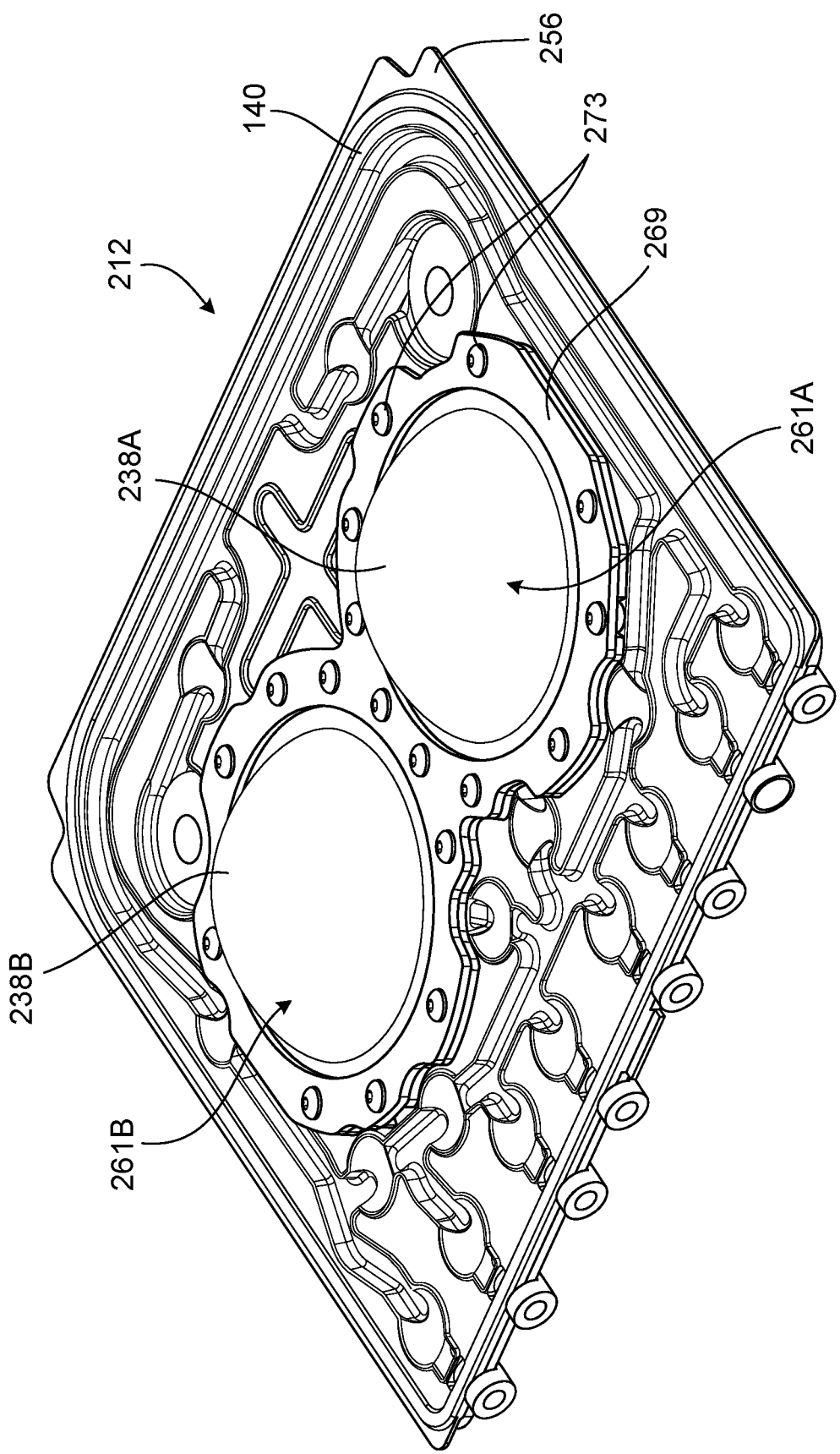
FIGS. 12 and 13 are perspective views from a membrane side and from a rigid base side, respectively, of a PD cassette that includes pumping membranes and a support ring that is separate from the pumping membranes and that cooperates with a retainer ring on the opposite rigid base side of the PD cassette to secure the pumping membranes to a base of the PD cassette.
Figure 13:
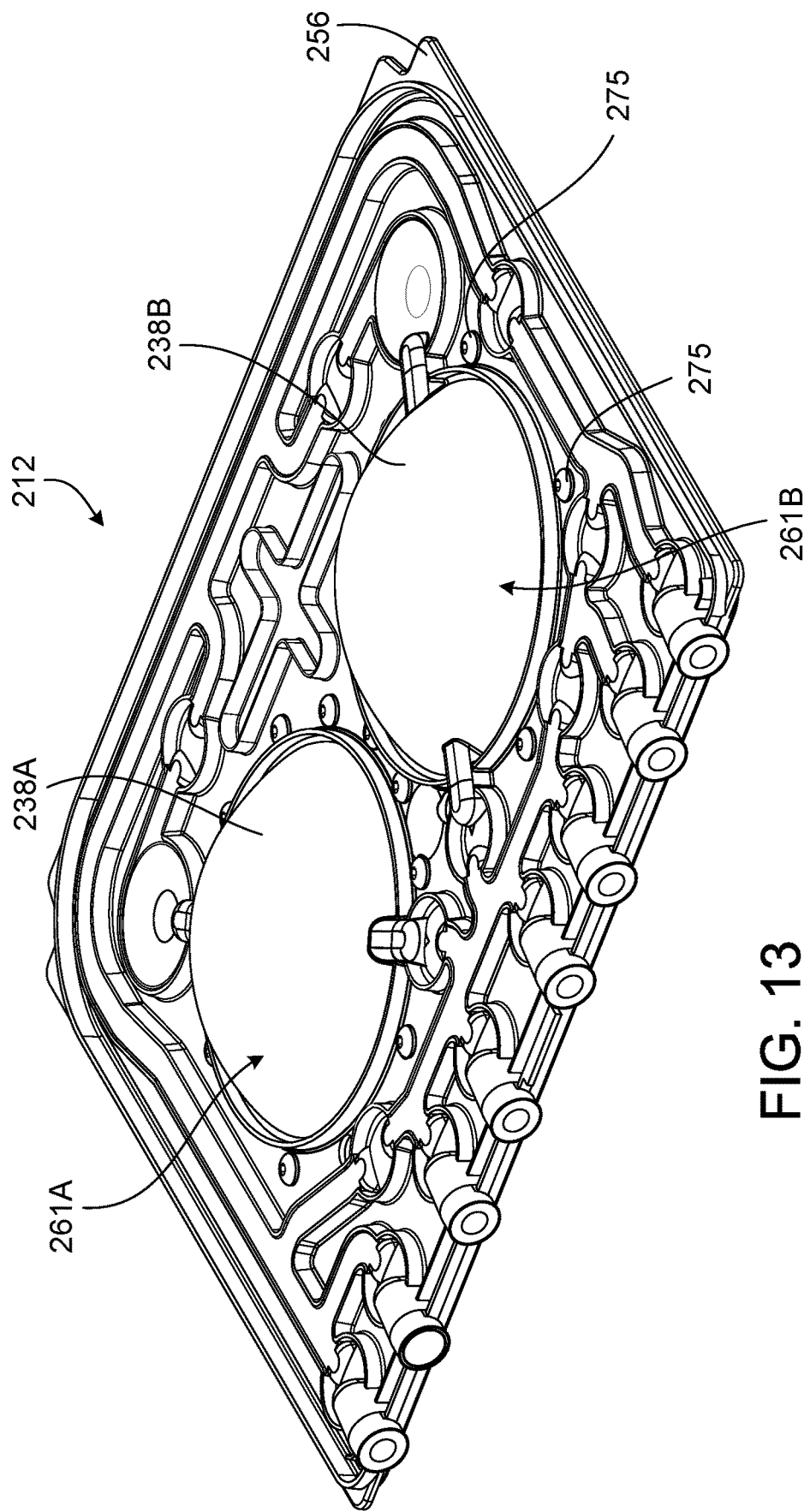

FIGS. 12 and 13 are perspective views from a membrane side and from a rigid base side of a cassette 212. The cassette 212 includes a rigid base 256 that is similar to the rigid bases of the cassettes described above except for the location of apertures through which bolts 275 extend differ from those cassettes described above. A support ring 269 in the shape of a figure eight is used to compress peripheral regions of pumping membranes 261A, 261B against portions of the base 256 that surround recessed regions of the base 256 in order to provide liquid-tight fluid pump chambers between the pumping membranes 261A, 261B and the recessed regions of the base 256. Unlike the pumping membranes 161A, 161B described above, which include encapsulated support rings 169A, 169B, the support ring 269 and pumping membranes 261A, 261B of the cassette 212 shown in FIGS. 12 and 13 are separate components. As shown in FIG. 12, the support ring 269 is placed against the outer surfaces of the peripheral regions of the pumping membranes 261A, 261B. The support ring 269 is shaped to conform to the various raised features extending from the base 256 of the cassette 212. This helps to ensure that the support ring 269 can be pulled tightly enough against the base 256 to form the liquid-tight seal between the peripheral regions of the pumping membranes 261A, 261B and the portions of the base 256 surrounding the pumping chambers 238A, 238B. Typically, the support ring has a thickness of about 0.050 inch to about 0.200 inch.

Unlike certain cassettes described above, the cassette 212 does not utilize a retainer ring. Rather, as shown in FIG. 13, heads of the bolts 275, which pass through aligned apertures in the support ring 269, the pumping membranes 261A, 261B, and the base 256, directly contact the outer surface of the rigid base 256. Thus, while the nuts 273 are supported by the support ring 269, the base 256 provides direct support for the heads of the bolts 275. Compression forces generated by screwing the nuts 273 onto the bolts 275 are used to compress the peripheral regions of the pumping membranes 261A, 261B between the support ring 269 and the rigid base 256.

The pumping membranes 261A, 261B and the support ring 269 can be formed of any of the materials described above with respect to the pumping membranes 161A, 161B and the support rings 169A, 169B, respectively.

While the cassettes described above include one or more rings that are used to secure the pumping membranes to the cassette base, in certain implementations, cassettes are constructed with no such rings. In such implementations, for example, the pumping membrane of the cassette can be welded or adhesively secured to the flange surrounding the recessed region of the base.

While the cassettes described above include pumping membranes that have dome-shaped central regions, in certain implementations, substantially flat or planar pumping membranes are used. The flat pumping membranes can be formed of any of the various materials used to form the pumping membranes described above and can be secured to the base of the cassette using any of the various techniques described above. The pumping membranes typically have a thickness of at least 0.125 inch. For example, the flat pumping membranes can have a thickness of about 0.125 inch to about 0.250 inch. Using relatively thick pumping membranes (as compared to membranes used on many conventional cassettes), helps to ensure that the pumping membranes are resilient and able to rebound (or self-expand) when depressed into the pump chamber and then released.

In addition to attaching the pumping membranes to the base, the pumping membranes can include resilient o-rings around their outer circumferences. The o-rings can be stretched around annular projections extending form the cassette base in order to further secure the pumping membranes to the base. The engagement between the annular projections of the base and the o-rings of the pumping membranes can help to stabilize the circumferential regions of the pumping membranes to ensure that those circumferential regions do not slip into the recessed regions of the base that form the pump chambers as the piston heads advance central portions of the pumping membranes into the recessed regions.

While the pumping membranes have been described as substantially circular membranes that are positioned over the pump chambers, in certain implementations, a pumping membrane is sized and shaped to cover substantially the entire base of the cassette. In such implementations, the pumping membrane can be attached to a peripheral region of the base. The pumping membrane can also be attached to portions of the base that surround the pump chambers. The pumping membrane is substantially flat or planar and can be formed of the same material(s) as the flat membranes discussed above. The pumping membrane can have the same thickness as the flat membranes discussed above. In some implementations, the portions of the pumping membrane overlying the pump chambers have a greater thickness than the surrounding portions of the membrane. For example, the portions of the pumping membrane overlying the pump chambers can have a thickness of about 0.125 inch to about 0.250 inch, while the other portions of the pumping membrane have a thickness of about 0.004 inch to about 0.006 inch.

Figure 14:
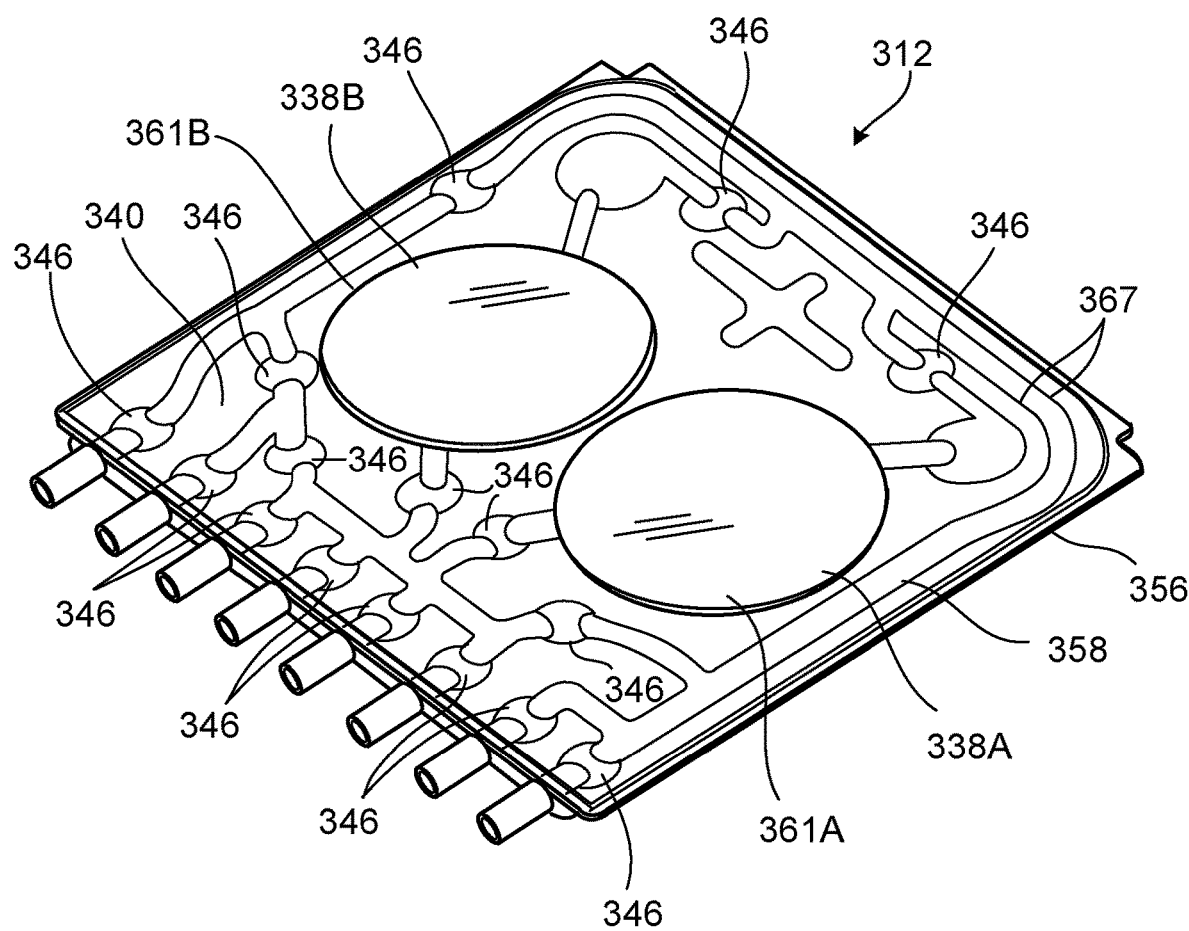
FIG. 14 is a perspective view of a PD cassette that includes substantially flat pumping membranes that overlie pump chambers of the PD cassette and are directly attached to a base of the PD cassette.

While the cassettes described above include pumping membranes that are secured to and directly contact the rigid base of the cassette, in some implementations, the pumping membranes are attached to an outer surface of another flexible membrane that overlies the pump chambers of the cassette. As shown in FIG. 14, for example, a cassette 312 includes a tray-like rigid base 356 and a flexible membrane 340 that is attached to (e.g., thermally bonded to, adhered to) the periphery of the base 356 and covers substantially the entire surface area of the base 356. The membrane 340 cooperates with recessed regions of the base 356 to form pump chambers 338A, 338B and cooperates with raised structural features 367 extending from planar regions of the base 356 to form a series of fluid pathways 358 and multiple, depressible dome regions 346, which are widened (e.g., substantially circular) portions of the fluid pathways 358.

Pumping membranes 361A, 361B are attached to (e.g., thermally bonded to, adhered to) those portions of the membrane 340 that overlie the pump chambers 338A, 338B. Typically, substantially the entire surface areas of the pumping membranes 361A, 361B are attached to the corresponding surfaces of the flexible membrane 340 to ensure that the portions of the flexible membrane 340 overlying the pump chambers 338A, 338B move in tandem with the pumping membranes 361A, 361B. The pumping membranes 361A, 361B are more resilient than the flexible membrane 340. Thus, the pumping membranes 361A, 361B can provide the flexible membrane walls of the pump chambers 338A, 338B with greater resiliency such that the flexible membrane walls can rebound under their own force (i.e., without the piston pulling the flexible membrane wall) to create vacuum pressure within the pump chambers 338A, 338B and draw fluid into the pump chambers 338A, 338B. The flexible membrane 340 can be identical to the flexible membrane 140 described above except the flexible membrane 340 does not include cut-outs over the pump chambers 338A, 338B. The pumping membranes 361A, 361B can be formed of the same material(s) as the pumping membranes discussed above. The pumping membranes typically have a thickness about 0.125 inch to about 0.250 inch.

As an alternative to using thermal or adhesive bonds between substantially the entire surface areas of the pumping membranes 361A, 361B and the flexible membrane 340, in certain implementations, only the perimeter edge regions of the pumping membranes 361A, 361B are bonded to the flexible membrane 340. In such implementations, for example, any air between the pumping membranes 361A, 361B and the flexible membrane 340 can be evacuated prior to forming the perimeter bond around the pumping membranes 361A, 361B. As a result, a passive vacuum between the pumping membranes 361A, 361B and the flexible membrane 340 will ensure that those portions of the flexible membrane 340 overlying the pump chambers 338A, 338B will move in tandem with the pumping membranes 361A, 361B.

While the pumping membranes 361A, 361B have been described as substantially circular membranes that are attached to the portions of the membrane 340 overlying the pump chambers 338A, 338B, in certain implementations, a single pumping membrane is sized and shaped to cover substantially the entire base 356 of the cassette 312. In such implementations, the pumping membrane is typically attached to substantially the entire surface area of the membrane 340. The pumping membrane is typically substantially flat or planar and can be formed of the same material(s) and have the same thickness as the pumping membranes 361A, 361B discussed above. Because the pumping membrane is relatively thick and thus requires significant force to deflect, the pumping membrane can include cutouts that align with the dome regions 346 of the cassette. In this manner, the inflatable valve members of the PD cycler can generate sufficient force to depress the exposed portions of the membrane 340 adjacent the cutouts and prevent fluid flow through the associated fluid passageway of the cassette. Alternatively, the PD cycler can be modified to generate increased pressures within the inflatable members that are sufficient to press the thicker pumping membrane and the underlying membrane 340 against the base 356 of the cassette to control liquid flow therethrough.

While the cassettes discussed above have been described as having two pump chambers, the cassettes can alternatively have more or fewer than two pump chambers.

While each of the pump chambers of the cassettes described above has been described or illustrated as including a fluid inlet port and a fluid outlet port, the pump chambers can alternatively include a single port that is used as both an inlet and an outlet.

While certain cassettes have been described as being positioned between locating pins and a lower ledge extending from a cassette interface of the PD cycler in order to hold the cassette in a position such that the piston heads align with the pump chambers of the cassette, other techniques for ensuring that the piston heads align with the pump chambers can alternatively or additionally be used. In some implementations, for example, the cassette is placed against the door of the PD cycler with the hollow projections of the cassette disposed in recesses of the PD cycler's door. The cassette is held in this position by retainer clips attached to the door. Upon closing the door, the piston heads of the PD cycler align with the pump chambers of the cassette.

Figure 15:
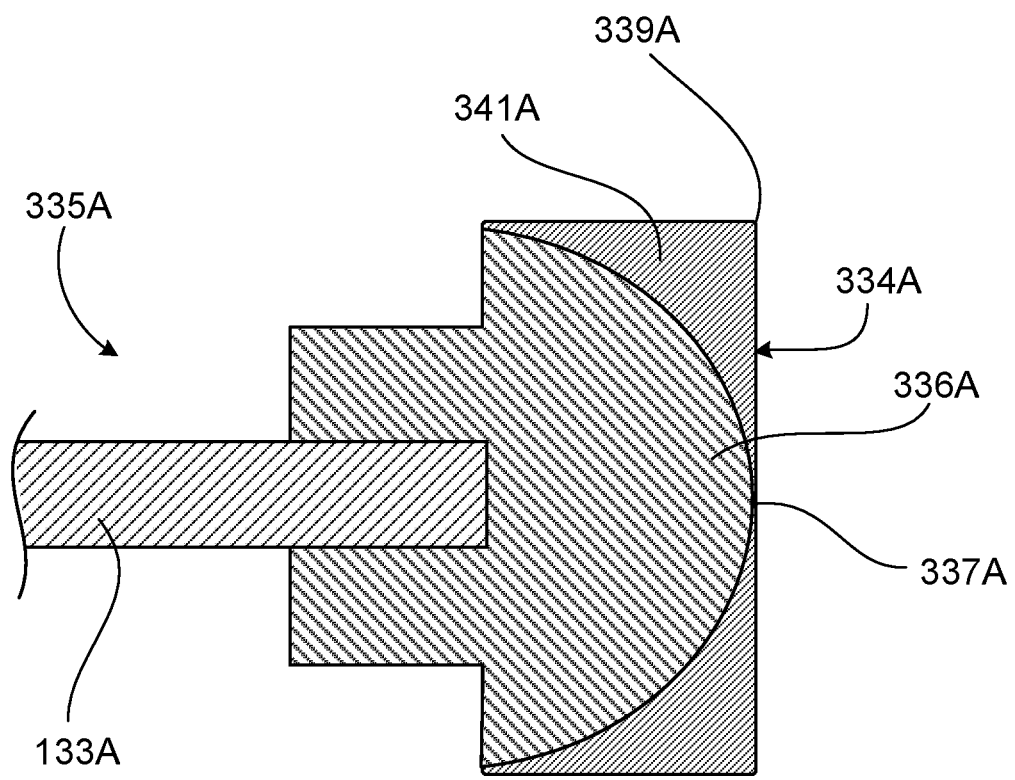
FIG. 15 is a cross-sectional view of a piston including a piston head that has a compressible portion that surrounds a central core.

While pistons having substantially rigid piston heads have been described, pistons having piston heads with compressible portions can alternatively be used. As shown in FIG. 15, for example, a piston 335A includes a piston head 334A secured to the piston shaft 133A. The piston head 334A includes a rigid core 336A surrounded by a compressible coating 341A. The rigid core 336A can be formed of any of the various materials described above with respect to the piston heads 134A, 134B. The compressible coating 341A is typically formed of an elastomer, such as Silicone, Medalist®, and thermoplastic elastomers (e.g., DYNAFLEX G2700, DYNAFLEX G6700, etc.).

As shown in FIG. 15, the compressible coating 341A increases in thickness, as measured in the axial direction of the piston head 334A, from a leading tip 337A of the piston head 334A towards an outer circumferential edge region 339A of the piston head 334A at which the maximum diameter of the piston head 334A can be found. As a result, the vast majority of the thickness of the piston head 334A (measured in the axial direction of the piston head 334A) in the outer circumferential edge region 339A is made up of the flexible elastomeric material of the compressible coating 341A, while the vast majority of the thickness of the piston head 334A (measured in the axial direction of the piston head 334A) in the tip region of the piston head 334A is made up of the rigid material of the core 336A. In some implementations, the compressible coating 341A has a thickness of about 0.1 inch to about 0.2 inch at the tip 337A of the piston head 334A and has a thickness of about 0.25 inch to about 0.45 inch at the outer circumferential edge region 339A of the piston head 334A. The compressible coating 338A increases the diameter of the piston head 334A (as compared to the piston heads 134A, 134B described above) at the leading edge of the piston head 334A and thus increases the surface area of the piston head 334A that contacts the pumping membrane of the cassette at a given time during use. As a result, the force applied to the pumping membrane of the cassette during use can be more uniformly distributed over the surface area of the portion of the pumping membrane overlying the pump chamber.

FIGS. 16A-16D schematically illustrate a method of using a PD cycler equipped with the piston 335A of FIG. 15 to expel dialysis solution from and draw dialysis solution into the fluid pump chamber 338A of the cassette 312 illustrated in FIG. 14. It should be understood that while only one piston 335A and one pump chamber 338A are illustrated in FIGS. 16A-16D, the PD cycler would generally be equipped with two pistons 335A, 335B that are aligned with the two corresponding pump chambers 338A, 338B of the cassette 312. Both of the pistons 335A, 335B would be operated in generally the same manner to pump dialysis solution to and from their respective pump chambers 338A, 338B.

Referring to FIG. 16A, the cassette 312 is first positioned in a cassette compartment 314 formed between the door 108 and the cassette interface 110 of the PD cycler and then compressed between the door 108 and the cassette interface 110 in the manner described above. This compression of the cassette 312 presses the pumping membrane 361A and the flexible membrane 340 against the base 356 to form a liquid-tight seal around the pump chamber 338A and also presses the membrane 340 tightly against the raised ridges 367 extending from the planar surface of the rigid base 356 to form the enclosed fluid pathways 358 and dome regions 346.

As shown in FIG. 16B, with the cassette 312 secured within the cassette compartment 314, the piston head 334A is advanced into contact with the pumping membrane 361A. Due to the compressible coating 338A positioned around the core 336A of the piston head 334A, which increases the diameter of the leading surface of the piston head 334A and makes the diameter of the piston head 334A more uniform along the length of the piston head 334A (as compared to the piston heads 134A, 134B described above), a larger area of the piston head 334A contacts the pumping membrane 361A during the initial phases of the outward stroke of the piston 335A. The leading surface of the piston head 334A can, for example, contact substantially the entire surface area of the portion of the pumping membrane 361A overlying the pump chamber 338A. In some implementations, for example, the piston head 334A, upon initial contact with the pumping membrane 361A, is in contact with at least 90 percent (e.g., at least 95 percent) of the surface area of the portion of the pumping membrane 361A that overlies the pumping chamber 338A. As a result, the pressure applied to the pumping membrane 361A by the piston head 334A is more uniformly distributed over the surface area of the pumping membrane 361A.

As the piston head 334A is further advanced, the pumping membrane 361A and the underlying portion of the membrane 340 are pushed into a recessed region 363A of the base 356 of the cassette 312, which reduces the volume of the pump chamber 338A and increases the fluid pressure within the pump chamber 338A. Such increased pressures within pump chambers can cause portions of membranes that overlie the pump chambers and are not in contact with the piston head to bulge outward if those membranes do not have sufficient strength to resist that pressure. By increasing the diameter of the leading portions of the piston head 334A, the surface area of the pumping membrane 361A contacted by the pump head 334A during the initial phases of the outward stroke of the pump head 334A is increased. As a result, the tendency of the flexible membrane 340 and the pumping membrane 361A to bulge outward due to increased fluid pressure within the pump chamber 338 is decreased. Additionally, the thickness of the combination of the flexible membrane 340 and the pumping membrane 361, which is greater than the thickness of many conventional fluid pumping cassette membranes, helps the flexible membrane 340 and the pumping membrane 361A to withstand the increased fluid pressure within the pump chamber 338A without bulging outward.

Figure 16D:
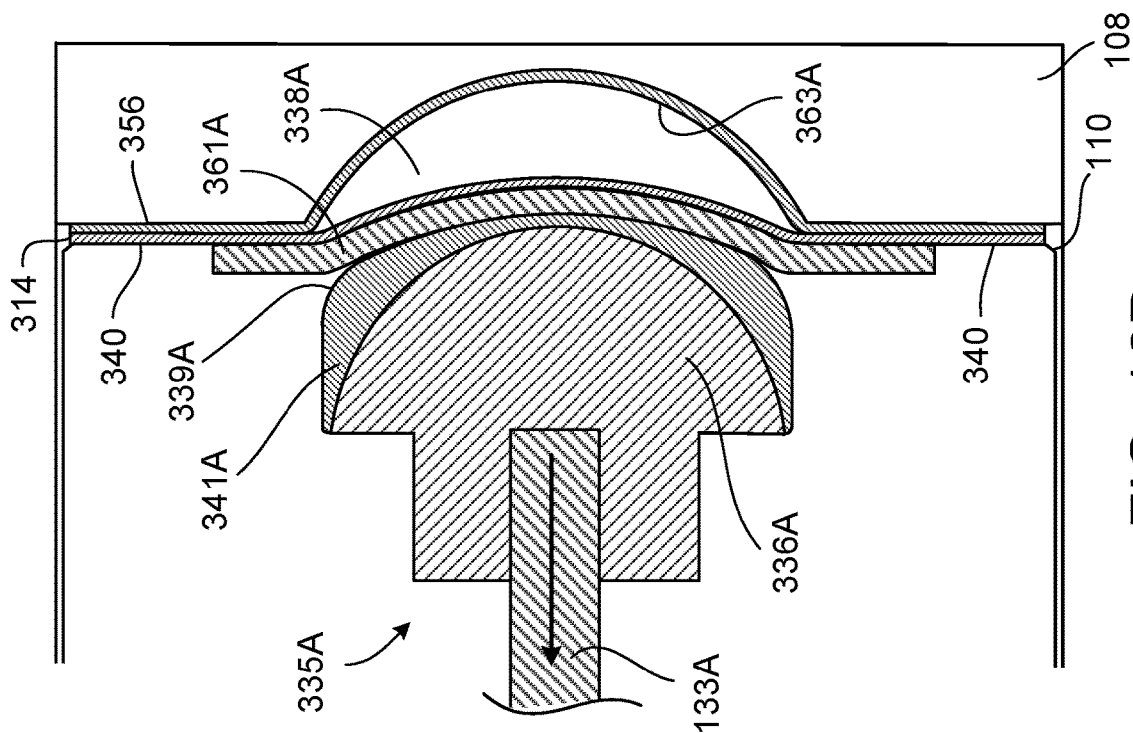
Figure 16C:
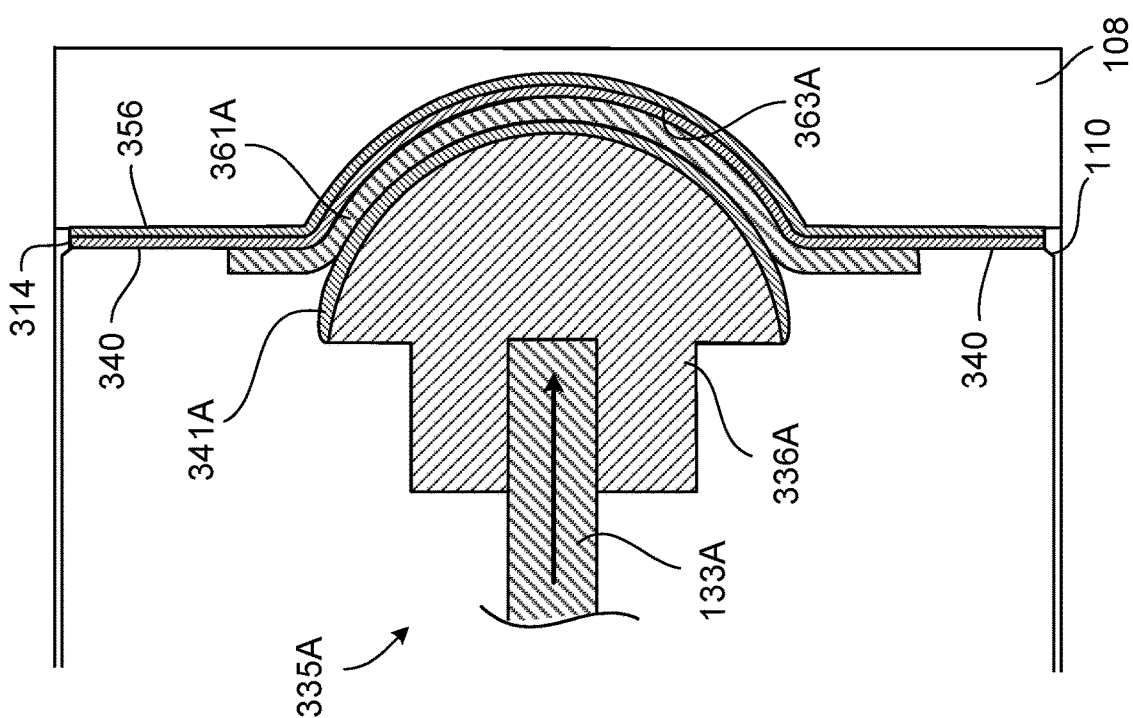

As shown in FIG. 16C, when the piston head 334A is fully extended, the compressible coating 341A is compressed to substantially conform to the shape of the recessed region 363A of the rigid base 156 of the cassette 112. In this position, the volume of the pump chamber 338A is at its minimum such that all or nearly all liquid that was present in the pump chamber 338A prior to advancement of the piston 335A will be expelled from the pump chamber 338A and into the fluid passageways 358 of the cassette 312 as the piston 335A is advanced into this fully extended position.

The leading portions of the piston head 334A that extend farthest into the recessed region 363A, when in an uncompressed state, have a greater diameter than the diameter of the portions of the of the recessed region 363A that those leading portions of the piston head 334A contact in this fully extended position. As the piston head 334A is advanced into its fully extended position, the resistance of the pumping membrane 361A and/or contact with the recessed region 363A of the base 356 causes the compressible coating 341A in those leading portions of the piston head 334A to compress. This compression of the coating 341A decreases the diameter of the leading portions of the piston head 334A and allows the piston head 334A to be fully received within the recessed region 363A of the base 312. In this way, the piston head 334A provides a sufficient contact area with the pumping membrane 361A during the initial phases of the outward stroke to prevent outward bulging of the flexible membrane 340 and the pumping membrane 361A, while also being capable of being fully inserted into the pump chamber 338A to ensure that the desired volume of fluid is expelled from the pump chamber 338A. Because outward bulging of the membranes 340, 361A is eliminated or at least significantly reduced, the pumping volume accuracy can be increased.

In order to draw PD solution into the pump chamber 338A, the piston head 334A is then retracted to a retracted position, as shown in FIG. 16D. As the piston head 334A retracts, the resilient pumping membrane 361A automatically rebounds (or self-expands) and pulls the portion of the flexible membrane 340 underlying the pump membrane 338A with it to increase the volume of the pump chambers 338A. This creates vacuum pressure within the pump chamber 338A and thus draws the PD solution into the pump chamber 338A.

After the pumping membrane 361A has rebounded to a sufficient extent to draw a desired volume of the PD solution into the pump chamber 338A, the dialysis fluid in the pump chamber 338A can be forced out of the pump chamber 338A by again returning the piston head 334A to the fully extended position shown in FIG. 16C, causing the pumping membrane 361A to deflect inward toward the rigid base 356 and thus decreasing the volume of the pump chamber 338A.

While forcing dialysis solution into and out of the pump chambers 338A, 338B, inflatable members of the PD cycler that align with the dome regions 346 of the cassette 312 can be selectively inflated to direct the pumped dialysis solution along desired pathways in the cassette 312 in order to carry out the PD treatment.

While the piston 335A has been described as being used with the cassette 312 of FIG. 14, it should be understood that the piston 335A can be used with any of the various other cassettes described herein. In addition, the piston 335A can be used with cassettes having only a thin, single-layer membrane over the pump chamber. An example of such a cassette would be the cassette of FIG. 14 but with the pumping membranes 361A, 361B removed. The piston 335A can be particularly useful with those types of cassettes due to the propensity of the thin, single-layer membrane to bulge outward in regions of the membrane that overlie the pump chamber when fluid pressures within the pump chamber increases.

Figure 17:
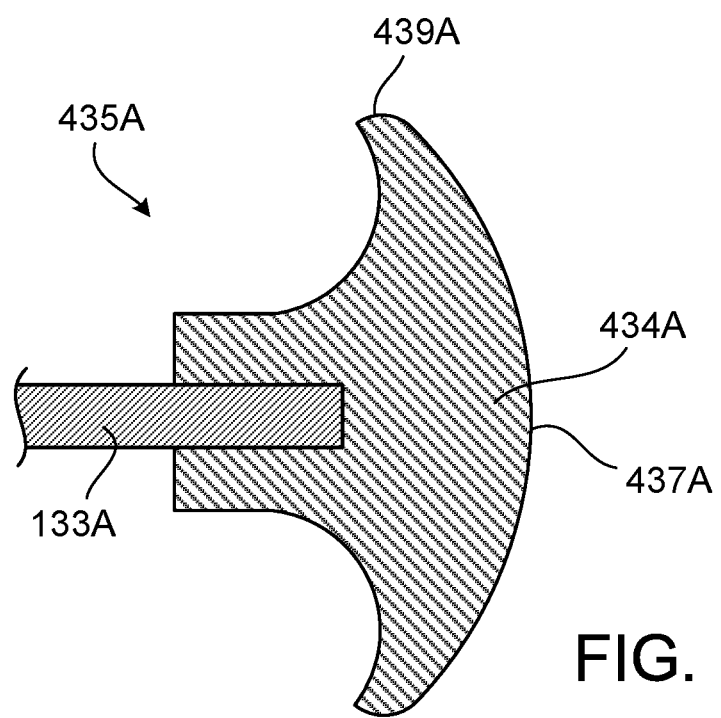
FIG. 17 is a cross-sectional view of a piston including a piston head formed of an elastomeric material that generally decreases in thickness from a central region of the piston head toward a periphery of the piston head.

While the piston head 334A has been described as having a core about which a compressible coating is disposed, other types of piston heads can be used. For example, FIG. 17 is a cross-sectional view of an alternative piston 435A that includes a piston head 434A that is formed of an elastomer. Any of the elastomers described above as being suitable for forming the compressible coating 341A of the piston head 334A can be used to form the piston head 434A. The thickness of the piston head 434A gradually decreases from a central portion 437A of the piston head 434A to an outer circumferential region 439A of the piston head 434A. The central portion 437A of the piston head 434A can, for example, be about 0.2 inch to about 0.55 inch thicker than the circumferential edge region 439A of the piston head 434A. In some implementations, the central portion 437A of the piston head 434A has a thickness of about 0.45 inch to about 0.65 inch and the circumferential edge region 439A of the piston head 434A has a thickness of about 0.1 inch to about 0.25 inch. Due to the decreased thickness of the elastomeric material near the outer circumference of the piston head 434A, the circumferential edge region 439A of the piston head 434A is more flexible than the central portion 437A of the piston head 434A.

The piston head 434A behaves in a manner similar to the piston head 334A illustrated in FIGS. 16A-16D when it is used to pump fluid out of and draw fluid into a pump chamber of any of the various cassettes described herein. In particular, due to the size and shape of the piston head 434A, the piston head 434A will contact a large surface area of the cassette membrane overlying the pump chamber to reduce the likelihood of outer circumferential regions of that membrane bulging outwardly as the piston head 434A is advanced to expel fluid from the pump chamber. As the piston head 434A is advanced further into the recessed region of the cassette base that forms the pump chamber, the resistance of the membrane and/or rigid cassette base itself will cause the outer portions of the piston head 434A to flex and ultimately conform to the general shape of the recessed region.

Figure 18A:
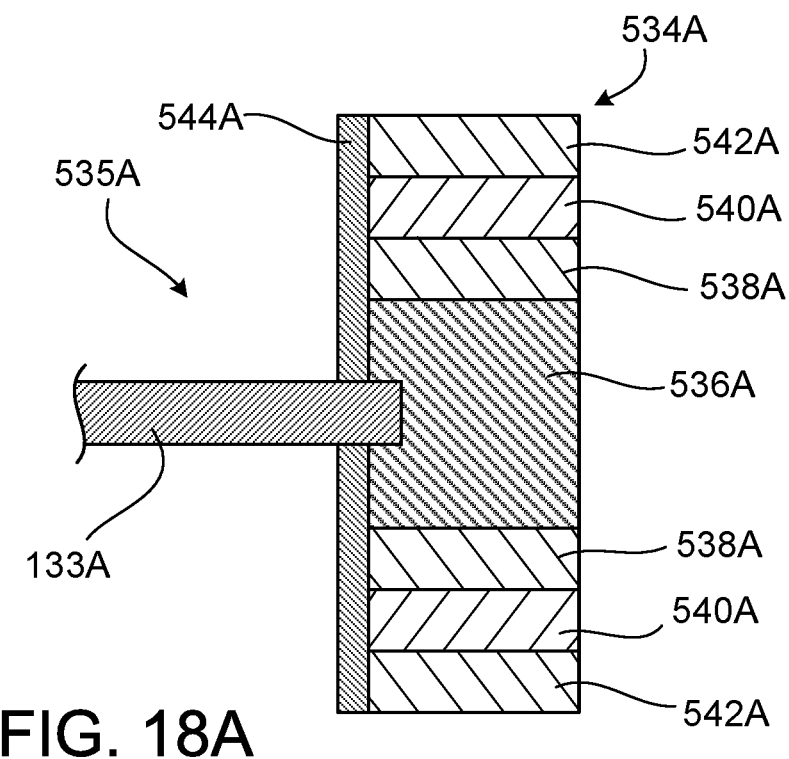
FIGS. 18A and 18B are cross-sectional views of a flat configuration and a deformed configuration, respectively, of a piston having a piston head that includes multiple concentric rings secured to a leaf spring.
Figure 18B:
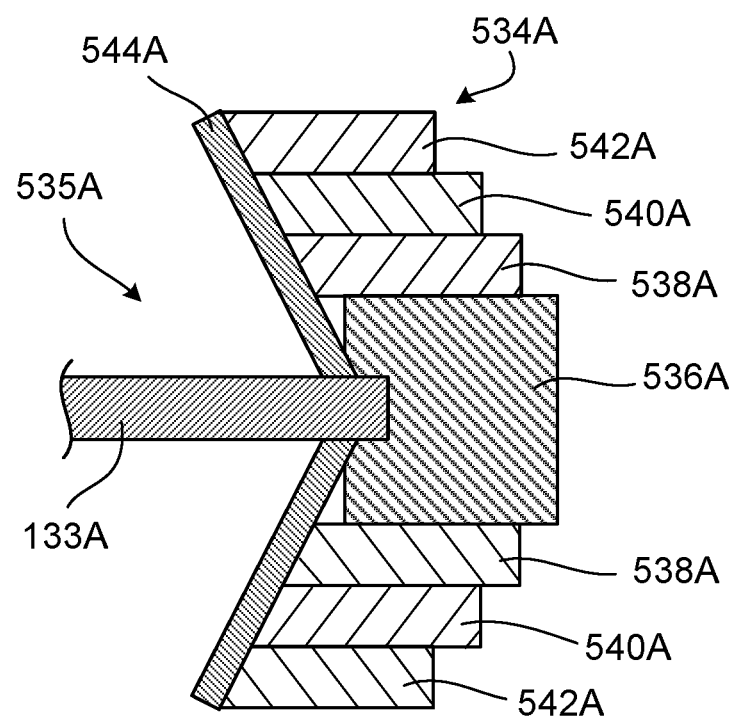

FIGS. 18A and 18B are cross-sectional views of a piston 535A having a piston head 534A that includes multiple concentric rings 538A, 540A, 542A secured to a leaf spring 544A. A cylindrical member 536A is attached to the leading end of the piston shaft 133A and is positioned at the center point of the concentric rings 538A, 540A, 542A. The leaf spring 544A is also attached to the piston shaft 133A. In some implementations, the leaf spring 544A includes an opening that receives the piston shaft 133A and the leaf spring 544A is welded to the piston shaft 133A around the circumference of that opening. However, other techniques, such as mechanical fastening techniques, can alternatively or additionally be used to secure the leaf spring 544A to the piston shaft 133A. The leaf spring 544A is biased to a flat or planar configuration, as shown in FIG. 18A. Thus, when no axial forces are being applied to the rings 538A, 540A, 542A of the piston head 534A, the piston head 534A will have a substantially flat front surface, as shown in FIG. 18A.

The piston head 534A can be used with any of the various cassettes described herein to pump fluid from and draw fluid into a pump chamber of the cassette. Due to the flat front face of the piston head 534A of the piston 535A, the piston 535A is particularly beneficial for use with the cassettes described herein that include one or more flat membranes that overlie the pump chamber. As the piston head 534A is advanced into contact with such a membrane, the front surface of the piston head 534A will contact substantially the entire surface area of the portion of the membrane overlying the pump chamber. As a result, a substantially uniform pressure will be applied over that portion of the membrane. As the piston head 534A is advanced into the recessed region of the base that forms the pump chamber, the outer ring 542A will contact the recessed region of the cassette base causing the leaf spring 544A to flex slightly. Upon further advancement of the piston head 534A, the next outermost ring 540A will contact the recessed region of the cassette base causing the leaf spring 544A to flex further. When the piston head 534A has been fully advanced into the recessed region of the cassette base, each of the concentric rings 538A, 540A, 542A will be in contact (through the cassette membrane) with the recessed region of the cassette base and the piston head 534A will generally conform to the shape of the recessed region, as shown in FIG. 18B.

While the leaf spring 544A has been described as being attached to the piston shaft 133A, the leaf spring 544A can alternatively or additionally be attached to the cylindrical member 536A on the end of the piston shaft 133A. The leaf spring 544A can, for example, be welded or mechanically fastened to the cylindrical member 536A.

While the concentric rings 538A, 540A, 542A and the cylindrical member 536A of the piston head 534A have been described as being exposed or open, in some implementations, an elastomeric cover or coating is applied to the front face of the piston head 534A. Alternatively, the entire piston head 534A can be encapsulated within such an elastomeric coating. The coating can help to provide a more gradual transition from one concentric ring to the next when the piston head 534A is advanced into the recessed region of the cassette base. Thus, the coating can help to ensure that a uniform force is applied to the portion of the membrane overlying the pump chamber throughout the pumping process, which can improve the pumping volume accuracy of the PD cycler.

While the piston head 534A has been described as including only three concentric rings, in certain implementations, more concentric rings are used to form the piston head. It will be appreciated that the use of more concentric rings that are smaller will provide a less abrupt transition from one ring to the next as the rings are deflected.

Figure 19A:
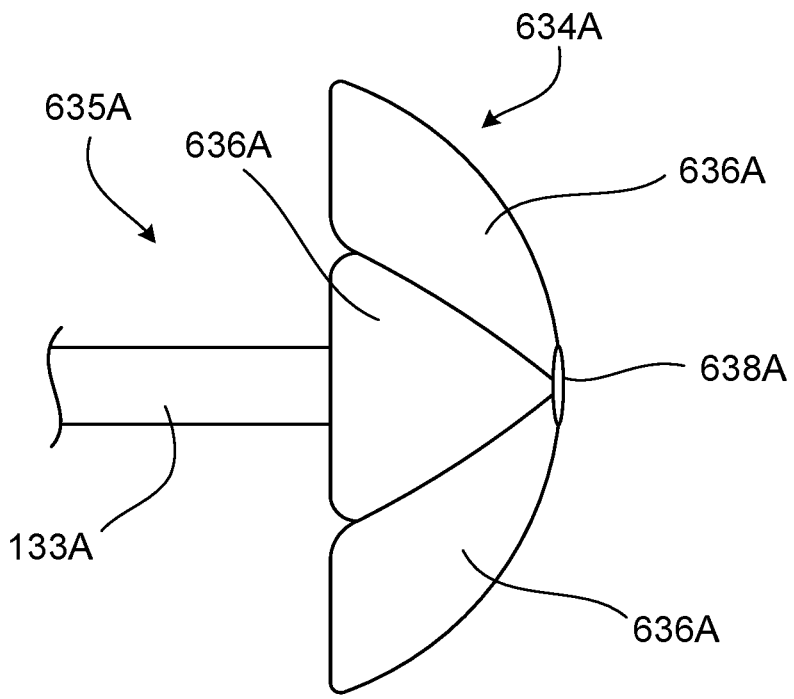
FIGS. 19A and 19B are side views of a piston having a piston head that includes multiple overlapping leaves, an expanded configuration and a compressed configuration, respectively.
Figure 19B:
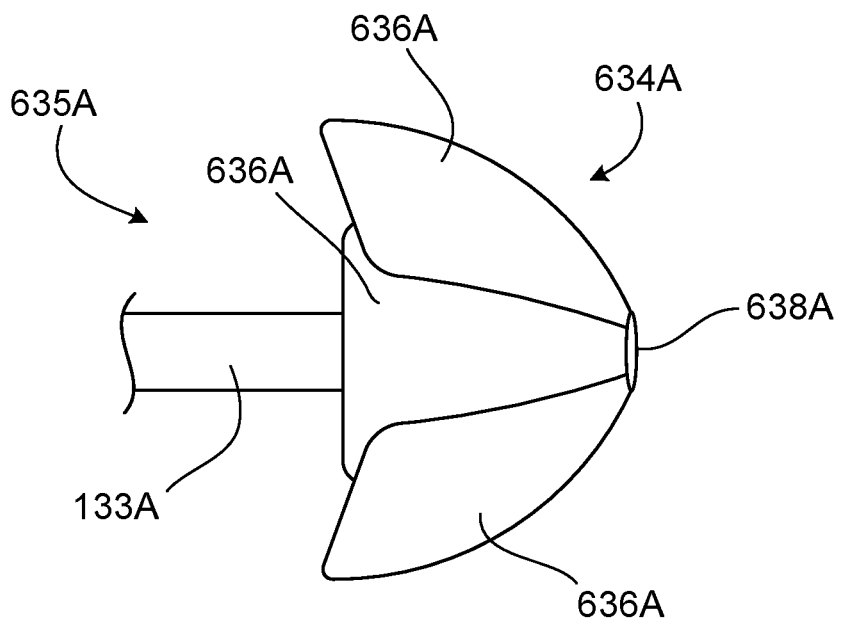

As an alternative to the types of compressible or collapsible piston heads described above, a piston head that includes overlapping segments that can collapse under one another can be used. As shown in FIGS. 19A and 19B, for example, a piston 635A has a piston head 634A that includes multiple overlapping leaves 636A that can transition from an expanded position (shown in FIG. 19A) to a contracted position (shown in FIG. 19B). The overlapping leaves 636A are all connected to one another via a pin 638A at the apex of the piston head 634A. Additionally, at points nearer the circumferential edge of the piston head 634A, adjacent leaves 636A are connected to one another via springs that bias the leaves 636A to the expanded position (shown in FIG. 19A) in which the leaves 636A only minimally overlap one another. As the piston head 634A is advanced into the recessed region of the cassette base during use, the force applied to the leaves 636A due to contact with the membrane and the cassette base exceeds the spring force of the spring and causes the overlapping leaves 636A to collapse under one another. As a result, the diameter of the piston head 634A decreases, allowing the piston head 634A to generally conform to the shape of the recessed region of the cassette base that forms the pump chamber (shown in FIG. 19B). Because the piston head 634A is larger than the recessed region of the cassette base, the area of the membrane contacted by the piston head 634A can be greater during the initial phases of the outward stroke of the piston 635A than conventional rigid piston heads, which are generally sized and shaped to match the size and shape of the recessed region of the cassette base. As a result the force of the piston head 634A can be more uniformly applied to the membrane resulting in less bulging of the membrane and greater pumping volume accuracy.

While certain PD cyclers above have been described as including a touch screen and associated buttons, the PD cycler can include other types of screens and user data entry systems. In certain implementations, for example, the cycler includes a display screen with buttons (e.g., feathertouch buttons) arranged on the console adjacent the display screen. Certain buttons can be arranged to be aligned with operational options displayed on the screen during use such that the user can select a desired operational option by pressing the button aligned with that operational option. Additional buttons in the form of arrow buttons can also be provided to allow the user to navigate through the various display screens and/or the various items displayed on a particular screen. Other buttons can be in the form of a numerical keypad to allow the user to input numerical values in order, for example, to input operational parameters. A select or enter button can also be provided to allow the user to select an operational option to which the user navigated by using the arrow keys and/or to allow the user to enter values that the user inputted using the numerical keypad.

While the doors of the PD cyclers described above are shown as being positioned on a front face of the PD cyclers, the doors can alternatively be positioned at various other locations on the PD cyclers. For example, the doors could be positioned on a top face of the PD cycler such that the cassette is slid into the cassette compartment in a substantially horizontal orientation instead of a substantially vertical orientation.

While some of the PD cyclers discussed above have been described as including inflatable pads in their doors to compress the cassette between the door and the cassette interface, the PD cyclers can alternatively or additionally include inflatable pads positioned behind the cassette interface.

While the cassettes described above have been described as being part of a PD system, these types of cassettes can be used in any of various other types of cassette-based medical fluid pumping systems. Other examples of medical fluid pumping systems with which cassettes described herein can be used include hemodialysis systems, blood perfusion systems, and intravenous infusion systems.

Similarly, while the cassettes have been described as being used to pump dialysis solution, other types of dialysis fluids can be pumped through the cassettes. As an example, in the case of cassettes used with hemodialysis machines, blood can be pumped through the cassettes. In addition, priming solutions, such as saline, can similarly be pumped through cassettes using the various different systems and techniques described above. Similarly, as an alternative to dialysis fluids, any of various other types of medical fluids can be pumped through the above-described cassettes depending on the type of medical fluid pumping machines with which the cassettes are used.

What is claimed is:

1. A medical fluid delivery method, comprising:
expelling a medical fluid from a fluid pump chamber defined between a membrane and a base of a medical fluid cassette by pressing a piston head against the membrane to move the membrane toward the base, wherein a circumferential region of the piston head comprises a compressible coating that is configured to move radially inward as the piston head is pressed against the membrane to move the membrane toward the base.

2. The medical fluid delivery method of claim 1, wherein at any given time throughout an outward stroke of the piston head, an area of a portion of the piston head in contact with the membrane is substantially equal to an area of the fluid pump chamber in a plane in which the membrane lies.

3. The medical fluid delivery method of claim 1, wherein the medical fluid is dialysate.

4. The medical fluid delivery method of claim 1, wherein the compressible coating comprises a flexible elastomeric material.

5. The medical fluid delivery method of claim 1, wherein a thickness of the compressible coating increases from a central region toward an outer circumferential edge region.

6. The medical fluid delivery method of claim 1, wherein at least a portion of the compressible coating conforms to a shape of the base of the medical fluid cassette when the piston head is pressed against the membrane to move the membrane toward the base.

7. The medical fluid delivery method of claim 1, wherein the piston head comprises a core and the compressible coating is positioned around the core.

8. The medical fluid delivery method of claim 1, wherein the compressible coating is compressed between the piston head and the membrane when the piston head is pressed against the membrane to move the membrane toward the base.

9. The medical fluid delivery method of claim 1, wherein at least one region of the compressible coating deforms and changes thickness when the piston head is pressed against the membrane to move the membrane toward the base.

* * * * *